United States Patent
Geng et al.

(10) Patent No.: US 10,562,900 B2
(45) Date of Patent: Feb. 18, 2020

(54) INDAZOLE COMPOUNDS AS FGFR KINASE INHIBITOR, PREPARATION AND USE THEREOF

(71) Applicants: Shanghai Haihe Pharmaceutical Co., Ltd., Shanghai (CN); Shanghai Institute of Materia Medica, Chinese Academy of Sciences, Shanghai (CN)

(72) Inventors: Meiyu Geng, Shanghai (CN); Lei Liu, Shanghai (CN); Lei Jiang, Shanghai (CN); Min Huang, Shanghai (CN); Chuantao Zha, Shanghai (CN); Jing Ai, Shanghai (CN); Lei Wang, Shanghai (CN); Jianhua Cao, Shanghai (CN); Jian Ding, Shanghai (CN)

(73) Assignees: Shanghai Haihe Pharmaceutical Co., Ltd., Shanghai (CN); Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 15/504,854

(22) PCT Filed: Aug. 19, 2015

(86) PCT No.: PCT/CN2015/087556
§ 371 (c)(1),
(2) Date: Feb. 17, 2017

(87) PCT Pub. No.: WO2016/026445
PCT Pub. Date: Feb. 25, 2016

(65) Prior Publication Data
US 2017/0275291 A1    Sep. 28, 2017

(30) Foreign Application Priority Data

Aug. 19, 2014    (CN) .......................... 2014 1 0409467
Feb. 11, 2015    (CN) .......................... 2015 1 0073179

(51) Int. Cl.
| | | |
|---|---|---|
| *C07D 487/04* | (2006.01) |
| *C07D 231/56* | (2006.01) |
| *C07D 519/00* | (2006.01) |
| *C07D 401/12* | (2006.01) |
| *C07D 471/04* | (2006.01) |
| *C07D 403/12* | (2006.01) |
| *C07D 498/04* | (2006.01) |
| *C07D 401/14* | (2006.01) |
| *C07D 405/14* | (2006.01) |
| *C07D 417/12* | (2006.01) |
| *A61K 31/416* | (2006.01) |
| *A61K 31/496* | (2006.01) |

(52) U.S. Cl.
CPC .......... *C07D 487/04* (2013.01); *A61K 31/416* (2013.01); *A61K 31/496* (2013.01); *C07D 231/56* (2013.01); *C07D 401/12* (2013.01); *C07D 401/14* (2013.01); *C07D 403/12* (2013.01); *C07D 405/14* (2013.01); *C07D 417/12* (2013.01); *C07D 471/04* (2013.01); *C07D 498/04* (2013.01); *C07D 519/00* (2013.01)

(58) Field of Classification Search
None
See application file for complete search history.

(56) References Cited

U.S. PATENT DOCUMENTS

2014/0171405 A1    6/2014    Zhuo et al.

FOREIGN PATENT DOCUMENTS

| CN | 101962365 | 2/2011 |
| WO | WO 2003/068773 A1 | 8/2003 |
| WO | WO 2014/052563 A2 | 4/2014 |

OTHER PUBLICATIONS

Golub et al., Science, vol. 286, Oct. 15, 1999, pp. 531-537.*
Liu et al., Design, synthesis and biological evaluation of novel FGFR inhibitors bearing an indazole scaffold. Org Biomol Chem. Jul. 28, 2015;13(28):7643-54. doi: 10.1039/c5ob00778j.
PCT/CN2015/087556, Nov. 25, 2015, International Search Report.

* cited by examiner

*Primary Examiner* — Kamal A Saeed
(74) *Attorney, Agent, or Firm* — Wolf, Greenfield & Sacks, P.C.

(57) ABSTRACT

The present invention provides an indazole compound as a FGFR kinase inhibitor, preparation and use thereof. Specifically, the present invention provides a compound represented by formula (I), wherein the definitions of each group are described in the specification. The compound of the present invention has good FGFR kinase-inhibiting activity, and can be used in preparing a series of medicines for treating FGFR kinase activity related diseases.

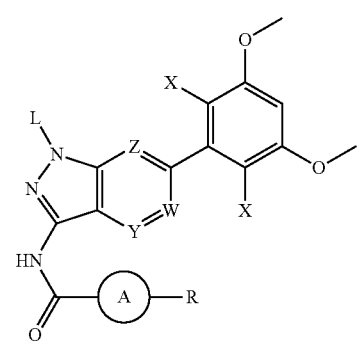

15 Claims, No Drawings

INDAZOLE COMPOUNDS AS FGFR KINASE INHIBITOR, PREPARATION AND USE THEREOF

CROSS-REFERENCE TO RELATED APPLICATIONS

This application is a national stage filing under 35 U.S.C. § 371 of international application number PCT/CN2015/087556, filed Aug. 19, 2015, which claims priority to Chinese Patent Application No. 201510073179.8, filed Feb. 11, 2015, and Chinese Patent Application No. 201410409467.1, filed Aug. 19, 2014. The content of each of the prior applications is incorporated by reference herein in its entirety.

FIELD OF THE INVENTION

The present invention belongs to the field of pharmaceutical, and specifically, the present invention relates to indazole compounds as FGFR kinase inhibitor, preparation and use thereof.

BACKGROUND OF THE INVENTION

Receptor tyrosine kinase plays a key role various aspects of tumor such as tumor genesis and development, invasion and metastasis, and drug resistance because of the activation of its abnormal expression or gene mutation. It has become an important target for anti-tumor drug research and development. Among them, fibroblast growth factor receptors (FGFRs) are important members of the receptor tyrosine kinase family, mainly including four subtypes, FGFR1, FGFR2, FGFR3 and FGFR4. The ligand thereof is fibroblast growth factors (FGFs). Because of gene amplification, mutation, fusion or ligand induction and other reasons, the various members of FGFRs are continuously activated, inducing tumor cell proliferation, invasion, migration, promoting angiogenesis and promoting the genesis and development of tumor. FGFRs are highly expressed and abnormally activated in a variety of tumors, and are closely associated with poor prognosis in patients such as those with non-small cell lung cancer, breast cancer, stomach cancer, bladder cancer, endometrial cancer, prostate cancer, cervical cancer, colon cancer, esophageal cancer, glioblastoma, myeloma, rhabdomyosarcoma and the like. Studies have shown that FGFR1 amplification accounts for 20% of non-small cell lung cancer squamous cell carcinoma, and the studies of in vitro proliferation and signaling pathway of the lung cancer cell strains with FGFR1 proliferation have shown that FGFR selective inhibitors can effectively inhibit the activation of FGFR1 signaling pathway and cell proliferation. In breast cancer, the amplification of the chromosome region (8p11-12) where FGFR1 locates makes up approximately 10% of the ER-positive patients, and is associated with high expression of FGFR1 mRNA and poor prognosis of patients. FGFR2 gene amplification or mutation results in the abnormal activation of the FGFR2 signaling pathway, which is mainly associated with gastric cancer, triple negative breast cancer, endometrial cancer and the like. The amplification rate of FGFR2 in gastric cancer tissue is 5%-10%. Analysis of 313 cases of gastric cancer showed that the amplification of FGFR2 was significantly associated with tumor size, local infiltration, lymph node metastasis and distant metastasis, and furthermore, the gastric cancers with FGFR2-amplification are usually progressive tumor with poor prognosis, and the overall survival rate of patients is relatively low. FGFR2 amplification accounted for 4% of the refractory triple-negative breast cancers. Endometrial cancer is a common gynecological reproductive tract tumor, FGFR2 mutation accounts for about 12% of endometrial cancer. In non-invasive bladder cancers, FGFR3 mutations accounts for 50%-60%, and in invasive bladder cancers, FGFR3 mutations accounts for 10%-15%. The gene rearrangement of FGFR3t (4; 14) (p16.3; q32) accounts for 15-20% of multiple myeloma. Meanwhile, various subtypes of FGFR and the ligands thereof (FGFs), such as FGFR2, FGFR3, FGFR4, FGF19, FGF2, FGF5, FGF8, FGF9, have shown aberrant expression and activation in liver cancer. Numerous preclinical and clinical studies have shown the importance of FGF/FGFR axis abnormal activation in liver cancer. It can not be ignored that abnormal activation of the FGF/FGFR axis is closely related to the drug-resistance to EGFR inhibitors, neovascularization inhibitors, and endocrine therapy. Therefore, development of the inhibitors targeting FGFR has become a hot spot in the field of anticancer drug research.

SUMMARY OF THE INVENTION

The purpose of the present invention is to provide a novel inhibitor targeting FGFR.

In the first aspect of the present invention, a compound of formula I, or a pharmaceutically acceptable salt thereof is provided,

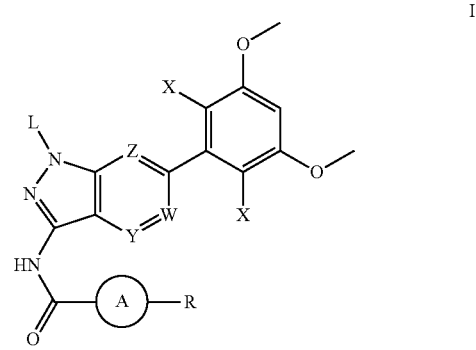

wherein:

L is selected from the group consisting of: H, tetrahydropyranyl (THP);

each X is independently selected from the group consisting of: Cl, F, H, and CN;

W, Y, and Z are each independently selected from: N or CH;

ring A is absent, unsubstituted or substituted 5- to 8-membered arylene group, or a unsubstituted or substituted 5- to 8-membered heteroarylene group, wherein the heteroarylene group contains at least one heteroatom selected from the group consisting of nitrogen, oxygen, or sulfur; unsubstituted or substituted 3- to 12-membered saturated heterocyclic ring or carbocyclic ring, wherein the heterocyclic ring contains at least one heteroatom selected from the group consisting of nitrogen, oxygen, or sulfur;

R is H, or a substituted or unsubstituted group selected from the group consisting of:

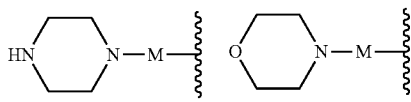

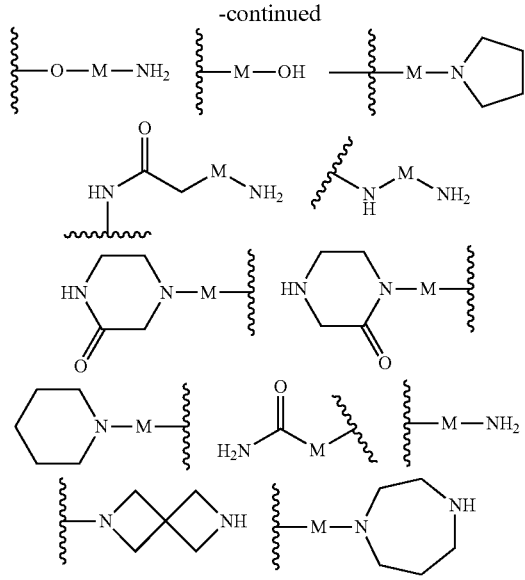

wherein M is selected from the group consisting of: substituted or unsubstituted C1-C6 alkylene, substituted or unsubstituted C6-C10 arylene, substituted or unsubstituted C1-C10 heteroarylene, or M is absent;

wherein the term "substituted" in any occasion means that one or more hydrogen atoms on said group are substituted with a substituent selected from the group consisting of: halogen, unsubstituted or halogenated C1-C6 alkyl, unsubstituted or halogenated C1-C6 alkoxy group, unsubstituted or halogenated C1-C6 alkoxyalkyl group, unsubstituted or halogenated C3-C8 cycloalkyl group, unsubstituted or halogenated C2-C6 alkylcarbonyl group, unsubstituted or halogenated C1-C6 alkylene-hydroxy, unsubstituted or C1-C6 alkyl-substituted amine group.

In another preferred embodiment, said ring A is a heteroaryl or saturated heterocyclic ring selected from the group consisting of the following, or ring A is absent:

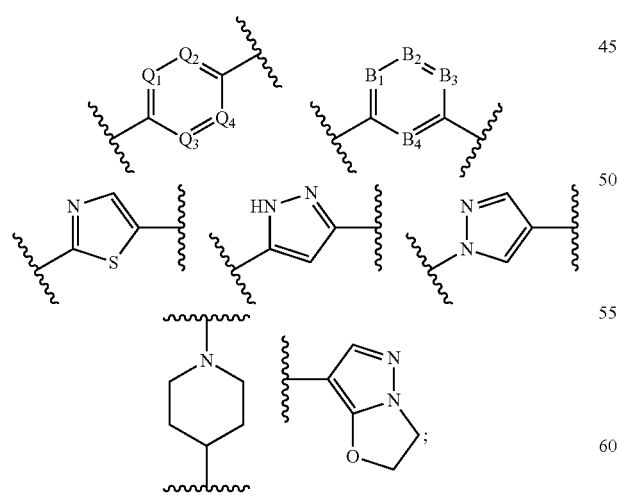

wherein, $Q_1$, $Q_2$, $Q_3$ and $Q_4$ are each independently selected from: N or CH;

$B_1$, $B_2$, $B_3$ and $B_4$ are each independently selected from: N or CH.

In another preferred embodiment, said ring A is a heteroaryl or saturated heterocyclic ring selected from the group consisting of the following, or ring A is absent:

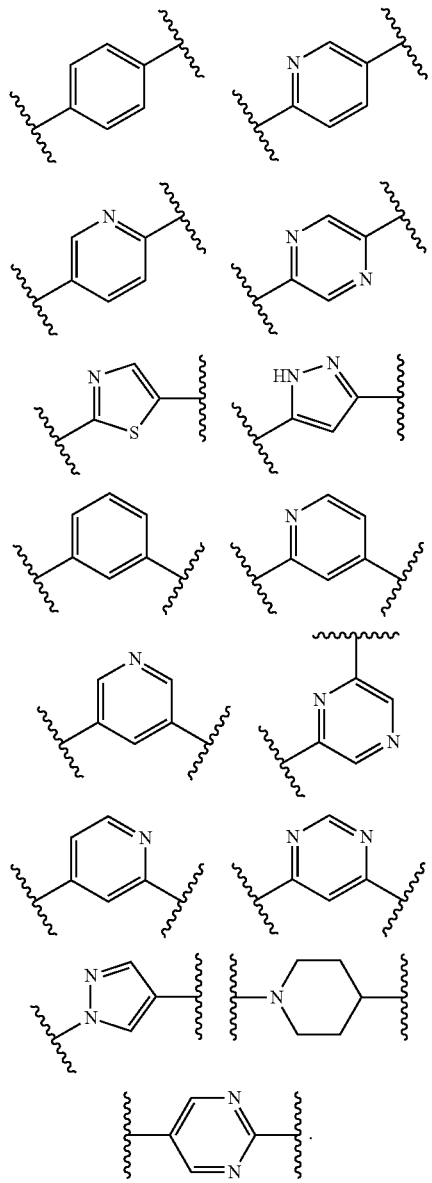

In another preferred embodiment, R is substituted or unsubstituted group selected from the group consisting of:

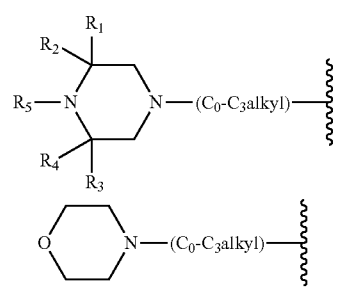

-continued

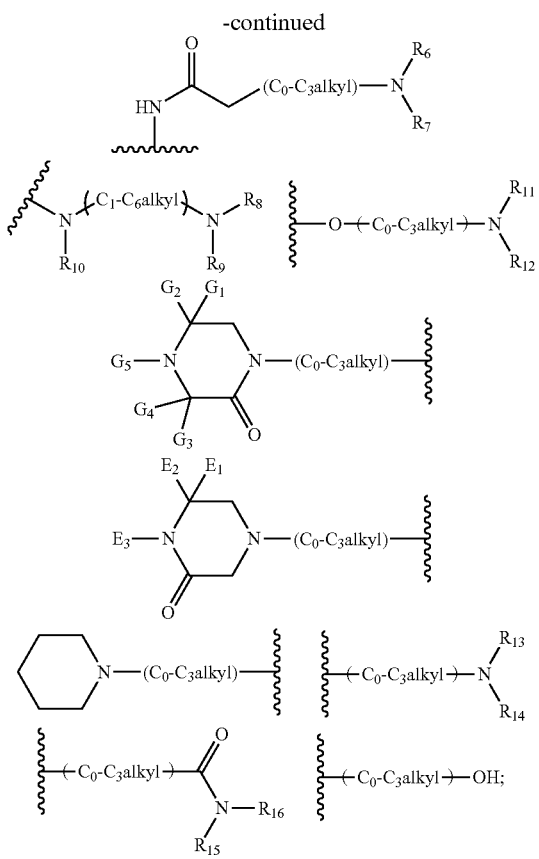

wherein:

$R_1$, $R_2$, $R_3$, $R_4$ are each independently selected from the group consisting of: H, halogen, C1-C6 linear or branched alkyl, halogenated C1-C6 linear or branched alkyl;

$R_5$ is selected from the group consisting of: H, C1-C6 linear or branched alkyl, C1-C6 linear or branched alkyl-carbonyl, C1-C6 linear or branched alkylene-hydroxy, C1-C6 alkoxyalkyl, unsubstituted or alkyl-substituted amino group, C1-C8 cycloalkyl group.

$R_6$, $R_7$, $R_8$, $R_9$, $R_{10}$, $R_{11}$, $R_{12}$ are each independently selected from the group consisting of: H, C1-C6 linear or branched alkyl, C1-C6 linear or branched alkylcarbonyl, C1-C6 linear or branched alcohol group (alkylene-hydroxy);

$G_1$, $G_2$, $G_3$, $G_4$ are each independently selected from the group consisting of: H, halogen, C1-C6 linear or branched alkyl, halogenated C1-C6 linear or branched alkyl;

$G_5$ is selected from the group consisting of: H, C1-C6 linear or branched alkyl, C1-C6 linear or branched alkyl-carbonyl, C1-C6 linear or branched alkyl-hydroxy, C1-C6 alkoxyalkyl, unsubstituted or alkyl-substituted amino group, C1-C8 cycloalkyl group;

$E_1$, $E_2$ are each independently selected from the group consisting of: H, halogen, linear or branched alkyl, halogenated C1-C6 linear or branched alkyl;

$E_3$ is selected from the group consisting of: H, C1-C6 linear or branched alkyl, C1-C6 linear or branched alkyl-carbonyl, C1-C6 linear or branched alkylene-hydroxy, C1-C6 alkoxyalkyl, unsubstituted or alkyl-substituted amino group, C1-C8 cycloalkyl group;

$R_{13}$, $R_{14}$, $R_{15}$, $R_{16}$ are each independently selected from the group consisting of: H, C1-C6 linear or branched alkyl, C1-C6 linear or branched alkylcarbonyl, C1-C6 linear or branched alcohol group (alkylene-hydroxy), or R13 and R14, or R15 and R16 attach to a carbon atom so as to form a 5- to 7-membered ring;

C0-C3 alkyl means absent, or alkylene with 1-3 carbon atoms;

C1-C6 alkyl is alkylene with 1-6 carbon atoms;

In another preferred embodiment,

L is selected from the group consisting of: H, tetrahydropyranyl (THP);

Each X is independently selected from the group consisting of: H, Cl, F, and CN;

W, Y, and Z are each independently selected from: N or CH;

ring A is unsubstituted or substituted 6-membered aryl group, or unsubstituted or substituted 5- to 6-membered heteroaryl group, wherein the heteroaryl group contains at least one heteroatom selected from the group consisting of nitrogen, oxygen, and sulfur;

M is selected from the group consisting of: unsubstituted or substituted C1-C4 alkylene, or M is absent; wherein the term "substituted" means that one or more hydrogen atoms on said group are substituted with a substituent selected from the group consisting of: halogen, unsubstituted or halogenated C1-C4 alkyl, unsubstituted or halogenated C1-C6 alkoxy group, unsubstituted or halogenated C2-C6 alkoxyalkyl, unsubstituted or halogenated C3-C8 cycloalkyl group, unsubstituted or halogenated C2-C4 alkylcarbonyl group, unsubstituted or halogenated C1-C4 alkyl-hydroxy, unsubstituted or C1-C6 alkyl-substituted amine group. In another preferred embodiment, L is H;

each X is independently selected from the group consisting of: H, Cl, and F;

W, Y, and Z are each independently selected from: N or CH;

ring A is a group selected from the group consisting of: none, phenyl, pyrazolyl, pyridyl, thiazolyl, pyrimidinyl, pyrazinyl or piperidinyl;

M is selected from the group consisting of: unsubstituted or substituted C1-C3 alkylene group, or M is absent;

wherein the term "substituted" in any occasion means that one or more hydrogen atoms on said group are substituted with a substituent selected from the group consisting of: halogen, unsubstituted or halogenated C1-C4 alkyl, unsubstituted or halogenated C2-C6 alkoxy group, unsubstituted or halogenated C2-C6 alkoxyalkyl group, unsubstituted or halogenated C3-C8 cycloalkyl group, unsubstituted or halogenated C2-C6 alkylcarbonyl group, unsubstituted or halogenated C1-C4 alkyl-hydroxy, unsubstituted or C1-C4 alkyl-substituted amine group.

In another preferred embodiment, the compound of formula I is selected from the following table A:

TABLE A

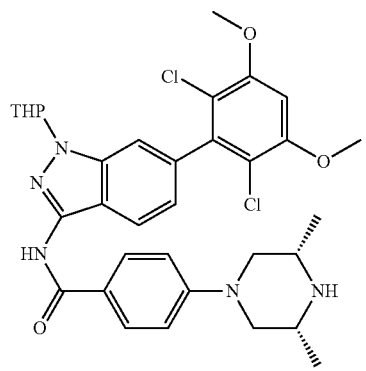

TABLE A-continued
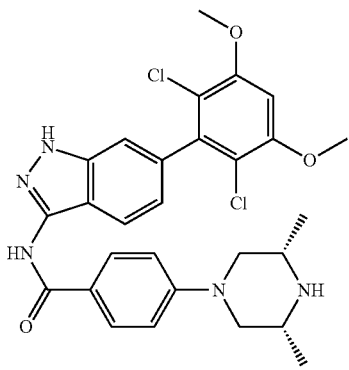
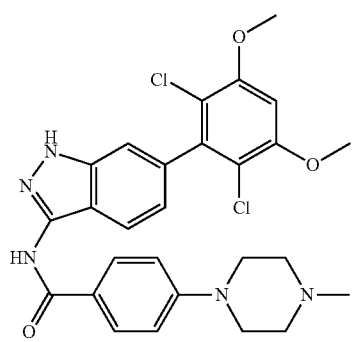
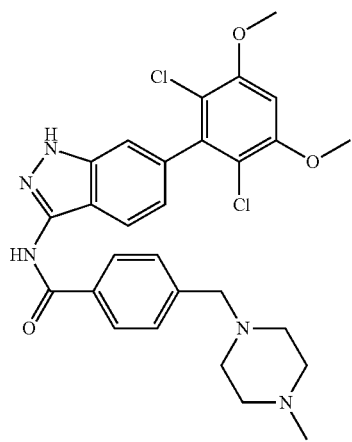 [SMILES: COc1cc(OC)c(Cl)c(-c2ccc3c(NC(=O)c4ccc(CN5CCN(C)CC5)cc4)n[nH]c3c2)c1Cl]
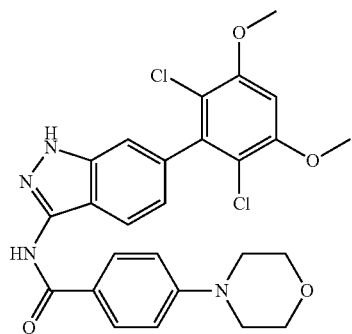 [SMILES: COc1cc(OC)c(Cl)c(-c2ccc3c(NC(=O)c4ccc(N5CCOCC5)cc4)n[nH]c3c2)c1Cl]
TABLE A-continued
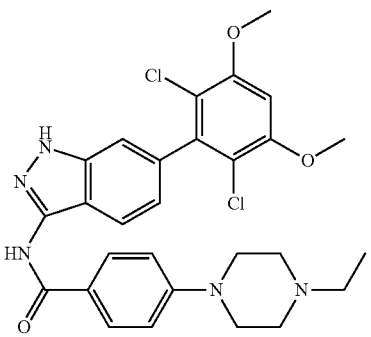 [SMILES: CCN1CCN(c2ccc(C(=O)Nc3n[nH]c4cc(-c5c(Cl)c(OC)cc(OC)c5Cl)ccc34)cc2)CC1]
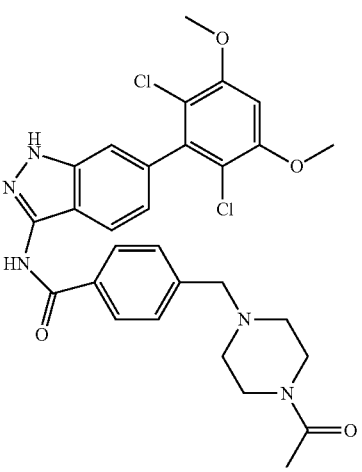 [SMILES: COc1cc(OC)c(Cl)c(-c2ccc3c(NC(=O)c4ccc(CN5CCN(C(C)=O)CC5)cc4)n[nH]c3c2)c1Cl]
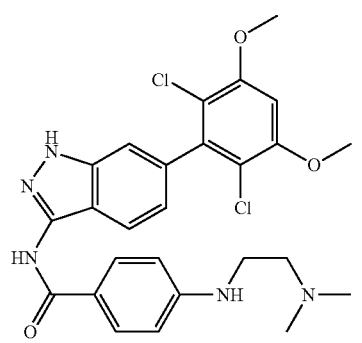 [SMILES: COc1cc(OC)c(Cl)c(-c2ccc3c(NC(=O)c4ccc(NCCN(C)C)cc4)n[nH]c3c2)c1Cl]
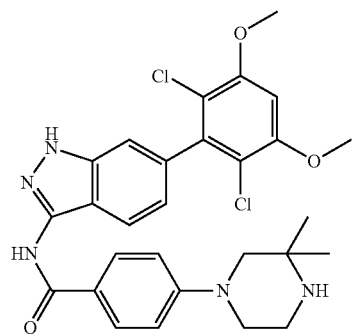

TABLE A-continued
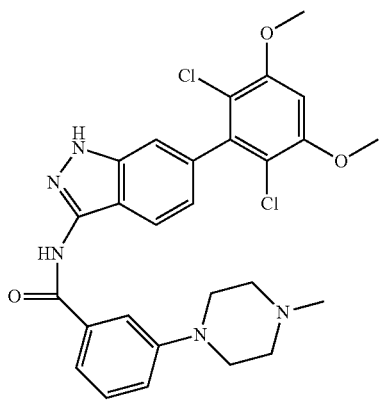 [SMILES: COc1cc(OC)c(Cl)c(-c2ccc3c(NC(=O)c4cccc(N5CCN(C)CC5)c4)n[nH]c3c2)c1Cl]
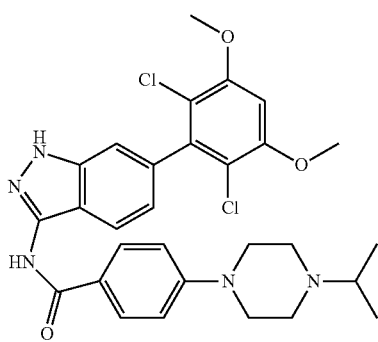 [SMILES: COc1cc(OC)c(Cl)c(-c2ccc3c(NC(=O)c4ccc(N5CCN(C(C)C)CC5)cc4)n[nH]c3c2)c1Cl]
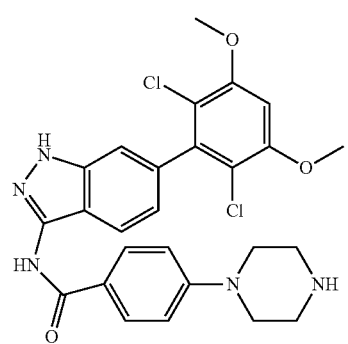 [SMILES: COc1cc(OC)c(Cl)c(-c2ccc3c(NC(=O)c4ccc(N5CCNCC5)cc4)n[nH]c3c2)c1Cl]
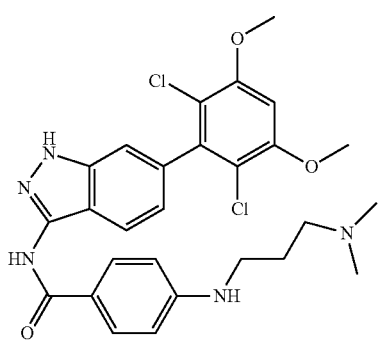 [SMILES: COc1cc(OC)c(Cl)c(-c2ccc3c(NC(=O)c4ccc(NCCCN(C)C)cc4)n[nH]c3c2)c1Cl]
TABLE A-continued
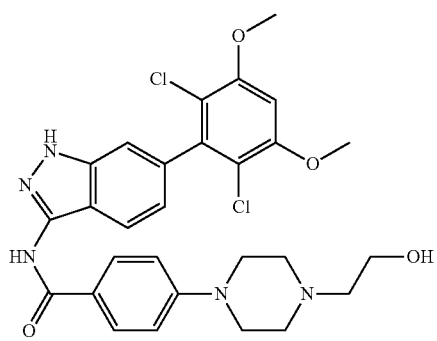 [SMILES: COc1cc(OC)c(Cl)c(-c2ccc3c(NC(=O)c4ccc(N5CCN(CCO)CC5)cc4)n[nH]c3c2)c1Cl]
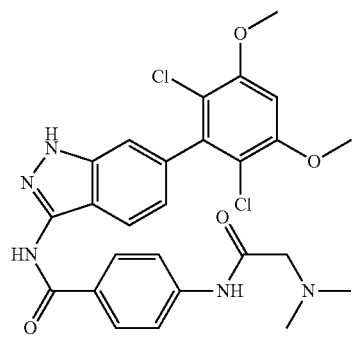 [SMILES: COc1cc(OC)c(Cl)c(-c2ccc3c(NC(=O)c4ccc(NC(=O)CN(C)C)cc4)n[nH]c3c2)c1Cl]
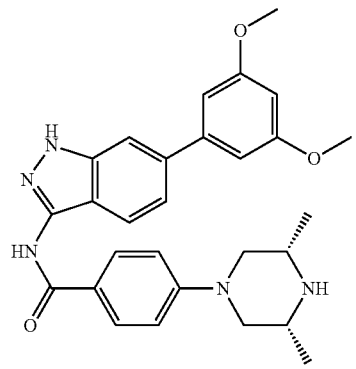 [SMILES: COc1cc(OC)cc(-c2ccc3c(NC(=O)c4ccc(N5C[C@@H](C)N[C@@H](C)C5)cc4)n[nH]c3c2)c1]
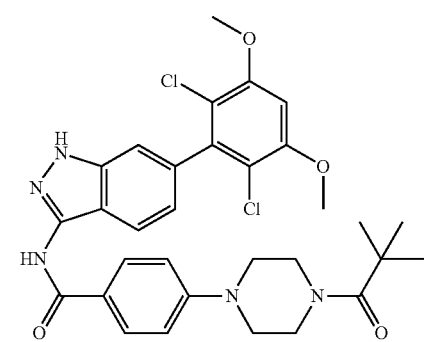 [SMILES: COc1cc(OC)c(Cl)c(-c2ccc3c(NC(=O)c4ccc(N5CCN(C(=O)C(C)(C)C)CC5)cc4)n[nH]c3c2)c1Cl]

TABLE A-continued
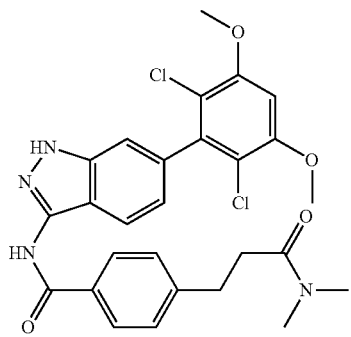 [SMILES: COc1cc(OC)c(Cl)c(-c2ccc3c(NC(=O)c4ccc(CCC(=O)N(C)C)cc4)n[nH]c3c2)c1Cl]
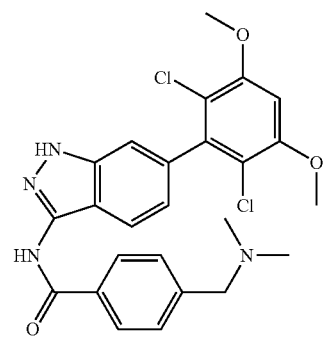 [SMILES: COc1cc(OC)c(Cl)c(-c2ccc3c(NC(=O)c4ccc(CN(C)C)cc4)n[nH]c3c2)c1Cl]
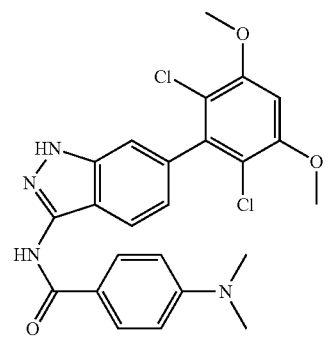 [SMILES: COc1cc(OC)c(Cl)c(-c2ccc3c(NC(=O)c4ccc(N(C)C)cc4)n[nH]c3c2)c1Cl]
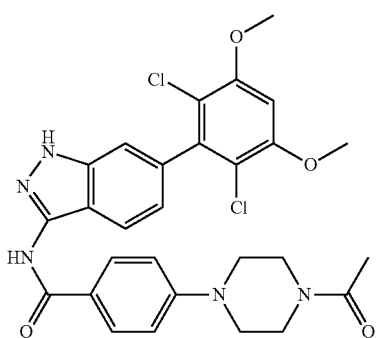 [SMILES: COc1cc(OC)c(Cl)c(-c2ccc3c(NC(=O)c4ccc(N5CCN(C(C)=O)CC5)cc4)n[nH]c3c2)c1Cl]
TABLE A-continued
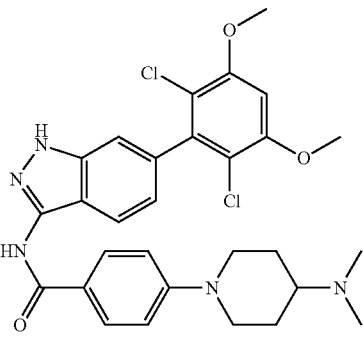 [SMILES: COc1cc(OC)c(Cl)c(-c2ccc3c(NC(=O)c4ccc(N5CCC(N(C)C)CC5)cc4)n[nH]c3c2)c1Cl]
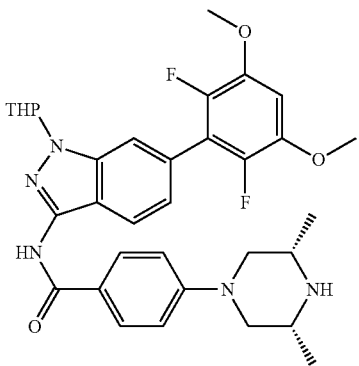
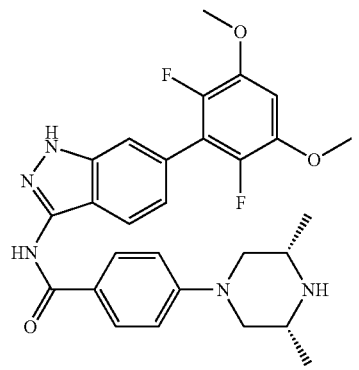 [SMILES: COc1cc(OC)c(F)c(-c2ccc3c(NC(=O)c4ccc(N5C[C@@H](C)N[C@@H](C)C5)cc4)n[nH]c3c2)c1F]
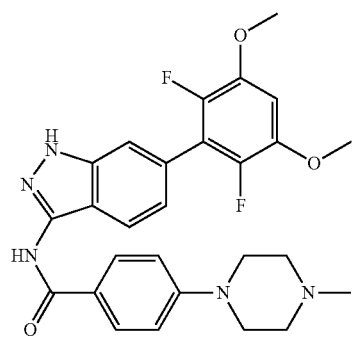

TABLE A-continued
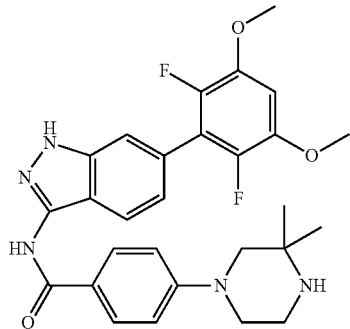 [SMILES: COc1cc(OC)c(F)c(-c2ccc3c(NC(=O)c4ccc(N5CCNC(C)(C)C5)cc4)n[nH]c3c2)c1F]
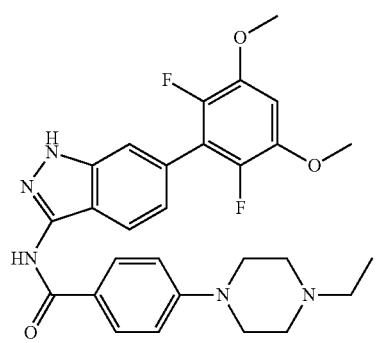 [SMILES: CCN1CCN(c2ccc(C(=O)Nc3n[nH]c4cc(-c5c(F)c(OC)cc(OC)c5F)ccc34)cc2)CC1]
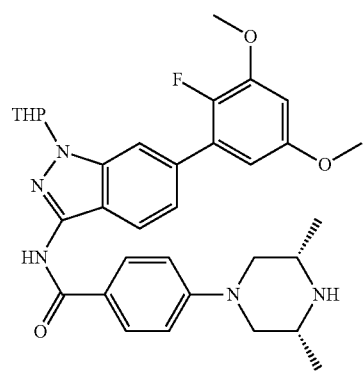
54
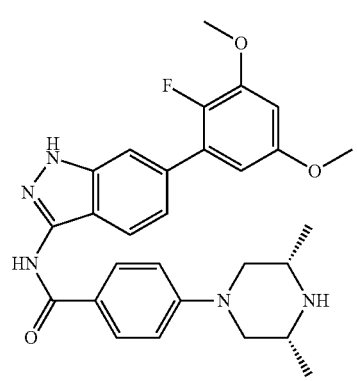 [SMILES: COc1cc(OC)c(F)c(-c2ccc3c(NC(=O)c4ccc(N5C[C@@H](C)N[C@@H](C)C5)cc4)n[nH]c3c2)c1]
TABLE A-continued
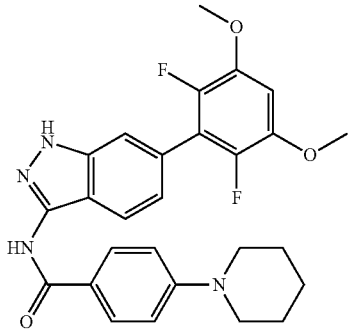 [SMILES: COc1cc(OC)c(F)c(-c2ccc3c(NC(=O)c4ccc(N5CCCCC5)cc4)n[nH]c3c2)c1F]
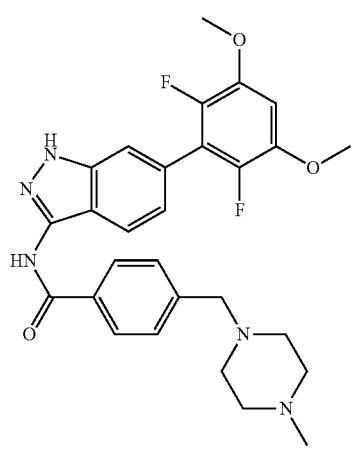 [SMILES: COc1cc(OC)c(F)c(-c2ccc3c(NC(=O)c4ccc(CN5CCN(C)CC5)cc4)n[nH]c3c2)c1F]
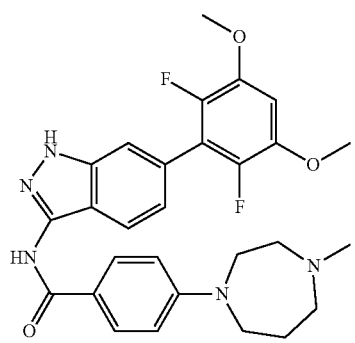 [SMILES: COc1cc(OC)c(F)c(-c2ccc3c(NC(=O)c4ccc(N5CCCN(C)CC5)cc4)n[nH]c3c2)c1F]
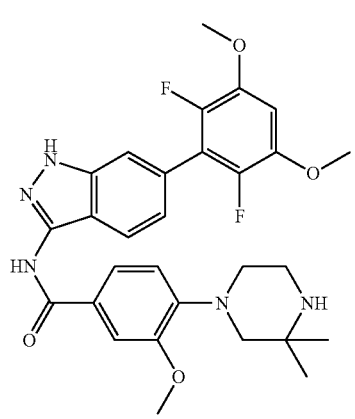 [SMILES: COc1cc(C(=O)Nc2n[nH]c3cc(-c4c(F)c(OC)cc(OC)c4F)ccc23)ccc1N1CCNC(C)(C)C1]

TABLE A-continued
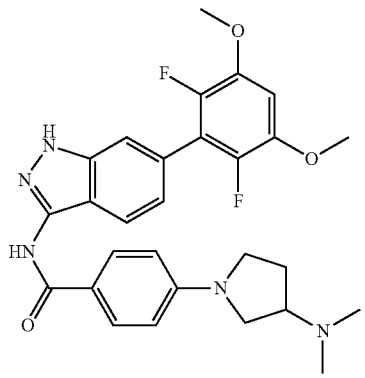 [SMILES: COc1cc(OC)c(F)c(-c2ccc3c(NC(=O)c4ccc(N5CCC(N(C)C)C5)cc4)n[nH]c3c2)c1F]
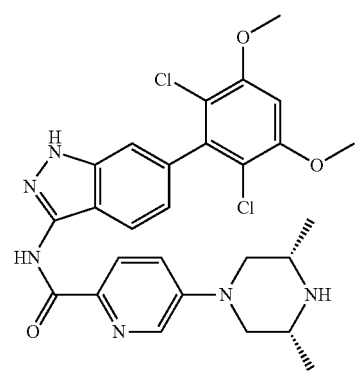 [SMILES: COc1cc(OC)c(Cl)c(-c2ccc3c(NC(=O)c4ccc(N5C[C@@H](C)N[C@@H](C)C5)cn4)n[nH]c3c2)c1Cl]
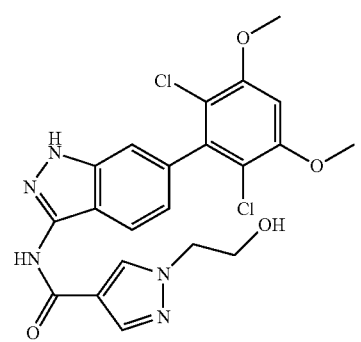 [SMILES: COc1cc(OC)c(Cl)c(-c2ccc3c(NC(=O)c4cnn(CCO)c4)n[nH]c3c2)c1Cl]
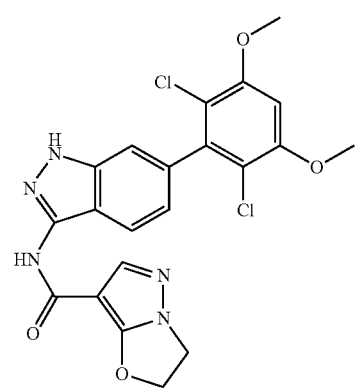 [SMILES: COc1cc(OC)c(Cl)c(-c2ccc3c(NC(=O)c4cnn5c4OCC5)n[nH]c3c2)c1Cl]
TABLE A-continued
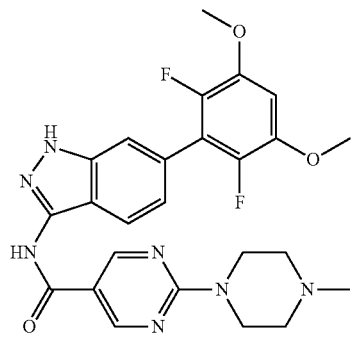 [SMILES: COc1cc(OC)c(F)c(-c2ccc3c(NC(=O)c4cnc(N5CCN(C)CC5)nc4)n[nH]c3c2)c1F]
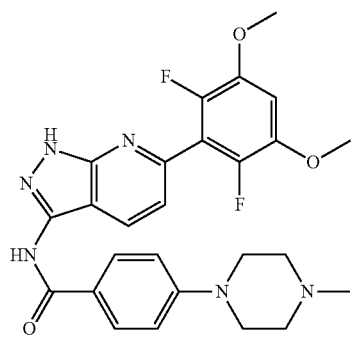 [SMILES: COc1cc(OC)c(F)c(-c2ccc3c(NC(=O)c4ccc(N5CCN(C)CC5)cc4)n[nH]c3n2)c1F]
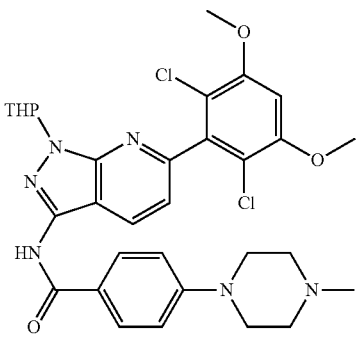
62
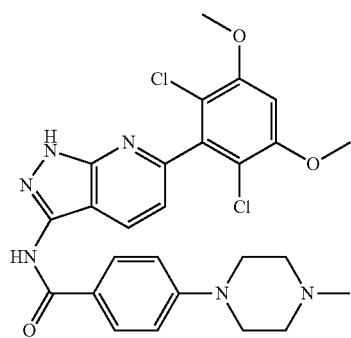
63

TABLE A-continued
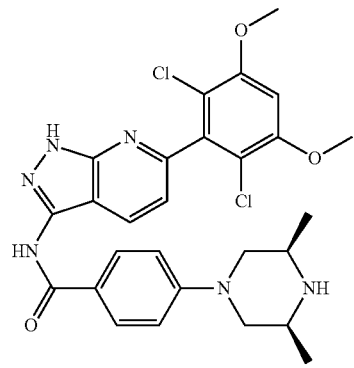 [SMILES: COc1cc(OC)c(Cl)c(-c2ccc3c(NC(=O)c4ccc(N5C[C@@H](C)N[C@@H](C)C5)cc4)n[nH]c3n2)c1Cl]
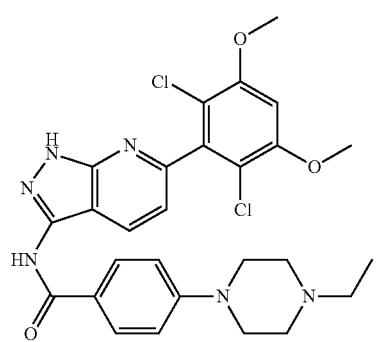 [SMILES: CCN1CCN(c2ccc(C(=O)Nc3n[nH]c4nc(-c5c(Cl)c(OC)cc(OC)c5Cl)ccc34)cc2)CC1]
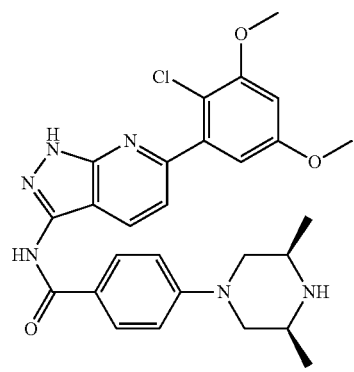 [SMILES: COc1cc(OC)c(Cl)c(-c2ccc3c(NC(=O)c4ccc(N5C[C@@H](C)N[C@@H](C)C5)cc4)n[nH]c3n2)c1]
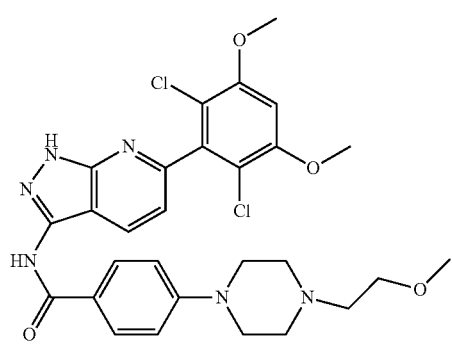 [SMILES: COCCN1CCN(c2ccc(C(=O)Nc3n[nH]c4nc(-c5c(Cl)c(OC)cc(OC)c5Cl)ccc34)cc2)CC1]
TABLE A-continued
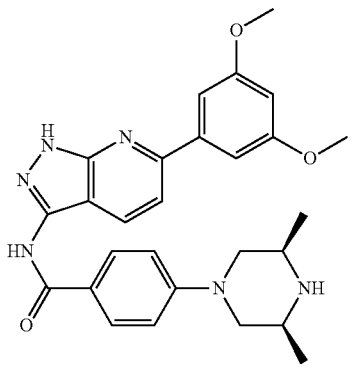 [SMILES: COc1cc(OC)cc(-c2ccc3c(NC(=O)c4ccc(N5C[C@@H](C)N[C@@H](C)C5)cc4)n[nH]c3n2)c1]
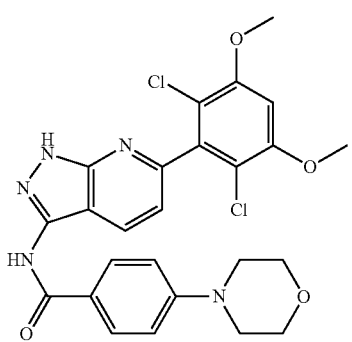 [SMILES: COc1cc(OC)c(Cl)c(-c2ccc3c(NC(=O)c4ccc(N5CCOCC5)cc4)n[nH]c3n2)c1Cl]
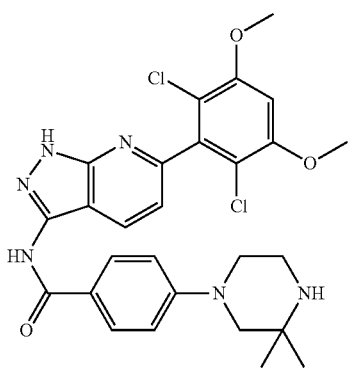 [SMILES: COc1cc(OC)c(Cl)c(-c2ccc3c(NC(=O)c4ccc(N5CCNC(C)(C)C5)cc4)n[nH]c3n2)c1Cl]
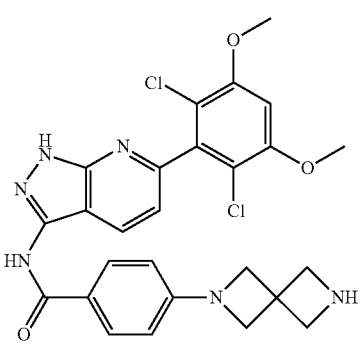 [SMILES: COc1cc(OC)c(Cl)c(-c2ccc3c(NC(=O)c4ccc(N5CC6(CNC6)C5)cc4)n[nH]c3n2)c1Cl]

TABLE A-continued
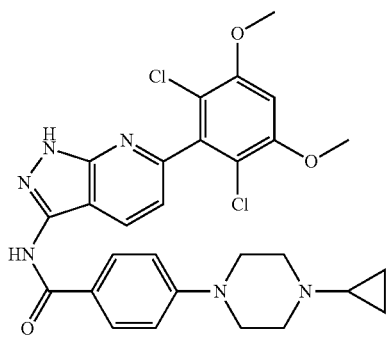 [SMILES: COc1cc(OC)c(Cl)c(-c2ccc3c(NC(=O)c4ccc(N5CCN(C6CC6)CC5)cc4)n[nH]c3n2)c1Cl]
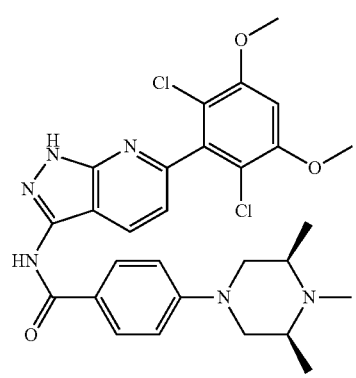 [SMILES: COc1cc(OC)c(Cl)c(-c2ccc3c(NC(=O)c4ccc(N5C[C@@H](C)N(C)[C@@H](C)C5)cc4)n[nH]c3n2)c1Cl]
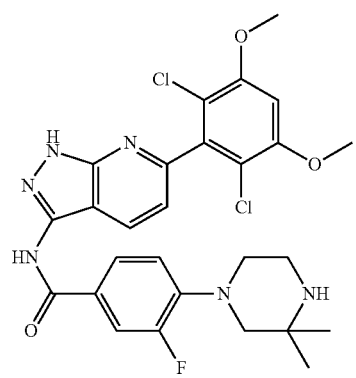 [SMILES: COc1cc(OC)c(Cl)c(-c2ccc3c(NC(=O)c4ccc(N5CCNC(C)(C)C5)c(F)c4)n[nH]c3n2)c1Cl]
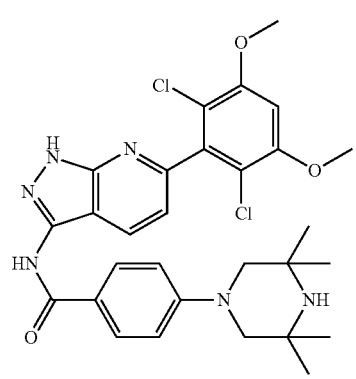 [SMILES: COc1cc(OC)c(Cl)c(-c2ccc3c(NC(=O)c4ccc(N5CC(C)(C)NC(C)(C)C5)cc4)n[nH]c3n2)c1Cl]
TABLE A-continued
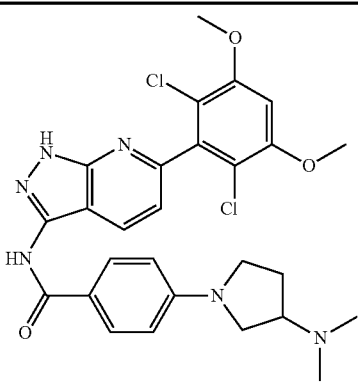
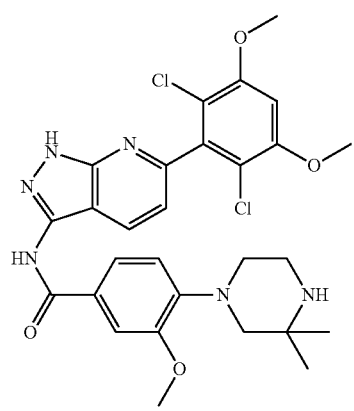 [SMILES: COc1cc(C(=O)Nc2n[nH]c3nc(-c4c(Cl)c(OC)cc(OC)c4Cl)ccc23)ccc1N1CCNC(C)(C)C1]
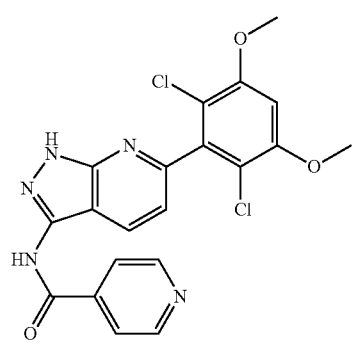 [SMILES: COc1cc(OC)c(Cl)c(-c2ccc3c(NC(=O)c4ccncc4)n[nH]c3n2)c1Cl]
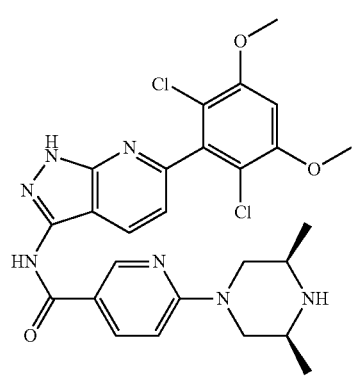 [SMILES: COc1cc(OC)c(Cl)c(-c2ccc3c(NC(=O)c4ccc(N5C[C@@H](C)N[C@@H](C)C5)nc4)n[nH]c3n2)c1Cl]

TABLE A-continued
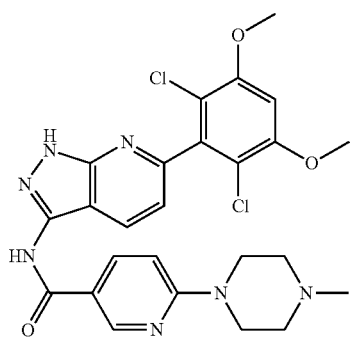 [SMILES: COc1cc(OC)c(Cl)c(-c2ccc3c(NC(=O)c4ccc(N5CCN(C)CC5)nc4)n[nH]c3n2)c1Cl]
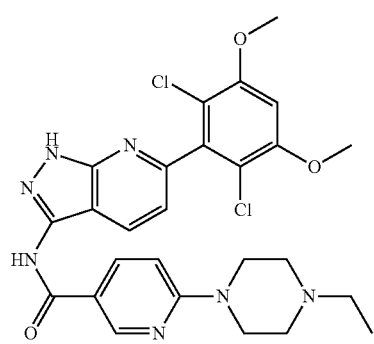 [SMILES: CCN1CCN(c2ccc(C(=O)Nc3n[nH]c4nc(-c5c(Cl)c(OC)cc(OC)c5Cl)ccc34)cn2)CC1]
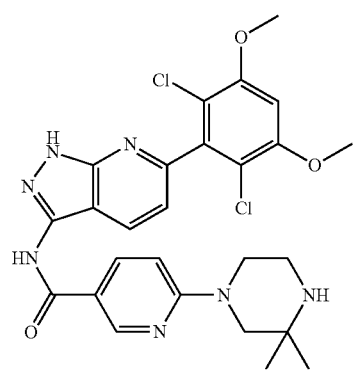 [SMILES: COc1cc(OC)c(Cl)c(-c2ccc3c(NC(=O)c4ccc(N5CCNC(C)(C)C5)nc4)n[nH]c3n2)c1Cl]
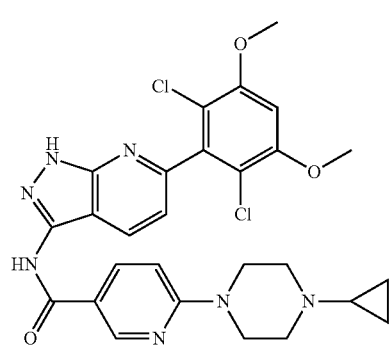 [SMILES: COc1cc(OC)c(Cl)c(-c2ccc3c(NC(=O)c4ccc(N5CCN(C6CC6)CC5)nc4)n[nH]c3n2)c1Cl]
TABLE A-continued
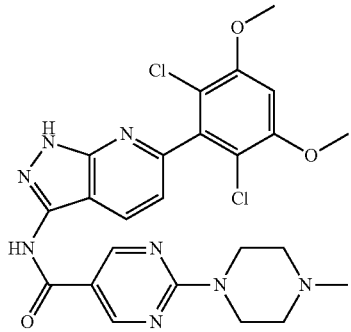 [SMILES: COc1cc(OC)c(Cl)c(-c2ccc3c(NC(=O)c4cnc(N5CCN(C)CC5)nc4)n[nH]c3n2)c1Cl]
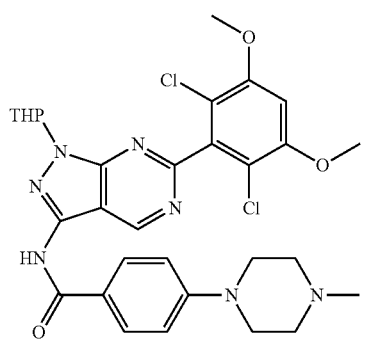
82
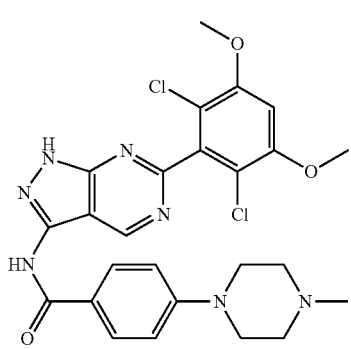 [SMILES: COc1cc(OC)c(Cl)c(-c2ncc3c(NC(=O)c4ccc(N5CCN(C)CC5)cc4)n[nH]c3n2)c1Cl]
83
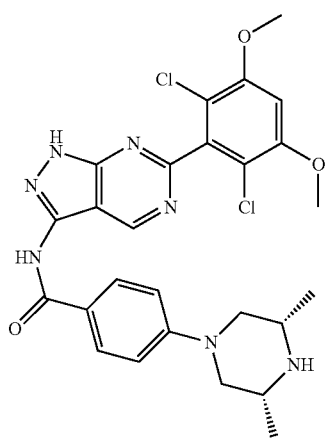 [SMILES: COc1cc(OC)c(Cl)c(-c2ncc3c(NC(=O)c4ccc(N5C[C@@H](C)N[C@@H](C)C5)cc4)n[nH]c3n2)c1Cl]

TABLE A-continued
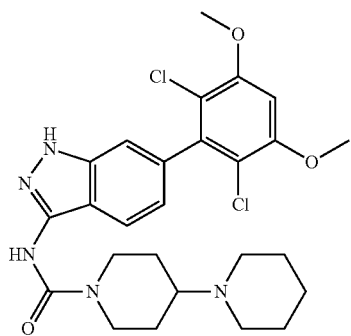 [SMILES: COc1cc(OC)c(Cl)c(-c2ccc3c(NC(=O)N4CCC(N5CCCCC5)CC4)n[nH]c3c2)c1Cl]
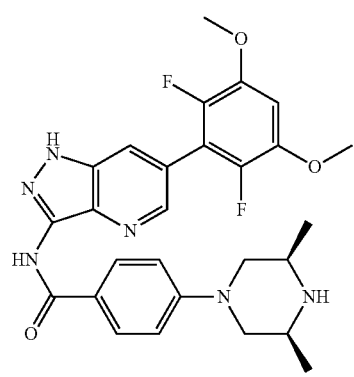 [SMILES: COc1cc(OC)c(F)c(-c2cnc3c(NC(=O)c4ccc(N5C[C@@H](C)N[C@@H](C)C5)cc4)n[nH]c3c2)c1F]
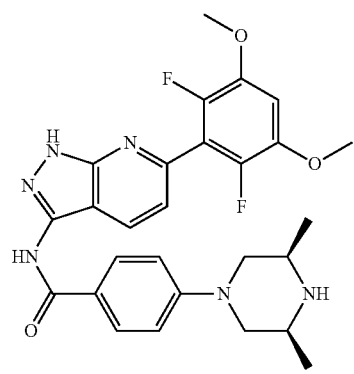 [SMILES: COc1cc(OC)c(F)c(-c2ccc3c(NC(=O)c4ccc(N5C[C@@H](C)N[C@@H](C)C5)cc4)n[nH]c3n2)c1F]
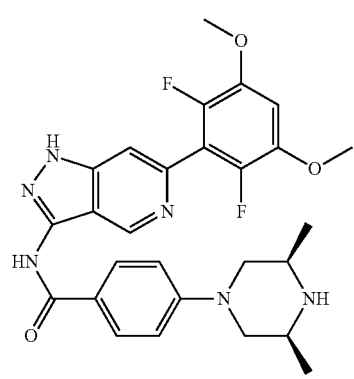 [SMILES: COc1cc(OC)c(F)c(-c2cc3[nH]nc(NC(=O)c4ccc(N5C[C@@H](C)N[C@@H](C)C5)cc4)c3cn2)c1F]
TABLE A-continued
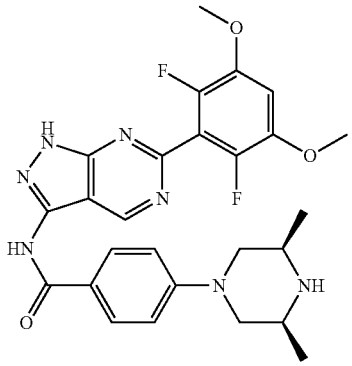 [SMILES: COc1cc(OC)c(F)c(-c2ncc3c(NC(=O)c4ccc(N5C[C@@H](C)N[C@@H](C)C5)cc4)n[nH]c3n2)c1F]
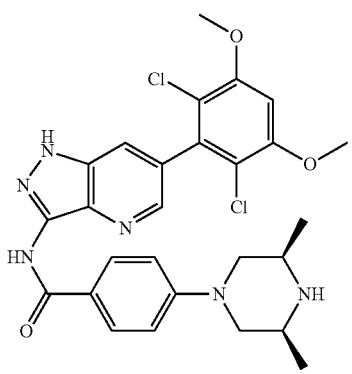 [SMILES: COc1cc(OC)c(Cl)c(-c2cnc3c(NC(=O)c4ccc(N5C[C@@H](C)N[C@@H](C)C5)cc4)n[nH]c3c2)c1Cl]
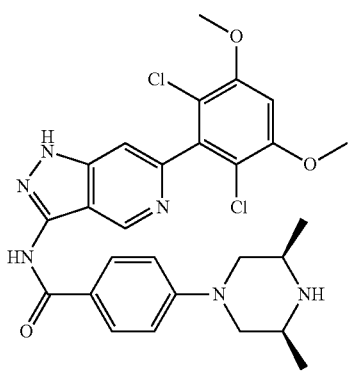 [SMILES: COc1cc(OC)c(Cl)c(-c2cc3[nH]nc(NC(=O)c4ccc(N5C[C@@H](C)N[C@@H](C)C5)cc4)c3cn2)c1Cl]
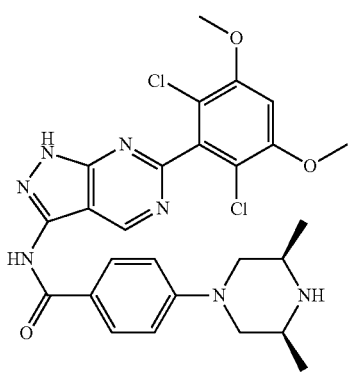 [SMILES: COc1cc(OC)c(Cl)c(-c2ncc3c(NC(=O)c4ccc(N5C[C@@H](C)N[C@@H](C)C5)cc4)n[nH]c3n2)c1Cl]

TABLE A-continued
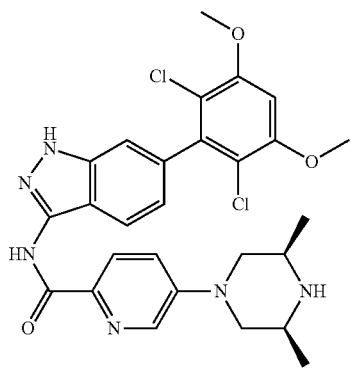 [SMILES: COc1cc(OC)c(Cl)c(-c2ccc3c(NC(=O)c4ccc(N5C[C@@H](C)N[C@@H](C)C5)cn4)n[nH]c3c2)c1Cl]
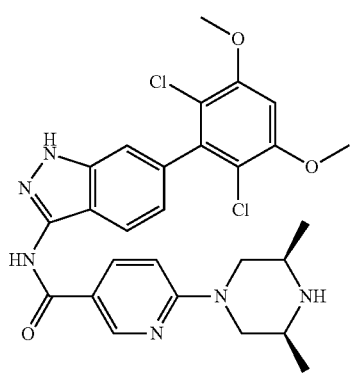 [SMILES: COc1cc(OC)c(Cl)c(-c2ccc3c(NC(=O)c4ccc(N5C[C@@H](C)N[C@@H](C)C5)nc4)n[nH]c3c2)c1Cl]
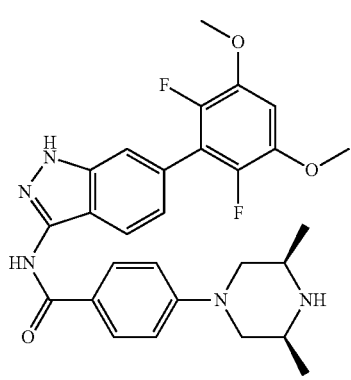 [SMILES: COc1cc(OC)c(F)c(-c2ccc3c(NC(=O)c4ccc(N5C[C@@H](C)N[C@@H](C)C5)cc4)n[nH]c3c2)c1F]
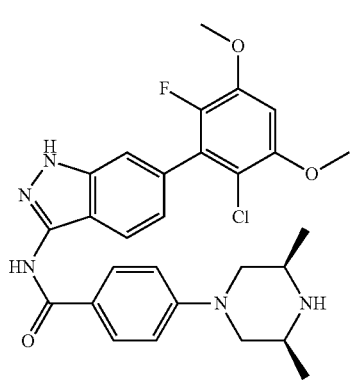 [SMILES: COc1cc(OC)c(Cl)c(-c2ccc3c(NC(=O)c4ccc(N5C[C@@H](C)N[C@@H](C)C5)cc4)n[nH]c3c2)c1F]
TABLE A-continued
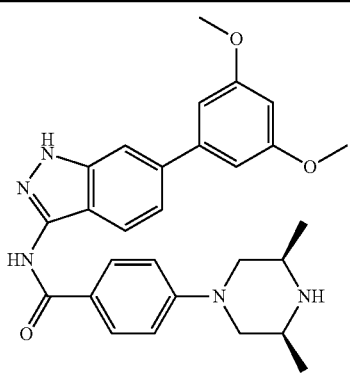
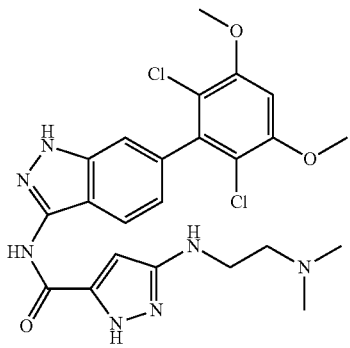 [SMILES: COc1cc(OC)c(Cl)c(-c2ccc3c(NC(=O)c4cc(NCCN(C)C)n[nH]4)n[nH]c3c2)c1Cl]
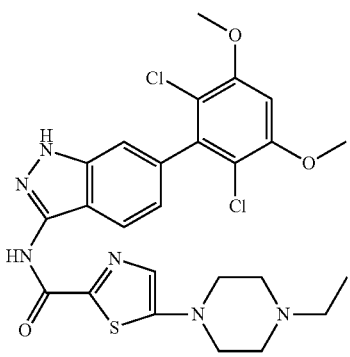 [SMILES: CCN1CCN(c2cnc(C(=O)Nc3n[nH]c4cc(-c5c(Cl)c(OC)cc(OC)c5Cl)ccc34)s2)CC1]
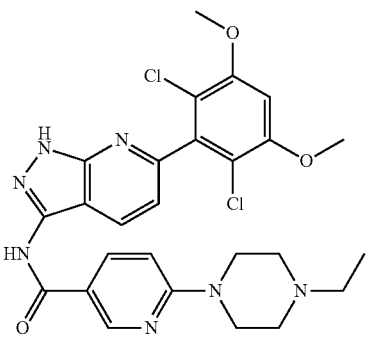
In another preferred embodiment, L, X, W, Y, Z, ring A or R are the corresponding groups in the specific compounds described in the examples.
In the second aspect of the present invention, the preparation method of the compound of the first aspect of the present invention is provided, which comprises the following steps:

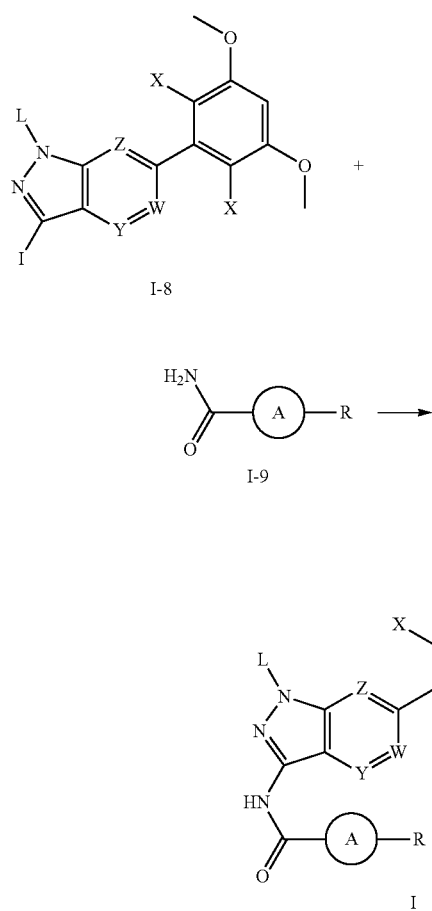

I-8

I-9

I

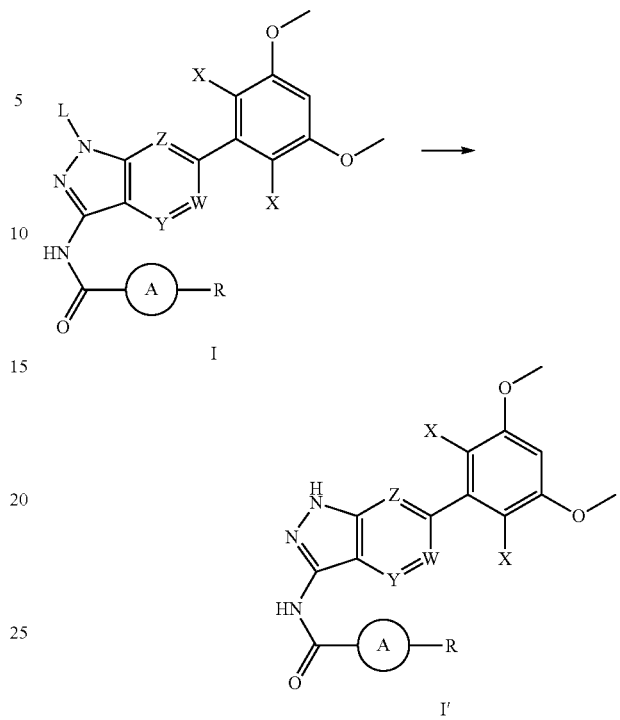

I

I'

(a) In an inert solvent, reacting the compound of formula I-8 with the compound of formula I-9 to obtain the compound of formula I;

wherein the groups in the above formulas are defined as in claim 1.

In another preferred embodiment, in said step (a), the reaction is conducted with the presence of a copper salt; preferably, the copper salt is selected from the group consisting of: CuI, Cu, CuCl, $Cu_2O$, CuO, $Cu(OAc)_2$, $CuSO_4 \cdot 5H_2O$, $Cu(acac)_2$, $CuCl_2$, CuSCN, or a combination thereof.

In another preferred embodiment, in said step (a), said reaction is carried out in the presence of a ligand; preferably, said ligand is a bidentate amine ligand; more preferably, the ligand is selected from the group consisting of: N1, N2-dimethyl-ethylenediamine, (1R, 2R)-(−)-N, N'-dimethyl-1,2-cyclohexanediamine, or a combination thereof.

In another preferred embodiment, in said step (a), said reaction is carried out in the presence of a base; preferably said base is an inorganic base, more preferably said base is selected from the group consisting of: $K_2CO_3$, $K_3PO_4$, $Cs_2CO_3$, or a combination thereof.

In another preferred embodiment, the inert solvent is selected from the group consisting of: toluene, dioxane, THF, DMF, or a combination thereof.

In another preferred embodiment, the method further comprises the following steps:

(b) deprotecting the compound of formula I in an inert solvent to give a compound of formula I';

wherein L is selected from the group consisting of: tetrahydropyranyl (THP);

while the other groups are defined as above.

In another preferred embodiment, in step (b), the reaction is carried out in the presence of an acid; preferably, said acid is selected from the group consisting of: hydrochloric acid, p-toluenesulfonic acid, TFA, or a combination thereof.

In another preferred embodiment, in step (b), the inert solvent is selected from the group consisting of: dichloromethane, methanol, ethanol, isopropanol, n-butanol, t-butanol, isobutanol, or a combination thereof.

In the third aspect of the present invention, use of the compound of the first aspect of the present invention is provided, wherein the use is for:

(a) manufacture of a medicament for treating diseases associated with FGFR kinase activity or expression amount;

(b) manufacture of FGFR kinase targeting inhibitors;

(c) in vitro non-therapeutic inhibition of FGFR kinase activity;

(d) in vitro non-therapeutic inhibition of tumor cell proliferation; and/or (e) treatment of diseases associated with FGFR kinase activity or expression amount.

In another preferred embodiment, the disease associated with FGFR activity or expression amount is tumor, preferably tumor selected from the group consisting of: endometrial cancer, breast cancer, stomach cancer, bladder cancer, myeloma, liver cancer.

In another preferred embodiment, the FGFR kinase is selected from the group consisting of: FGFR1, FGFR2, FGFR3, or a combination thereof.

In another preferred embodiment, the tumor cell is a leukemia cell strain; preferably myelogenous leukemia cell strain; more preferably acute myelogenous leukemia cell strain KG1.

In the fourth aspect of the present invention, a pharmaceutical composition is provided, wherein the pharmaceutical composition comprises: (i) an effective amount of the compound of formula I, or a pharmaceutically acceptable salt thereof, and (ii) a pharmaceutically acceptable carrier.

In another preferred embodiment, the effective amount means a therapeutically or inhibitory effective amount, preferably from 0.01 to 99.99%.

In another preferred embodiment, the pharmaceutical composition is used to inhibit the FGFR kinase activity.

In another preferred embodiment, the pharmaceutical composition is used to treat a disease associated with FGFR kinase activity or expression amount.

In the fifth aspect of the present invention, a method for inhibiting FGFR kinase activity is provided, wherein the method comprises the following step: administering an inhibitory effective amount of the compound of formula I according to the first aspect of the invention or a pharmaceutically acceptable salt thereof to a subject in need of inhibition, or administering an inhibitory effective amount of the pharmaceutical composition according to the fourth aspect of the invention to a subject in need of inhibition.

In another preferred embodiment, the inhibition is in vitro non-therapeutic inhibition.

In another preferred embodiment, the inhibitory effective amount is from 0.001 to 500 nmol/L, preferably 0.01 to 200 nmol/L when an inhibitory effective amount of the compound of formula I according to claim 1 or a pharmaceutically acceptable salt thereof is administered to a subject in need of inhibition.

In the sixth aspect of the present invention, a method for treating a disease associated with FGFR kinase activity or expression amount is provided, wherein the method comprises: administering to the subject in need of treatment a therapeutically effective amount of the compound of formula I as described in the first aspect of the invention, or the pharmaceutical composition as described in the fourth aspect of the invention.

In another preferred embodiment, the disease associated with FGFR activity or expression amount is tumor, preferably tumor selected from the group consisting of: endometrial cancer, breast cancer, stomach cancer, bladder cancer, myeloma, liver cancer.

In the seventh aspect of the present invention, a method for inhibiting tumor cells in vitro is provided, wherein the method comprises: administering to a subject in need of inhibition an inhibitory effective amount of the compound of formula I as described in the first aspect of the invention, or the pharmaceutical composition of the fourth aspect of the invention.

It should be understood that, in the scope of the present invention, each of the technical features specifically described above and below (such as those in the Examples) can be combined with each other, thereby constituting new or preferred technical solutions which need not be specified herein for the sake of brevity.

EMBODIMENTS FOR CARRYING OUT THE INVENTION

Through long and intensive studies, the inventors have prepared a class of compounds having the structure of formula I, and found that they have FGFR kinase inhibitory activity. The compounds have inhibitory activity against a series of FGFR kinases at very low concentrations (as low as ≤100 nmol/L), thus showing excellent inhibitory activity and can be used for the treatment of diseases associated with FGFR kinase activity or expression level, such as tumors. The present invention was thus completed on this basis.

Terms

As used herein, the term "C1-C6 alkyl" refers to linear or branched alkyl with 1 to 6 carbon atoms, such as methyl, ethyl, propyl, isopropyl, butyl, isobutyl, sec-butyl, tert-butyl, or the like.

The term "C1-C6 alkylene" refers to groups formed by C1-C6 alkyl as described above losing one hydrogen atom, such as —CH$_2$—, —CH$_2$—CH$_2$—, or the like.

The term "C6-C10 arylene" refers to groups formed by losing one hydrogen atom in aryls with 6-10 carbon atoms, such as monocyclic or bicyclic arylene, such as phenylene, naphthylene, or the like.

The term "six-membered aryl group" means phenyl.

The term "5 to 8-membered aryl" refers to a 5-8 membered unsaturated carbocyclic ring substituent, such as phenyl, or the like.

The term "5 to 8-membered heteroaryl" refers to a 5-8 membered unsaturated ring system substituent having one or more hetero atoms selected from O, S, N or P, such as pyridyl, thienyl, or the like.

The term "saturated 3 to 12 membered carbocyclic ring" means a saturated carbocyclic rings having 3 to 12 carbon atoms, e.g., cyclohexyl, or the like.

The term "3 to 12-membered heterocyclic ring" refers to a 3-12 membered saturated ring system substituent having one or more hetero atoms selected from O, S, N or P, such as piperidinyl, pyrrolyl, or the like.

The term "halogen" refers to F, Cl, Br and me.

In the present invention, the term "comprise", "contain" or "include" means that the various components can be used together in the mixture or composition of the present invention. Therefore, the phrases "mainly consist of" and "consist of" are encompassed by the term "comprise".

In the present invention, the term "pharmaceutically acceptable" component refers to substances which are suitable for applying to humans and/or animals without undue harmful side reactions (such as toxicity, stimulation or allergy), that is to say, substances of reasonable benefit/risk ratio.

In the present invention, the term "effective amount" refers to an amount with which a therapeutic agent can treat, relieve or prevent the targeted disease or condition, or exhibit detectable treatment or prevention effects. The exact effective amount for a certain subject will depend on the size and health condition of the subject, the nature and extent of the disorder, and the therapeutic agent and/or therapeutic agent combination selected for administration. Therefore, it is useless to specify an accurate effective amount in advance. However, for a given situation, the effective amount can be determined by routine experimentation, which is within the reasonable judgment of clinicians.

In the present invention, unless otherwise indicated, the term "substituted" means that one or more hydrogen atoms on the group are substituted with a substituent selected from the group consisting of: halogen, unsubstituted or halogenated C1-C6 alkyl, unsubstituted or halogenated C2-C6 acyl group, unsubstituted or halogenated C1-C6 alkyl-hydroxy.

Unless otherwise indicated, all compounds in the invention are intended to include all the possible optical isomers, such as single chiral compounds, or a mixture of various chiral compounds (i.e., racemate). In the compounds of the present invention, each chiral carbon atom may optionally have R configuration or S configuration, or the mixture of R configuration and S configuration.

As used herein, the term "the compound of the invention" refers to the compound of formula I. The term also comprises various crystal forms, pharmaceutically acceptable salts, hydrates or solvates of the compound of formula I.

As used herein, the term "pharmaceutically acceptable salt" refers to a salt suitable for use as a medicament which is formed by the compound of the present invention with an acid or base. The pharmaceutically acceptable salts include inorganic and organic salts. A preferred type of salts are salts formed by the compounds of the present invention with acids. Suitable salt-forming acids include, but are not limited to: inorganic acids such as hydrochloric acid, hydrobromic acid, hydrofluoric acid, sulfuric acid, nitric acid, phosphoric acid; organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, toluenesulfonic acid, benzenesulfonic acid and the like; and acidic amino acids such as aspartic acid, and glutamic acid.

Compound of Formula I
wherein:

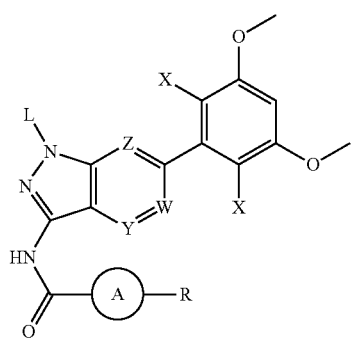

L is selected from the group consisting of: H, tetrahydropyranyl (THP);

each X is independently selected from the group consisting of: Cl, F, H, and CN;

W, Y, and Z are each independently selected from: N or CH;

ring A is absent, unsubstituted or substituted 5- to 8-membered aryl group, or a unsubstituted or substituted 5- to 8-membered heteroaryl group, wherein the heteroaryl group contains at least one heteroatom selected from the group consisting of nitrogen, oxygen, or sulfur; unsubstituted or substituted 3- to 12-membered saturated heterocyclic ring or carbocyclic ring, wherein the heterocyclic ring contains at least one heteroatom selected from the group consisting of nitrogen, oxygen, or sulfur; or

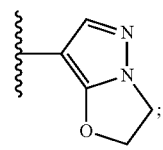 [SMILES: *c1cnn2c1OCC2]

R is H or a substituted or unsubstituted group selected from the group consisting of:

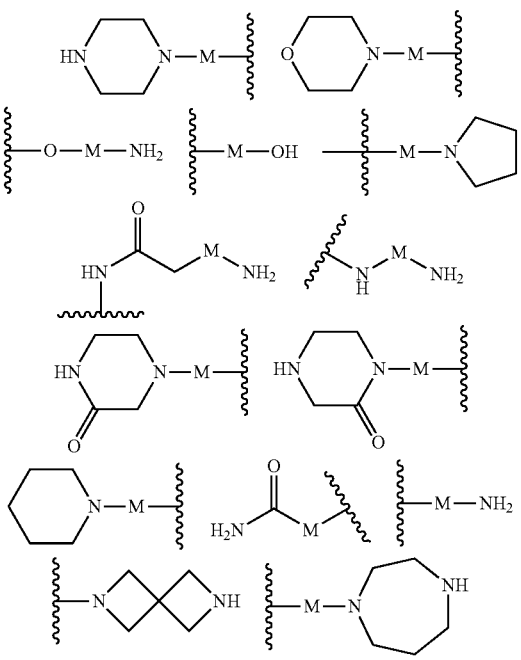

wherein M is selected from the group consisting of: none, substituted or unsubstituted C1-C6 alkylene, substituted or unsubstituted C6-C10 arylene, substituted or unsubstituted C1-C10 heteroarylene;

wherein the term "substituted" means that one or more hydrogen atoms on the group are substituted with substituents selected from the group consisting of: halogen, unsubstituted or halogenated C1-C6 alkyl, unsubstituted or halogenated C2-C6 acyl group, unsubstituted or halogenated C1-C6 alkyl-hydroxy.

In another preferred embodiment, ring A is a heteroaryl group selected from the group consisting of:

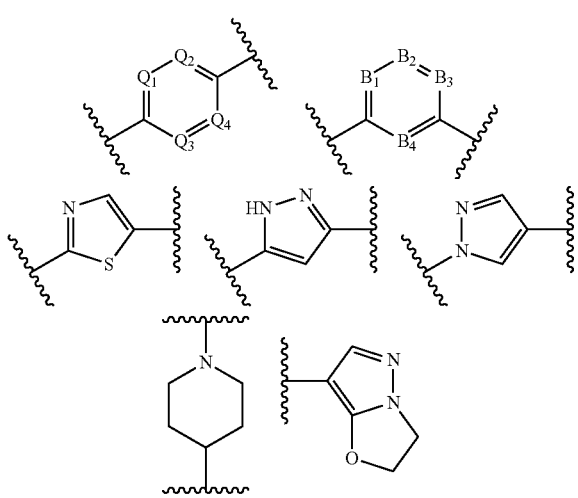

wherein, $Q_1$, $Q_2$, $Q_3$ and $Q_4$ are each independently selected from: N or CH;

$B_1$, $B_2$, $B_3$ and $B_4$ are each independently selected from: N or CH.

In another preferred embodiment, ring A is a heteroaryl group selected from the group consisting of:

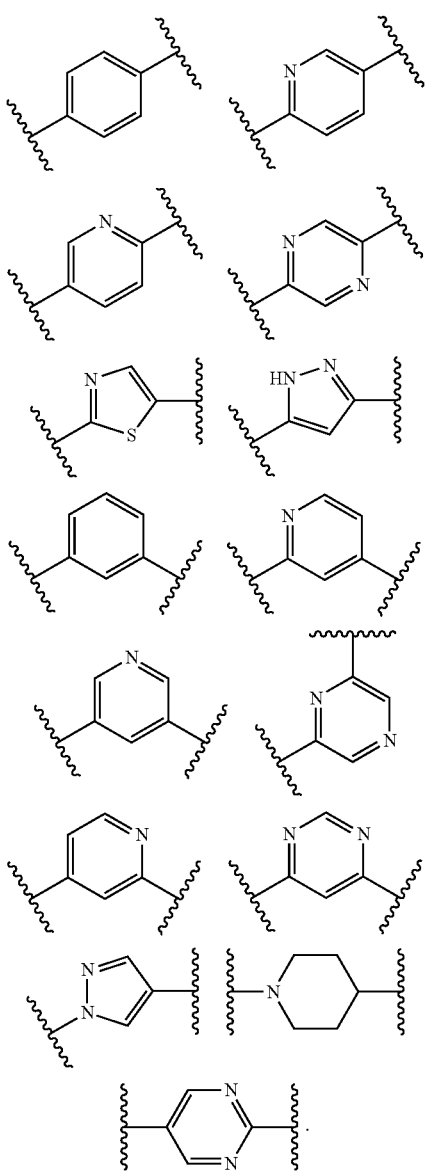

In another preferred embodiment, R is a substituted or unsubstituted group selected from the group consisting of:

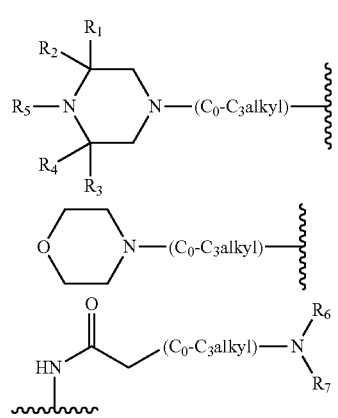

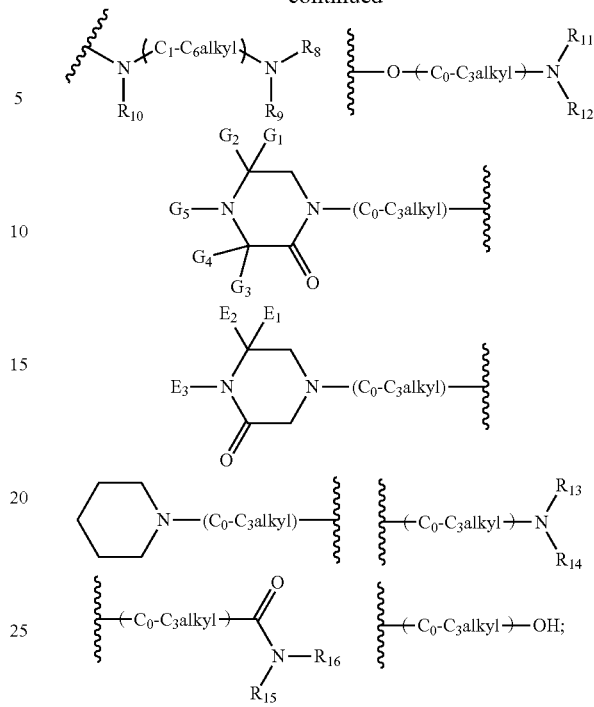

wherein:

$R_1$, $R_2$, $R_3$, $R_4$ are each independently selected from the group consisting of: H, halogen, C1-C6 linear or branched alkyl, halogenated C1-C6 linear or branched alkyl;

$R_5$ is selected from the group consisting of: H, C1-C6 linear or branched alkyl, C1-C6 linear or branched acyl, C1-C6 linear or branched alkylene-hydroxy.

$R_6$, $R_7$, $R_8$, $R_9$, $R_{10}$, $R_{11}$, $R_{12}$ are each independently selected from the group consisting of: H, C1-C6 linear or branched alkyl, C1-C6 linear or branched acyl group, C1-C6 linear or branched alcohol group (alkylene-hydroxy);

$G_1$, $G_2$, $G_3$, $G_4$ are each independently selected from the group consisting of: H, halogen, C1-C6 linear or branched alkyl, halogenated C1-C6 linear or branched alkyl, or $G_5$ is selected from the group consisting of: H, C1-C6 linear or branched alkyl, C1-C6 linear or branched acyl, C1-C6 linear or branched alkyl-hydroxy;

$E_1$, $E_2$ are each independently selected from the group consisting of: H, halogen, linear or branched alkyl, halogenated C1-C6 linear or branched alkyl;

$E_3$ is selected from the group consisting of: H, C1-C6 linear or branched alkyl, C1-C6 linear or branched acyl, C1-C6 linear or branched alkylene-hydroxy;

$R_{13}$, $R_{14}$, $R_{15}$ and $R_{16}$ are each independently selected from the group consisting of: H, C1-C6 linear or branched alkyl, C1-C6 linear or branched acyl group, C1-C6 linear or branched alcohol group (alkylene-hydroxy);

C0-C3 alkyl means absent, or alkylene with 1-3 carbon atoms;

C1-C6 alkyl is alkylene with 1-6 carbon atoms;

In another preferred embodiment, L is selected from the group consisting of: H, tetrahydropyranyl (THP);

each X is independently selected from the group consisting of: H, Cl, F, and CN;

W, Y, and Z are each independently selected from: N or CH;

ring A is unsubstituted or substituted 6-membered aryl group, or unsubstituted or substituted 5- to 6-membered heteroaryl group, wherein the heteroaryl group contains at least one heteroatom selected from the group consisting of nitrogen, oxygen, or sulfur;

M is selected from the group consisting of: unsubstituted or substituted C1-C4 alkylene group, or M is absent;

wherein the term "substituted" means that one or more hydrogen atoms on the group are substituted with substituents selected from the group consisting of: halogen, unsubstituted or halogenated C1-C4 alkyl, unsubstituted or halogenated C2-C4 acyl group, unsubstituted or halogenated C1-C4 alkyl-hydroxy.

In another preferred embodiment, L is H;

each X are independently selected from the group consisting of: H, Cl, and F;

W, Y, and Z are each independently selected from: N or CH;

ring A is a group selected from the group consisting of: none, phenyl, pyrazolyl, pyridyl, thiazolyl, or piperidinyl;

M is selected from the group consisting of: unsubstituted or substituted C1-C3 alkylene group, or M is absent;

wherein the term "substituted" means that one or more hydrogen atoms on the group are substituted with substituents selected from the group consisting of: halogen, unsubstituted or halogenated C1-C4 alkyl, unsubstituted or halogenated C2-C4 acyl group, unsubstituted or halogenated C1-C4 alkyl-hydroxy.

In another preferred embodiment, the compound of formula I is selected from the group consisting of:

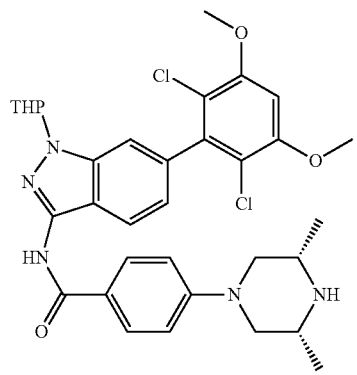

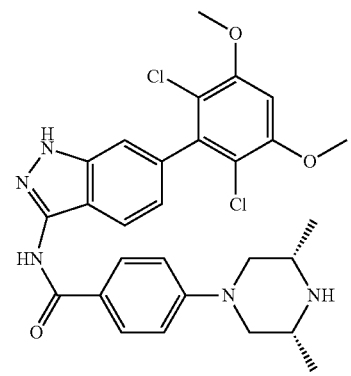

-continued

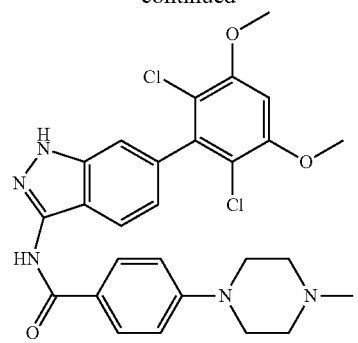

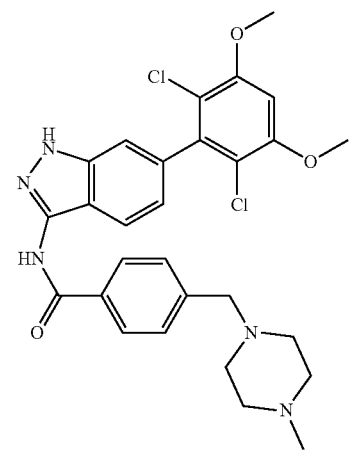

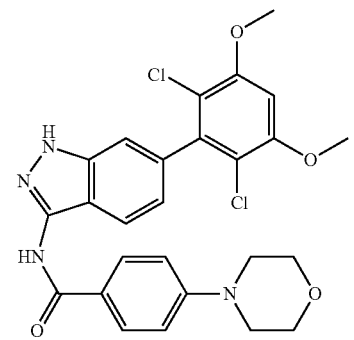

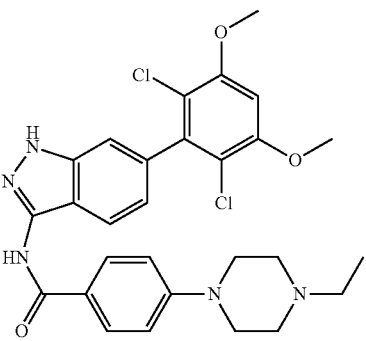

-continued
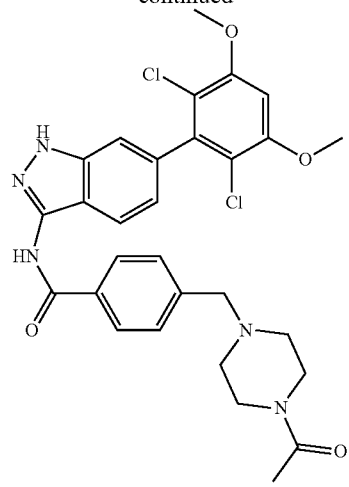
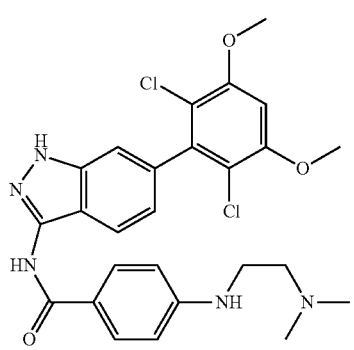
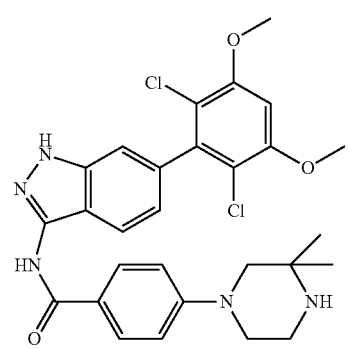
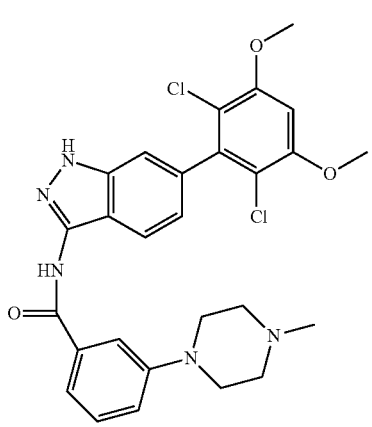
-continued
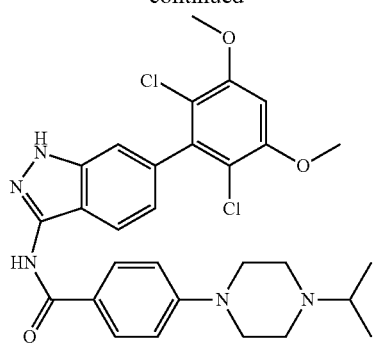
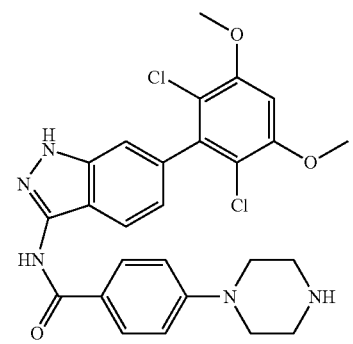
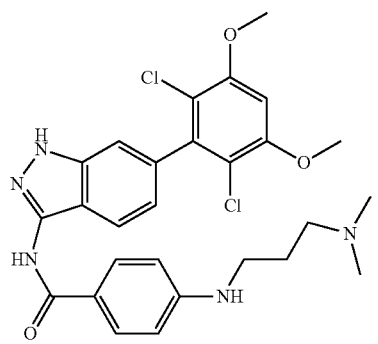
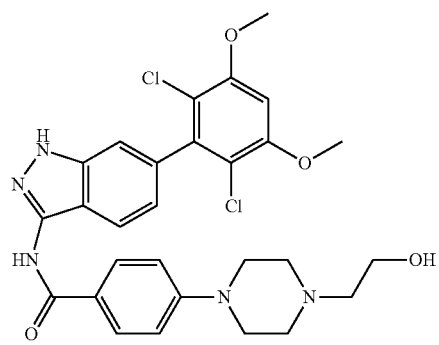
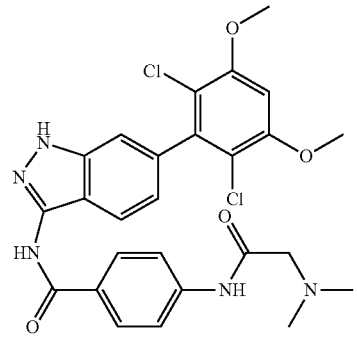

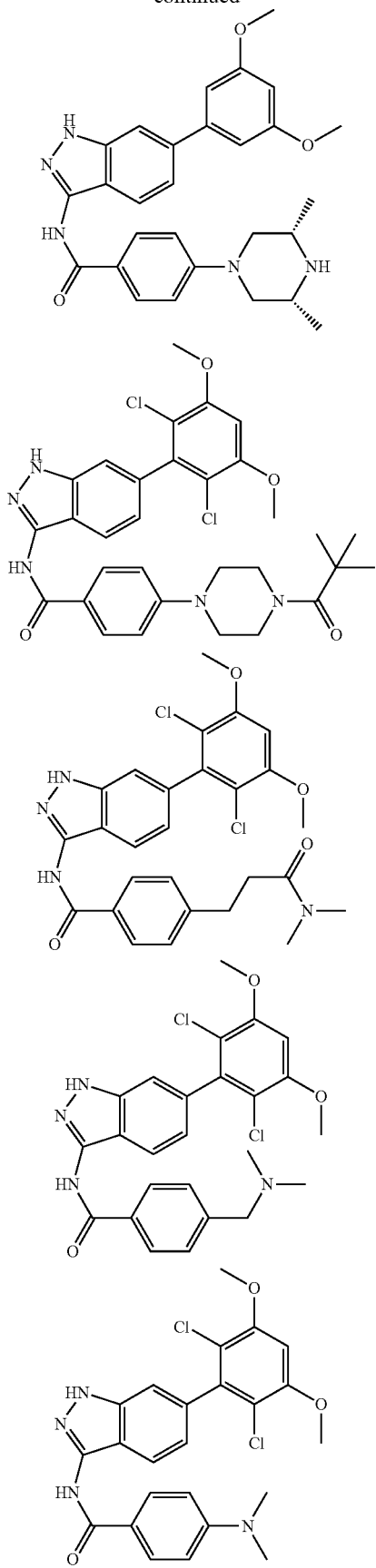
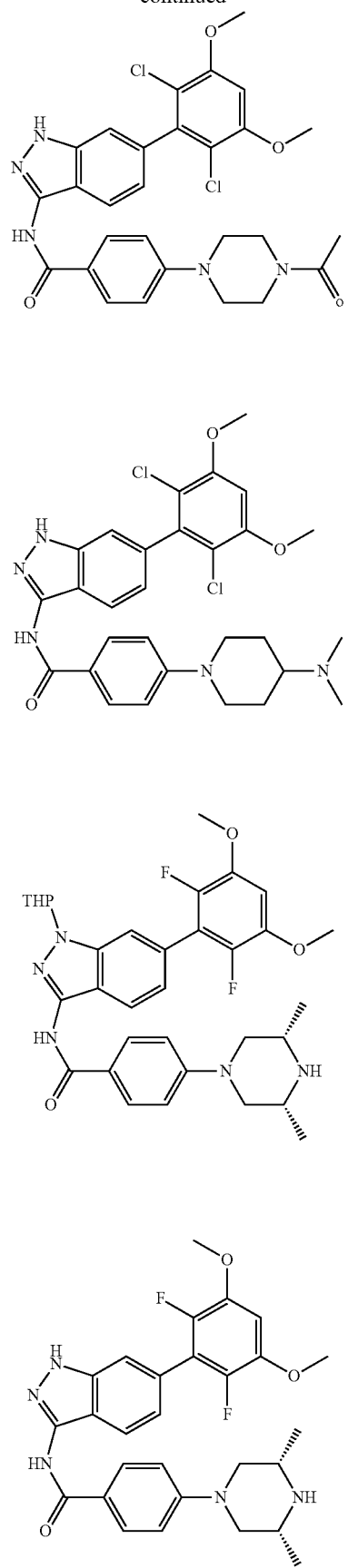

-continued
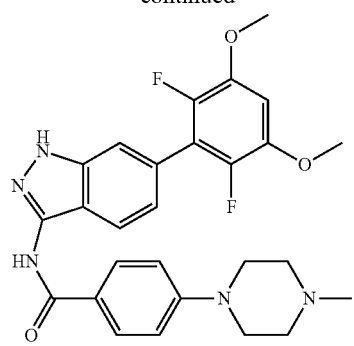
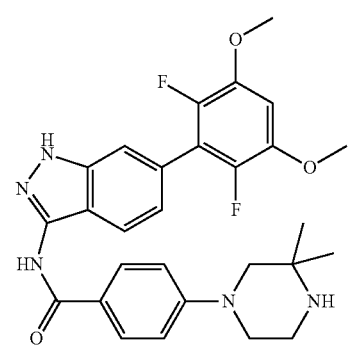
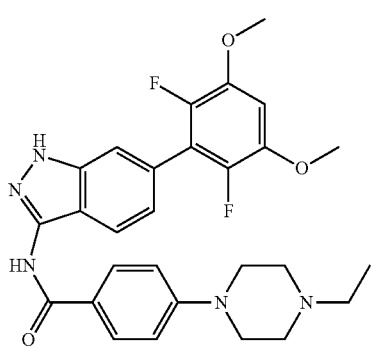
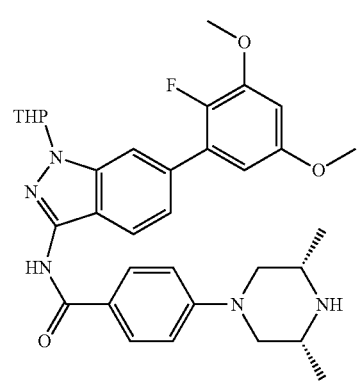
54
-continued
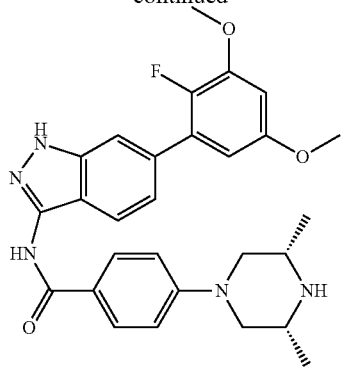
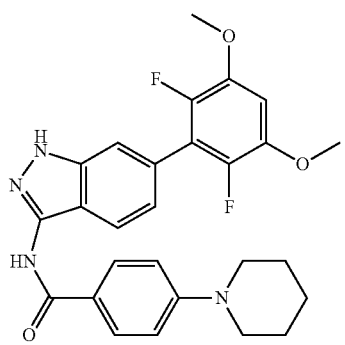
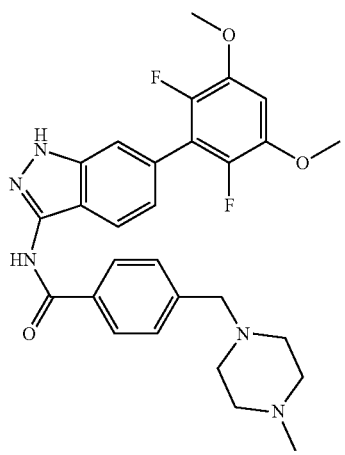
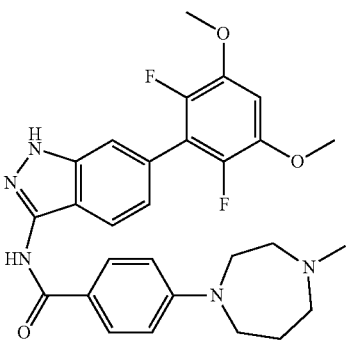

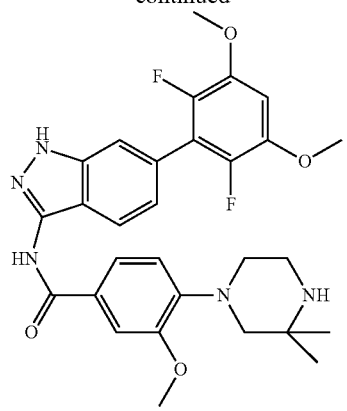
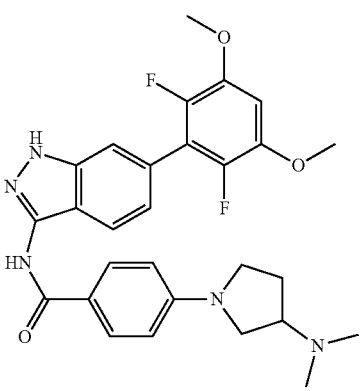
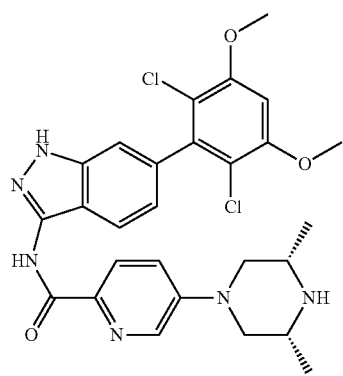
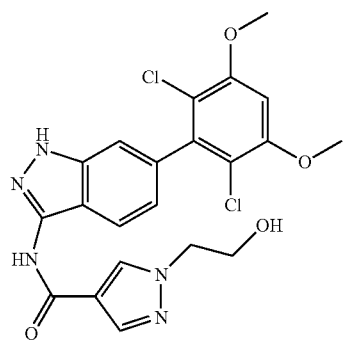
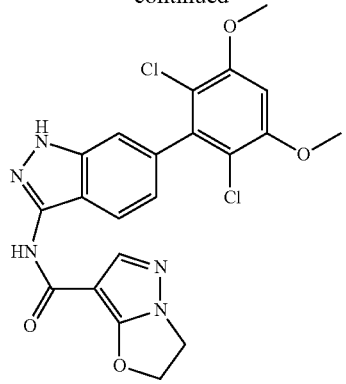
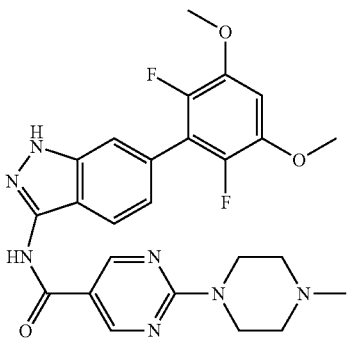
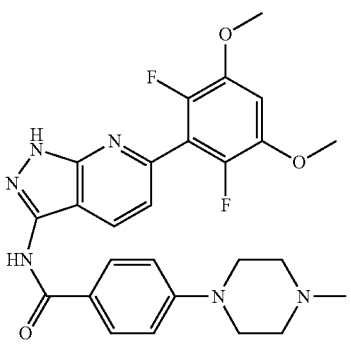
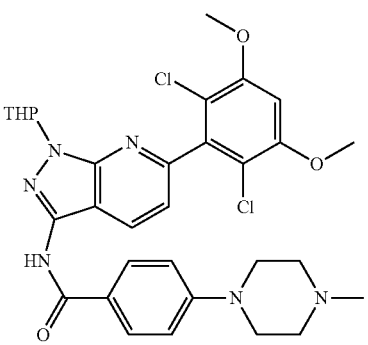

-continued
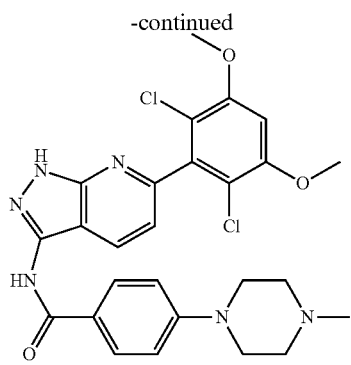
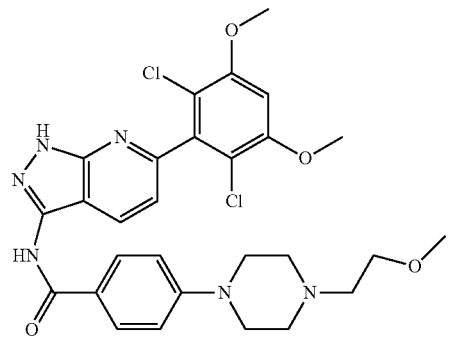
63
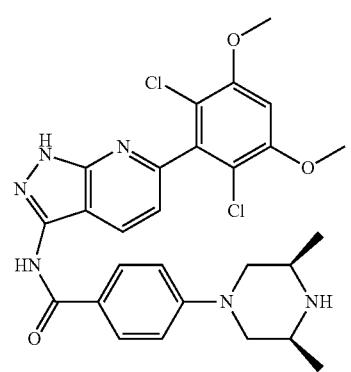
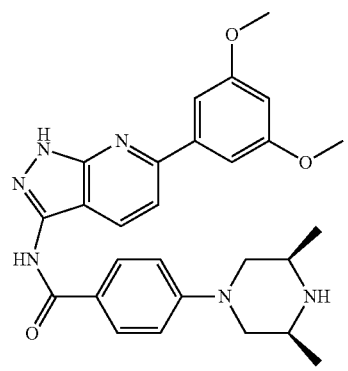
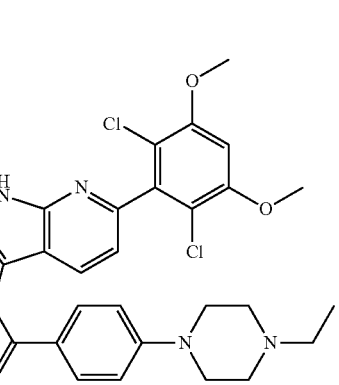
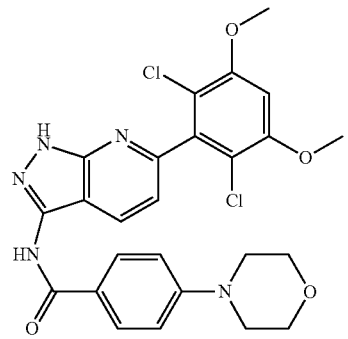
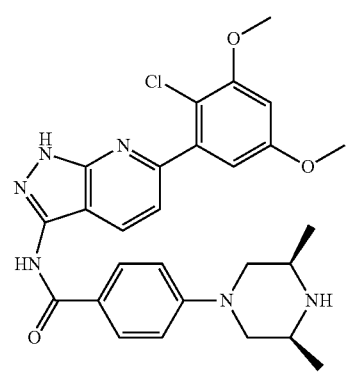
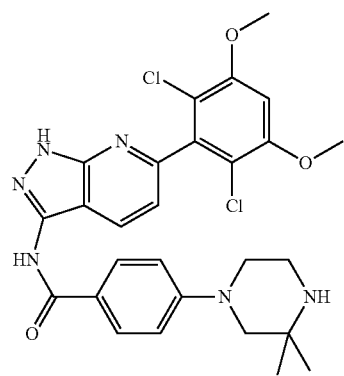

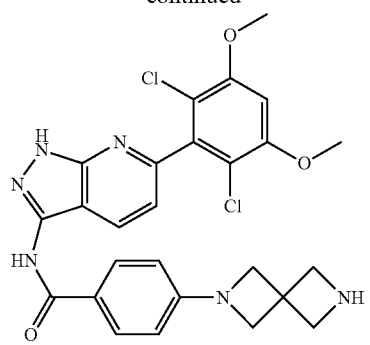
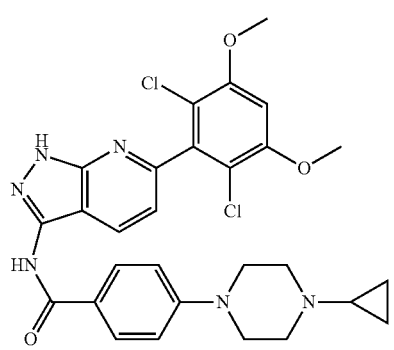
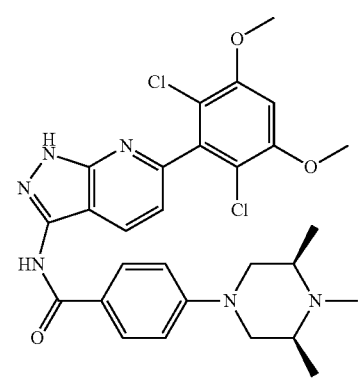
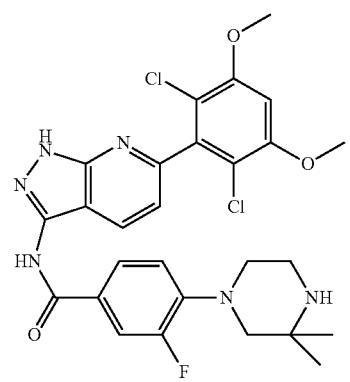
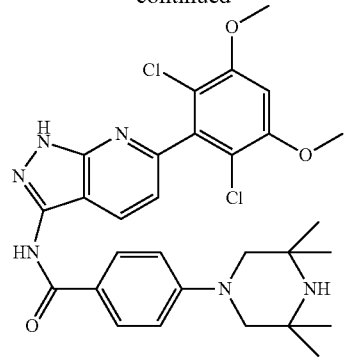
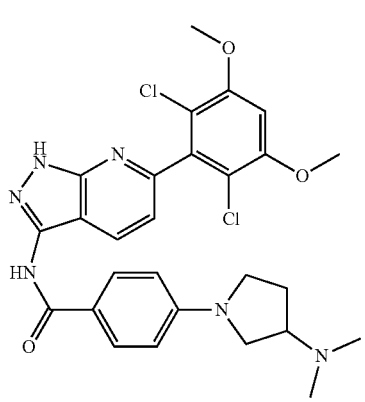
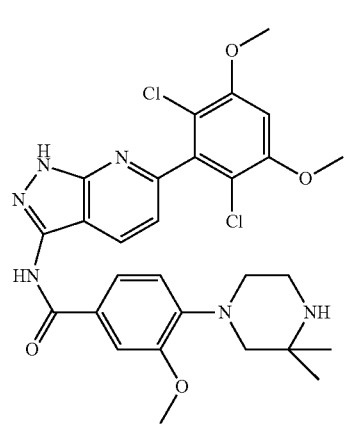
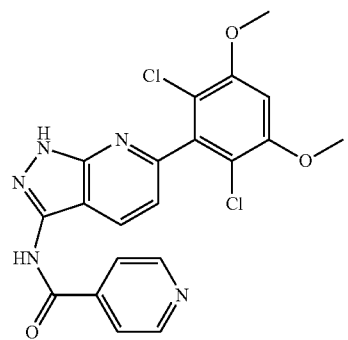

51
-continued
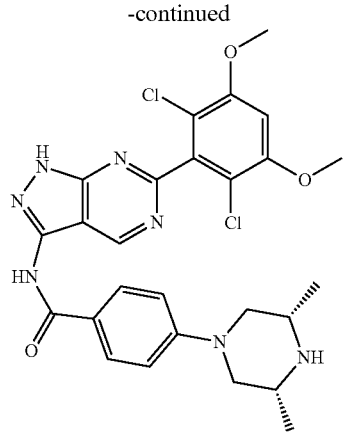
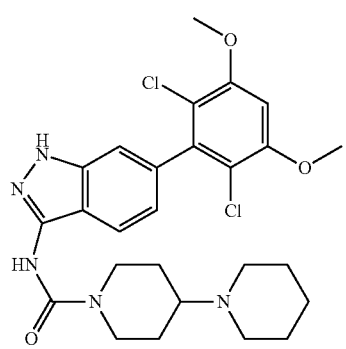
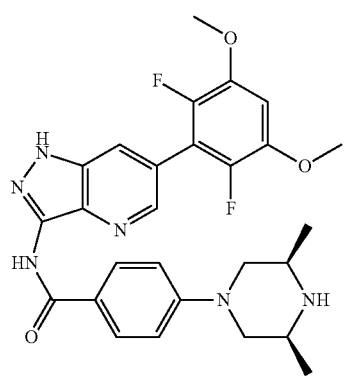
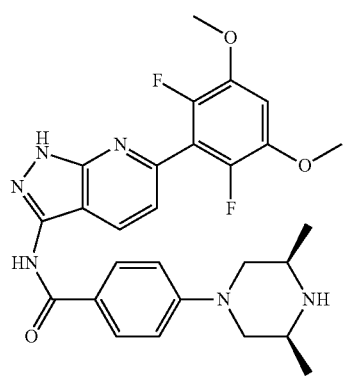
52
-continued
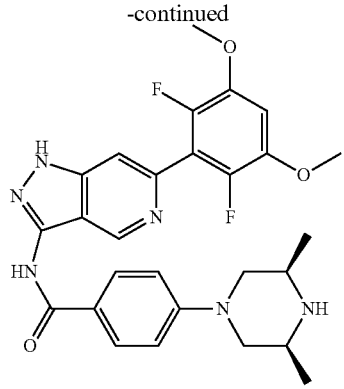
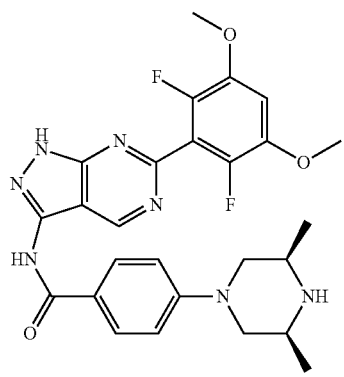
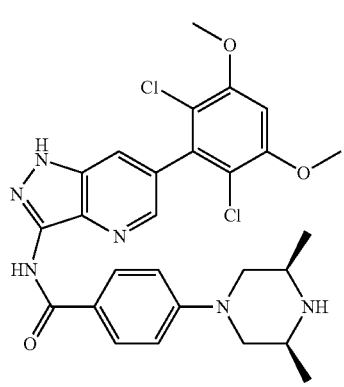
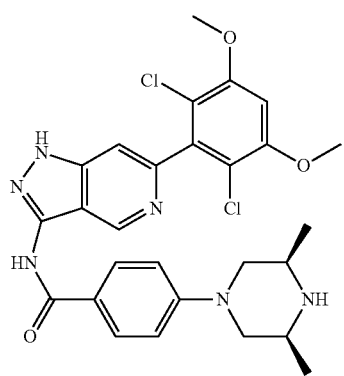

-continued
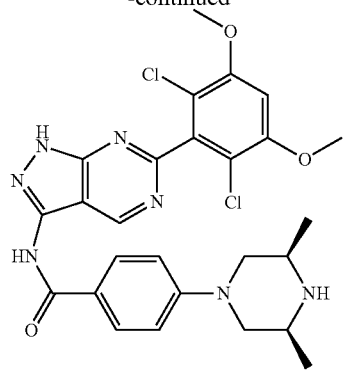
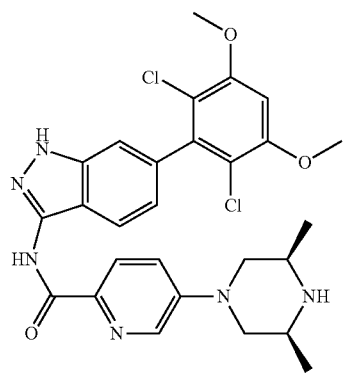
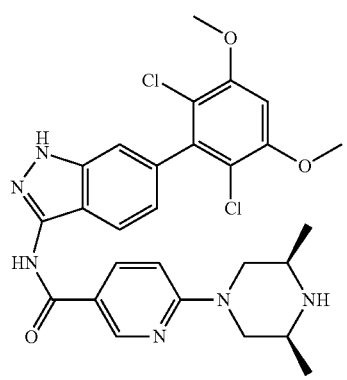
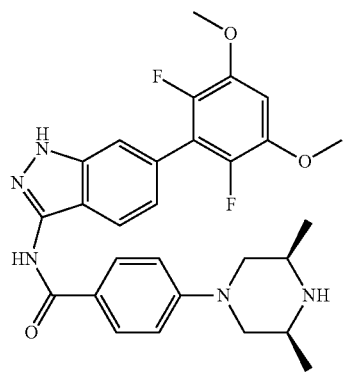
-continued
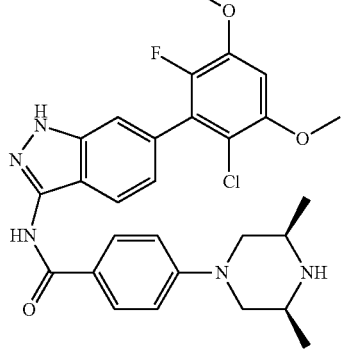
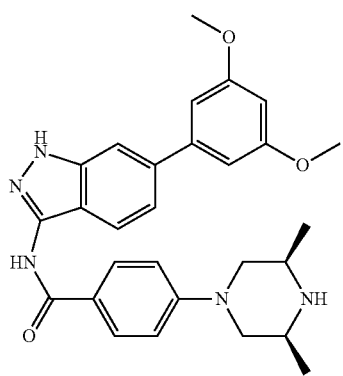
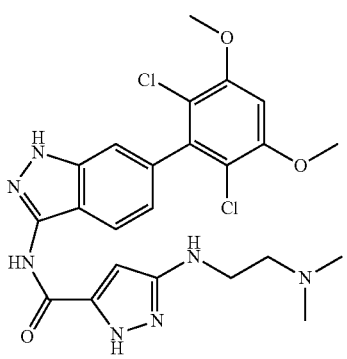
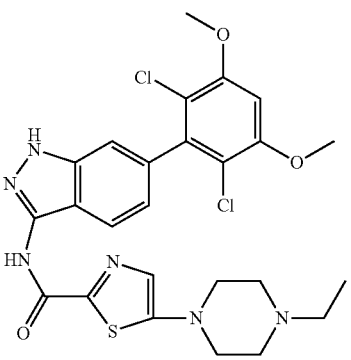

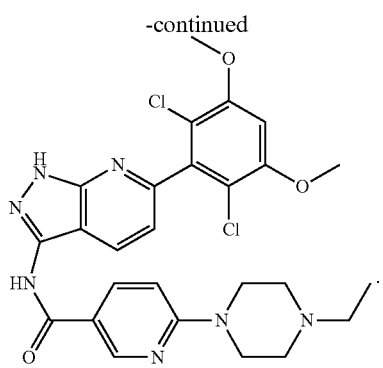

Preparation of the Compounds of Formula I

Preparation Method

Hereinafter more specifically describes the preparation methods of the compounds of formula (I), but such specific methods do not constitute any limitation to the present invention. The compounds of the invention may also be easily prepared by optionally combining various synthetic methods described in this specification or known in the art, such combinations can be easily performed by one of ordinary skill in the art of the present invention.

The methods of preparing the compounds of formula I-8 and compounds of formula I-9 used in the present invention are methods already known in the art. Generally, in the preparation process, each reaction is generally conducted in an inert solvent, at a temperature from room temperature to reflux temperature. The reaction time is usually 0.1 hours-60 hours, preferably 0.5 to 48 hours.

One preferable preparation method of the compound of formula I comprises the following steps:

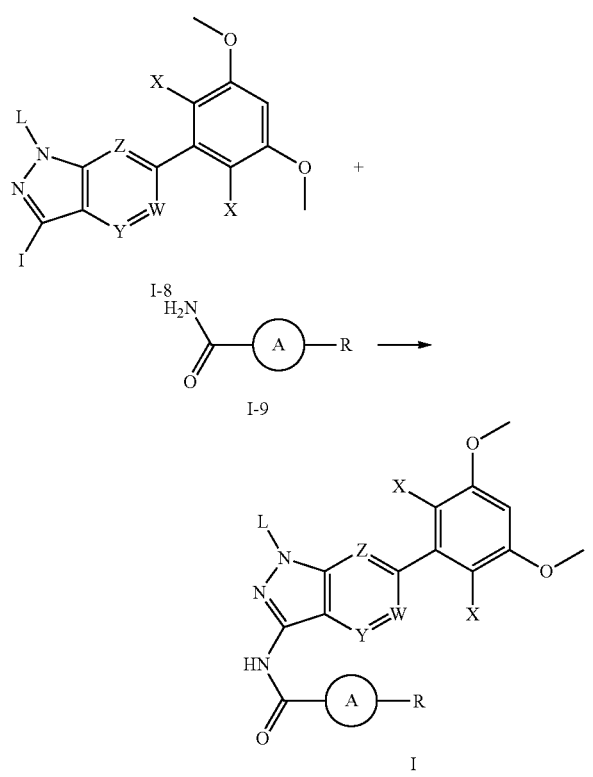

(a) In an inert solvent, reacting the compound of formula I-8 with the compound of formula I-9 to obtain the compound of formula I;

In the above formulas, the groups are defined as above.

In another preferred embodiment, the reaction is conducted with the presence of a copper salt; preferably, the copper salt is selected from (but is not limited to) the group consisting of the following: CuI, Cu, CuCl, $Cu_2O$, CuO, $Cu(OAc)_2$, $CuSO_4 \cdot 5H_2O$, $Cu(acac)_2$, $CuCl_2$, CuSCN, or a combination thereof.

In another preferred embodiment, said reaction is carried out in the presence of a ligand; preferably, said ligand is a bidentate amine ligand; more preferably, the ligand is selected from (but is not limited to) the group consisting of the following: N1, N2-dimethyl-ethylenediamine, (1R, 2R)-(−)-N, N'-dimethyl-1,2-cyclohexanediamine, or a combination thereof.

In another preferred embodiment, said reaction is carried out in the presence of a base; preferably said base is an inorganic base, and more preferably is selected from (but is not limited to) the group consisting of the following: $K_2CO_3$, $K_3PO_4$, $Cs_2CO_3$, or a combination thereof.

In another preferred embodiment, the inert solvent is selected from (but is not limited to) the group consisting of the following: toluene, dioxane, THF, DMF, or a combination thereof.

In another preferred embodiment, the method further comprises the following steps:

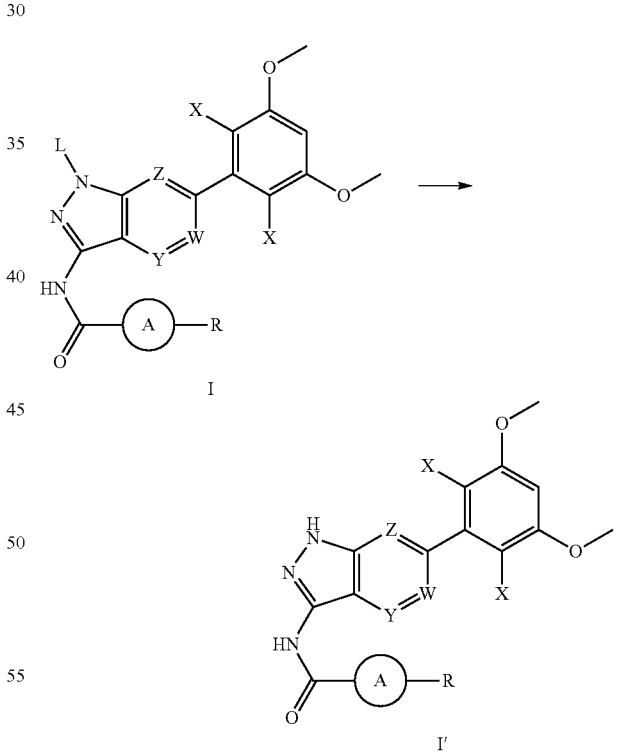

(b) deprotecting the compound of formula I in an inert solvent to give the compound of formula I'; wherein the other groups are defined as above.

In another preferred embodiment, the reaction is carried out in the presence of an acid; preferably, said acid is selected from (but is not limited to) the group consisting of the following: hydrochloric acid, p-toluenesulfonic acid, TFA, or a combination thereof.

In another preferred embodiment, the inert solvent is selected from (but is not limited to) the group consisting of the following: dichloromethane, methanol, ethanol, isopropanol, n-butanol, t-butanol, isobutanol, or a combination thereof.

A preferable preparation method comprises the following steps:

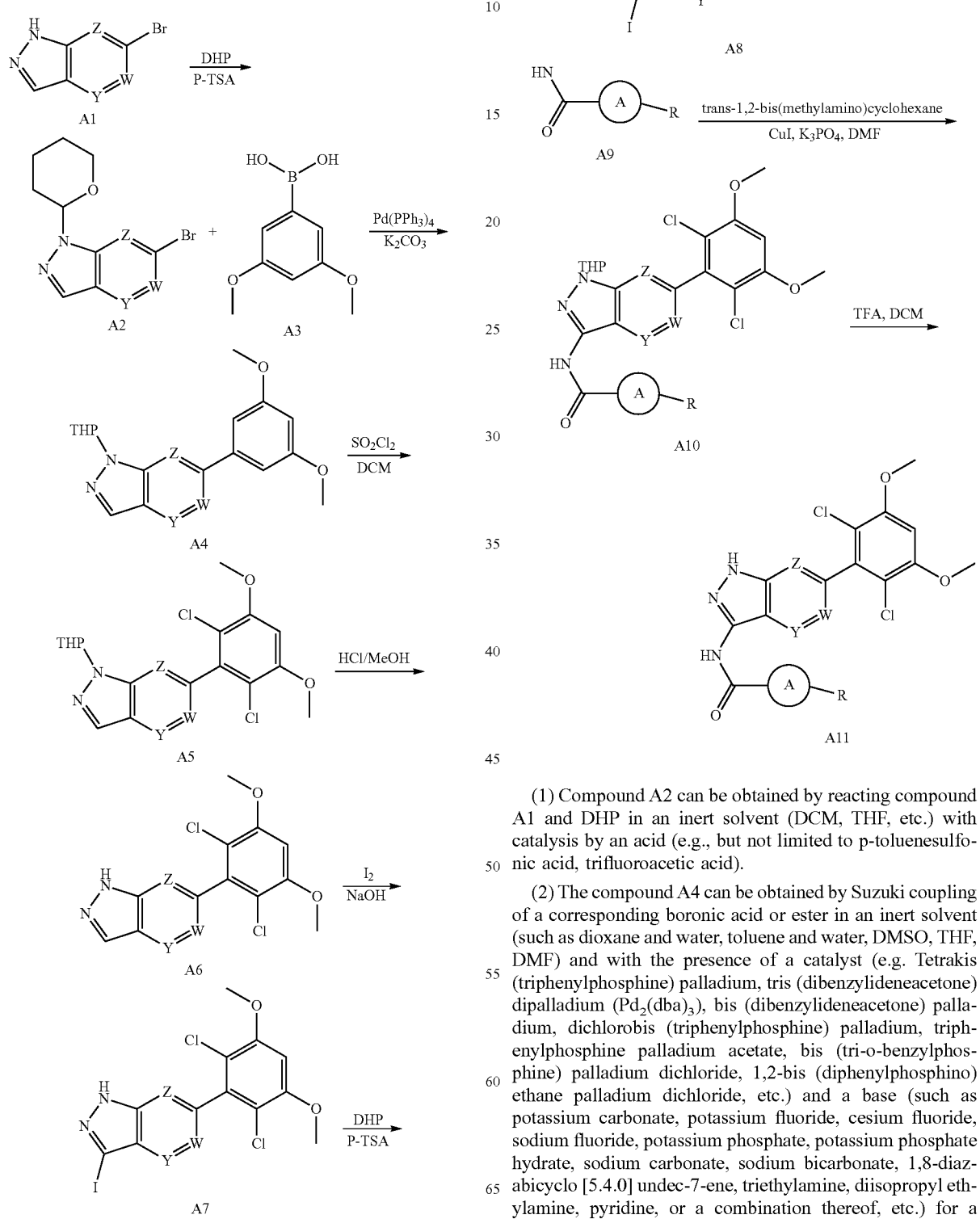

(1) Compound A2 can be obtained by reacting compound A1 and DHP in an inert solvent (DCM, THF, etc.) with catalysis by an acid (e.g., but not limited to p-toluenesulfonic acid, trifluoroacetic acid).

(2) The compound A4 can be obtained by Suzuki coupling of a corresponding boronic acid or ester in an inert solvent (such as dioxane and water, toluene and water, DMSO, THF, DMF) and with the presence of a catalyst (e.g. Tetrakis (triphenylphosphine) palladium, tris (dibenzylideneacetone) dipalladium ($Pd_2(dba)_3$), bis (dibenzylideneacetone) palladium, dichlorobis (triphenylphosphine) palladium, triphenylphosphine palladium acetate, bis (tri-o-benzylphosphine) palladium dichloride, 1,2-bis (diphenylphosphino) ethane palladium dichloride, etc.) and a base (such as potassium carbonate, potassium fluoride, cesium fluoride, sodium fluoride, potassium phosphate, potassium phosphate hydrate, sodium carbonate, sodium bicarbonate, 1,8-diazabicyclo [5.4.0] undec-7-ene, triethylamine, diisopropyl ethylamine, pyridine, or a combination thereof, etc.) for a period of time (e.g., 1 to 4 hours);

(3) Compound A5 can be obtained from compound A4 in an inert solvent (dichloromethane, THF, acetonitrile) by slowly adding $SO_2Cl_2$ dropwise and stirring at room temperature.

(4) Compound A6 can be obtained via the deprotection of compound A5 by adding an acid (such as hydrochloric acid, p-toluenesulfonic acid, TFA) in an inert solvent (such as dichloromethane, methanol, ethanol, isopropanol, n-butanol, tert-butanol, isobutanol).

(5) Compound A7 can be obtained by adding compound A6, iodine and NaOH in an inert solvent (1,4-dioxane, DMF, etc.) with stirring at room temperature.

(6) Compound A8 can be obtained by reacting compound A7 and DHP in an inert solvent (DCM, THF, etc.) with catalysis by an acid (e.g., but not limited to p-toluenesulfonic acid, trifluoroacetic acid).

(7) Compound A10 can be obtained by the amidation reaction of compound A8 and compound A9. Preferably, the reaction is carried out in the presence of one or more of the following reagents: a copper salt, which can be, but is not limited to CuI, Cu, CuCl, $Cu_2O$, CuO, $Cu(OAc)_2$, $CuSO_4.5H_2O$, $Cu(acac)_2$, $CuCl_2$, CuSCN, or a combination thereof; ligand, which can be bidentate amine ligands, including but not limited to N1, N2-dimethyl-ethylenediamine, (1R, 2R)-(−)-N, N'-dimethyl-1,2-cyclohexanediamine; base, which can be, but is not limited to inorganic bases such as $K_2CO_3$, $K_3PO_4$, $Cs_2CO_3$, and the reaction solvent can be, but is not limited to: toluene, dioxane, THF and DMF.

(8) Compound A11 can be obtained via the deprotection of compound A10 by using an appropriate acid (such as but not limited to hydrochloric acid, p-toluenesulfonic acid, TFA) in an inert solvent (such as dichloromethane, methanol, ethanol, isopropanol, n-butanol, t-butanol, isobutanol, etc.).

Use of the Compounds of Formula I

The compounds of formula I can be used in one or more of the following applications:

(a) manufacture of a medicament for treating diseases associated with FGFR kinase activity or expression amount;

(b) manufacture of FGFR kinase targeting inhibitors;

(c) in vitro non-therapeutic inhibition of FGFR kinase activity;

(d) in vitro non-therapeutic inhibition of tumor cell proliferation;

(e) treatment of diseases associated with FGFR kinase activity or expression amount.

In another preferred embodiment, the disease associated with FGFR activity or expression amount is tumor, preferably tumor selected from the group consisting of: endometrial cancer, breast cancer, stomach cancer, bladder cancer, myeloma, liver cancer.

In another preferred embodiment, the FGFR kinase is selected from the group consisting of: FGFR1, FGFR2, FGFR3, or a combination thereof.

In another preferred embodiment, the tumor cell is a leukemia cell strain; preferably myelogenous leukemia cell strain; more preferably acute myelogenous leukemia cell strain KG1.

The compound of formula I can be used to prepare a pharmaceutical composition, wherein the pharmaceutical composition comprises: (i) an effective amount of the compound of formula I, or a pharmaceutically acceptable salt thereof, and (ii) a pharmaceutically acceptable carrier.

In another preferred embodiment, the effective amount means therapeutically or inhibitory effective amount.

In another preferred embodiment, the pharmaceutical composition is used to inhibit the FGFR kinase activity.

In another preferred embodiment, the pharmaceutical composition is used to treat diseases associated with FGFR kinase activity or expression amount.

The compound of formula I of the invention can also be used in a method of inhibiting FGFR kinase activity, wherein the method comprises the following step: administering an inhibitory effective amount of the compound of formula I of claim 1 or a pharmaceutically acceptable salt thereof to a subject in need of inhibition, or administering an inhibitory effective amount of the pharmaceutical composition of claim 7 to a subject in need of inhibition.

In another preferred embodiment, the inhibition is in vitro non-therapeutic inhibition.

In another preferred embodiment, the inhibitory effective amount is from 0.001 to 500 nmol/L, preferably 0.01 to 200 nmol/L when an inhibitory effective amount of the compound of formula I in claim 1 or the pharmaceutically acceptable salt thereof is administered to a subject in need of inhibition.

Particularly, the present invention also provides a method for treating diseases associated with FGFR kinase activity or expression, wherein the method comprises: administering to a subject in need of treatment a therapeutically effective amount of the compound of formula I, or the pharmaceutical composition which comprises the compound of formula I as an active ingredient.

In another preferred embodiment, the disease associated with FGFR activity or expression amount is tumor, preferably tumor selected from the group consisting of: endometrial cancer, breast cancer, stomach cancer, bladder cancer, myeloma, liver cancer.

Pharmaceutical Composition and the Administration Thereof

The compounds of the present invention possess outstanding activity of inhibiting FGFR kinases, such as FGFR1, FGFR2 and FGFR3 kinases. Therefore, the compounds of the present invention, and the crystal forms, pharmaceutically acceptable inorganic or organic salts, hydrates or solvates thereof, and the pharmaceutical compositions comprising the compound of the present invention as a main active ingredient can be used for treating, preventing and alleviating diseases related to FGFR activity or expression level. According to the prior art, the compounds of the present invention can be used to treat the following diseases: endometrial cancer, breast cancer, stomach cancer, bladder cancer, myeloma, liver cancer and the like.

The pharmaceutical composition of the invention comprises the compound of the present invention or a pharmacologically acceptable salt thereof in a safe and effective dosage range and a pharmacologically acceptable excipient or carrier. Wherein the "safe and effective dosage" means that the amount of the compound is sufficient to notably ameliorate the condition without causing severe side effects. Generally, the pharmaceutical composition contains 1-2000 mg of the compound of the present invention per dose, preferably, 5-200 mg of the compound of the present invention per dose. Preferably, the "dose" is a capsule or tablet.

"Pharmaceutically acceptable carrier" means one or more compatible solid or liquid fillers or gelatinous materials which are suitable for human use and should be of sufficient purity and sufficiently low toxicity. The term "compatible" means that each component in the composition can be admixed with the compound of the present invention and with each other without significantly reducing the efficacy of the compound. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation on the administration mode of the compounds or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or $Ca_2HPO_4$, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and Arabic gum; (c) humectants, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent, and furthermore, the active compound(s) or the compound(s) in the composition can be released in a delayed mode in a given portion of the digestive tract. Examples of the embedding components include polymers and waxes. If necessary, the active compounds and one or more of the above excipients can form microcapsules.

Liquid dosage forms for oral administration include pharmaceutically acceptable emulsions, solutions, suspensions, syrups or tinctures. In addition to the active compounds, the liquid dosage forms may contain conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or a combination thereof.

Besides these inert diluents, the composition may also contain auxiliaries such as wetting agents, emulsifiers, and suspending agent, sweetener, flavoring agents and spices.

In addition to the active compounds, a suspension may contain suspending agents, for example, ethoxylated isooctadecanol, polyoxyethylene sorbitol and sorbitan esters, microcrystalline cellulose, methanol aluminum and agar, or a combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of the compounds of the present invention include ointments, powders, patches, aerosol, and inhalants. The active ingredients are mixed with physiologically acceptable carriers and any preservatives, buffers, or propellant if necessary, under sterile conditions.

The compounds of the present invention can be administrated alone, or in combination with any other pharmaceutically acceptable compound(s).

When the pharmaceutical compositions are used, a safe and effective amount of the compound of the present invention is applied to a mammal (such as human) in need of treatment, wherein the dose of administration is a pharmaceutically effective dose. For a person of 60 kg, the daily dose is usually 1-2000 mg, preferably 5-500 mg. Of course, the particular dose should also depend on various factors, such as the route of administration, patient healthy status, which are well within the skills of an experienced physician.

The Main Advantages of the Present Invention Include

1. Providing a compound of formula I.
2. Providing a structurally novel FGFR inhibitor and the preparation and use thereof, wherein the inhibitor can inhibit the activity of various FGFR kinases at extremely low concentrations.
3. Providing a pharmaceutical composition for the treatment of diseases associated with FGFR kinase activity.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

In all the examples:
LCMS instrument: Pump Agilent 1100 UV detector: Agilent 1100 DAD
Mass Spectrometer API 3000
chromatographic column: Waters sunfire C18, 4.6×50 mm, 5 um
Mobile phase: A-acetonitrile B—$H_2O$ (0.1% FA)

Example 1

Synthetic Route I

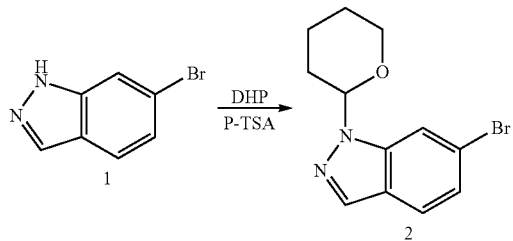

Compound 1 (10.00 g, 51.0 mmol), p-TSA (1.75 g, 10.2 mmol) and dichloromethane (100.0 mL) were added to a dry 250 mL round-bottom flask, and DHP (8.56 g, 102.0 mmol) was slowly added dropwise, stirred at room temperature for 4.0 h. After completion of the reaction, the reaction solution was diluted with 100.0 mL of water and extracted twice with 200 mL of dichloromethane. The organic phases were combined and dried over anhydrous sodium sulfate and the solvent was rotary dried to give compound 2 (8.90 g, 62%). LCMS: 281 (M+H)+, RT=1.626 mim.

and stirred at room temperature for 4.0 h. The reaction solution was diluted with 50.0 mL of water, extracted twice with 200 mL of dichloromethane, and washed with saturated NaHCO₃. The organic phases were combined and dried over anhydrous sodium sulfate and the solvent was rotary dried to give compound 5 (8.50 g, 89%). LC MS: 407 (M+H)+, RT=1.798 mim.

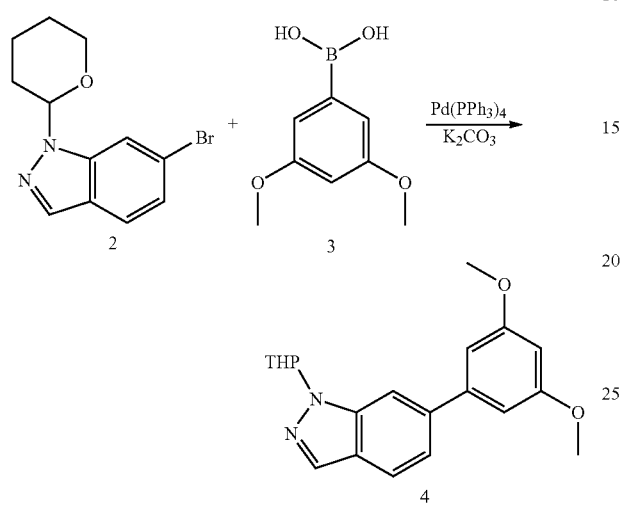

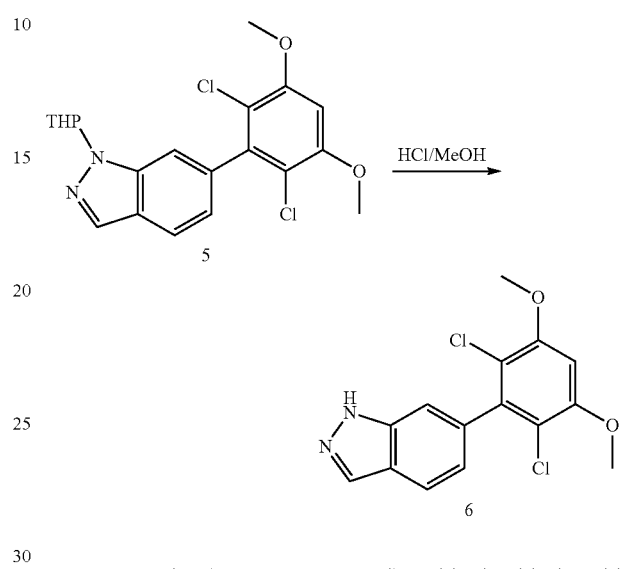

Compound 2 (8.90 g, 31.7 mmol), 3 (5.77 g, 31.7 mmol), Pd(PPh₃)₄ (3.66 g, 3.17 mmol), K₂CO₃ (8.75 g, 63.4 mmol), 1,4-dioxane (60.0 mL) and water (15.0 mL) were successively added into a dry 250 mL round-bottom flask at room temperature, stirred to evenly dispersed in the system. Under nitrogen protection, the reaction was heated to reflux for 4.0 h. The reaction solution was cooled to room temperature and the solvent was rotary dried to give the crude product. Column chromatography (ethyl acetate:petroleum ether=1:10) gave Compound 4 (8.10 g, 76%). LC MS: 339 (M+H)+, RT=1.626 mim.

Compound 5 (8.50 g, 20.9 mmol) and hydrochloric acid methanol solution (1M) (80.0 mL) were added to a dry 250 mL round-bottom flask, and heated to reflux for 16.0 h. The solvent was rotary dried to give 7.50 g of compound 6, which was used in the next step without further purification. LCMS: 323 (M+H)+, RT=1.592 mim.

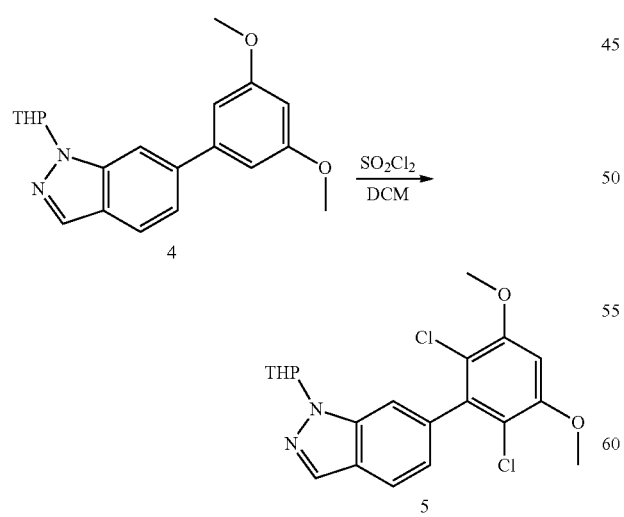

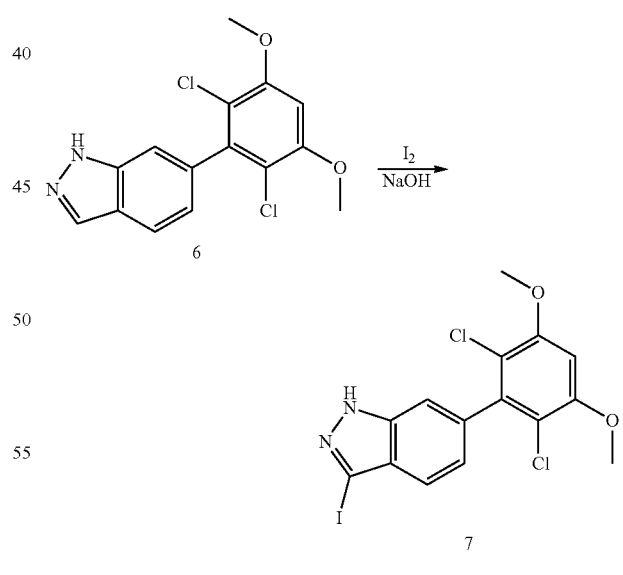

Compound 4 (7.90 g, 23.4 mmol) and dichloromethane (50.0 mL) were added to a dry 250 mL round-bottom flask, and SO₂Cl₂ (7.15 g, 46.7 mmol) was slowly added dropwise, Compound 6 (7.40 g, 23.0 mmol), iodine (11.68 g, 46.0 mmol), NaOH (1.84 g, 46.0 mmol) and 1,4-dioxane (60.0 mL) were added to a dry 250 mL round-bottom flask. The reaction mixture was stirred at room temperature for 2.0 hours. After completion of the reaction, the reaction solution was added with 200 mL of water and extracted twice with 200 mL of dichloromethane. The organic phase were washed with saturated sodium thiosulfate, combined and dried over anhydrous sodium sulfate, and the solvent was rotary dried to give compound 7 (9.50 g, 92%). LC MS: 449 (M+H)+, RT=1.644 mim.

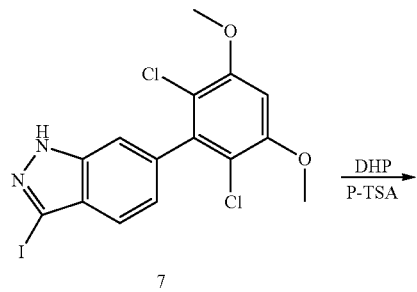

7 evenly. The mixture was then heated to 130° C. and reacted for 8 h. It was poured into IL of water after the reaction was completed, and extracted three times with ethyl acetate (150 mL*3). The organic phase was washed with 100 mL of saturated brine, dried over anhydrous sodium sulfate and the solvent was rotary dried to give 15 g of slightly yellow solid, 85% yield.

$^1$H NMR (400 MHz, CDCl$_3$) δ (ppm) 7.48 (2H, d, J=8.8 Hz), 6.85 (2H, d, J=8.0 Hz), 3.65 (2H, dd, J$_1$=12.0 Hz, J$_2$=2.0 Hz), 2.95-3.01 (2H, m), 2.42 (2H, t, J=11.4 Hz), 1.15 (6H, d, J=6.4 Hz)

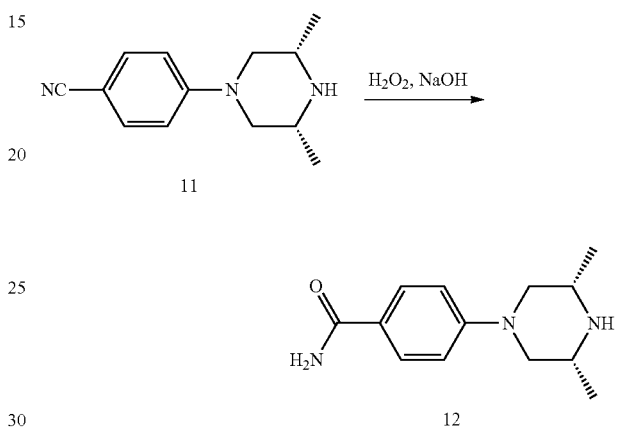

Compound 7 (9.30 g, 20.76 mmol), p-TSA (0.71 g, 4.152 mmol) and dichloromethane (50.0 mL) were added to a dry 250 mL round-bottom flask, and DHP (3.48 g, 41.52 mmol) was slowly added dropwise, stirred at room temperature for 4.0 h. The reaction solution was diluted with 50.0 mL of water and extracted twice with 200 mL of dichloromethane. The organic phases were combined and dried over anhydrous sodium sulfate and the solvent was rotary dried to give compound 8 (7.70 g, 70%). LC MS: 281 (M+H)+, RT=2.165 mim.

$^1$H NMR (CDCl$_3$, 400 MHz) δ (ppm) 7.56 (d, 1H, J=8.0 Hz), 7.45 (s, 1H), 7.09 (d, 1H, J=8.0 Hz), 6.65 (s, 1H), 5.70 (t, 1H, J=4.0 Hz), 4.03 (s, 1H), 3.98 (s, 6H), 3.69 (t, 1H, J=8.0 Hz), 2.53 (t, 1H, J=10 Hz), 2.12 (m, 2H), 1.68-1.74 (m, 2H), 1.56-1.63 (m, 1H).

Compound 11 (9.03 g, 42 mmol) was dissolved in 175 mL of ethanol and NaOH (6.0N, 105 mL) and H$_2$O$_2$ (16.1 mL) were added sequentially to the solution at room temperature. The mixture was warmed to 50° C. and stirred for 5 hours. After completion of the reaction, the solution was cooled to 0° C. and adjusted to pH 7 with 3N sulfuric acid. The organic phase was rotary evaporated, stirred at 0° for 30 minutes, and filtered to give 6.5 g of white solid, 66% yield.

$^1$H NMR (400 MHz, DMSO-d6): δ (ppm) 7.76 (2H, d, J=8.8 Hz), 7.73 (1H, br), 7.04 (1H, br), 6.97 (2H, d, J=8.8 Hz), 3.85 (2H, d, J=1.2 Hz), 3.08 (2H, br), 2.45 (2H, t, J=11.6 Hz), 1.15 (6H, d, J=6.4 Hz).

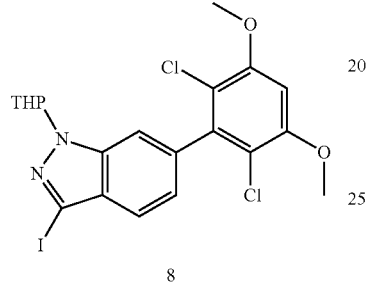

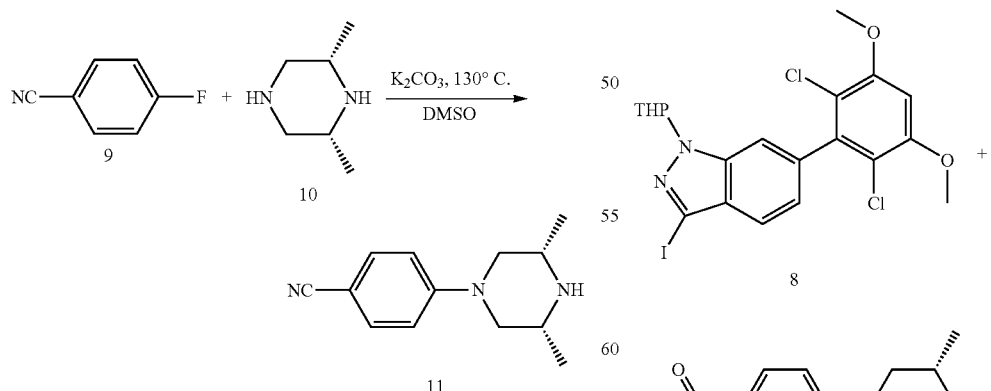

Compound 9 (10 g, 82.6 mmol) was added into a 500 mL one-neck flask, and 200 mL of DMSO was added. (2R,6S)-2,6-dimethylpiperazine (14 g, 124 mmol) and K$_2$CO$_3$ (28.5 g, 206.5 mmol) were added at room temperature, and stirred -continued

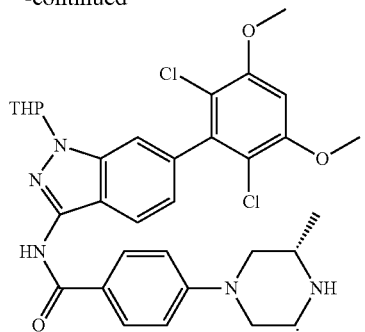

13

Compound 8 (2.0 g, 3.75 mmol) was dissolved in 20 mL of anhydrous DMF, and trans-N, N'-dimethyl-1,2-cyclohexanediamine (107 mg, 0.75 mmol), CuI (36 mg, 0.19 mmol), K$_3$PO$_4$ (1.6 g, 7.5 mmol) and 12 (1.05 g, 4.5 mmol) were successively added into the solution at room temperature. It was purged with nitrogen for three times and warmed to 110° C. and stirred for 16 hours. After completion of the reaction, the solvent was rotary evaporated to obtain the crude product, which was purified by column chromatography (dichloromethane:methanol=40:1) to give a white solid (0.98 g), yield 41%.

$^1$H NMR (CDCl$_3$, 400 MHz) δ (ppm) 8.46 (s, 1H), 8.22 (d, 1H, J=8.0 Hz), 7.86 (d, 2H, J=8.0 Hz), 7.35 (s, 1H), 7.01 (d, 1H, J=8.0 Hz), 6.94 (d, 2H, J=8.0 Hz), 6.62 (s, 1H), 5.61 (m, 1H), 3.96 (s, 6H), 3.71 (m, 3H), 3.06 (m, 2H), 2.48 (m, 3H), 2.06 (m, 3H), 1.70 (m, 3H), 1.20 (s, 3H), 1.18 (s, 3H).

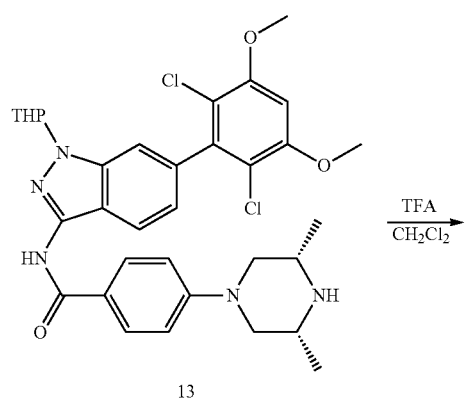

13

TFA / CH$_2$Cl$_2$

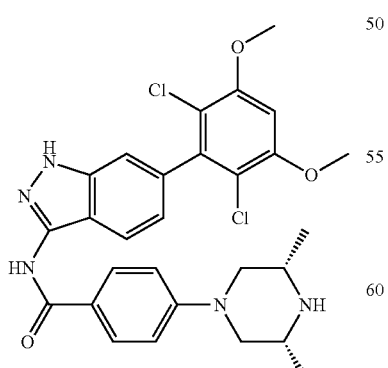

14

Compound 13 (0.86 g, 1.35 mmol) was dissolved in 10 mL of dichloromethane, and trifluoroacetic acid (5 mL) was added to the solution at room temperature. The mixture was stirred at room temperature for 4 hours. After completion of the reaction, the solvent was rotary evaporated to obtain the crude product, which was purified by column chromatography (dichloromethane:methanol=20:1) to give white solid (0.61 g), yield 82%.

$^1$H NMR (CDCl$_3$, 400 MHz) δ (ppm) 8.79 (s, 1H), 8.15 (d, 1H, J=8.0 Hz), 7.86 (d, 2H, J=8.0 Hz), 7.26 (s, 1H), 6.99 (d, 1H, J=8.0 Hz), 6.89 (d, 2H, J=8.0 Hz), 6.62 (s, 1H), 3.96 (s, 6H), 3.65 (m, 2H), 3.06 (m, 2H), 1.17 (s, 3H), 1.15 (s, 3H).

The following compounds were obtained by similar methods:

N-(6-(2,6-dichloro-3,5-dimethoxyphenyl)-1H-indazole-3-yl)-4-(4-methylpiperazine-1-yl)benzamide

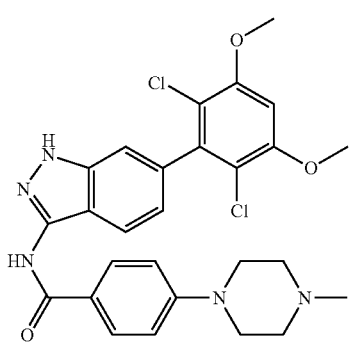

15

$^1$H NMR (CDCl$_3$, 400 MHz) δ (ppm) 8.83 (s, 1H), 8.21 (d, 1H, J=8.0 Hz), 7.89 (d, 2H, J=8.0 Hz), 7.23 (s, 1H), 6.99 (d, 1H, J=8.0 Hz), 6.91 (d, 2H, J=8.0 Hz), 6.61 (s, 1H), 3.95 (s, 6H), 3.33 (m, 4H), 2.56 (m, 4H), 2.35 (s, 3H).

N-(6-(2,6-dichloro-3,5-dimethoxyphenyl)-1H-indazole-3-yl)-4-((4-methylpiperazine-1-yl)methyl)benzamide

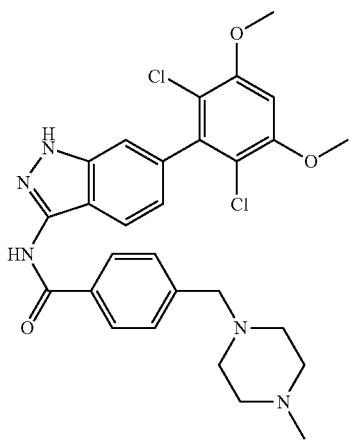

16

$^1$H NMR (MeOD, 400 MHz) δ (ppm) 8.03 (d, 2H, J=8.0 Hz), 7.84 (d, 1H, J=8.0 Hz), 7.53 (d, 2H, J=8.0 Hz), 7.29 (s, 1H), 6.93 (d, 1H, J=8.0 Hz), 6.87 (s, 1H), 3.97 (s, 6H), 3.68 (s, 2H), 2.98 (br, 4H), 2.56 (br, 4H), 2.54 (s, 3H).

N-(6-(2,6-dichloro-3,5-dimethoxyphenyl)-1H-indazole-3-yl)-4-morpholino benzamide

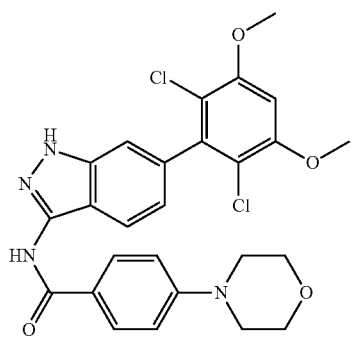

17

¹H NMR (MeOD, 400 MHz) δ (ppm) 8.02 (d, 2H, J=8.0 Hz), 7.97 (d, 1H, J=8.0 Hz), 7.32 (s, 1H), 7.07 (d, 2H, J=8.0 Hz), 7.99 (d, 1H, J=8.0 Hz), 6.88 (s, 1H), 3.98 (s, 6H), 3.84 (t, 4H, J=5.2 Hz), 3.33 (t, 4H, J=5.2 Hz).

N-(6-(2,6-dichloro-3,5-dimethoxyphenyl)-1H-indazole-3-yl)-4-(4-ethylpiperazine-1-yl)benzamide

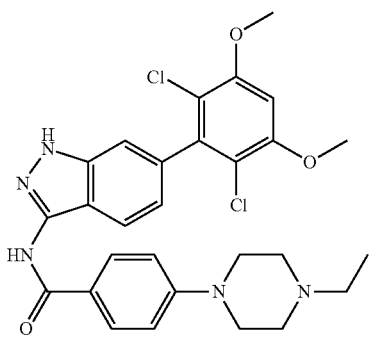

18

¹H NMR (MeOD, 400 MHz) δ (ppm) 8.09 (m, 3H), 7.36 (s, 1H), 7.20 (m, 2H), 7.99 (m, 1H), 6.89 (s, 1H), 3.97 (s, 6H), 3.27 (m, 2H), 1.4 (t, 3H, J=6.4 Hz).

4-((4-acetyl-1-yl)methyl)-N-(6-(2,6-dichloro-3,5-dimethoxyphenyl)-1H-indazole-3-yl)benzamide

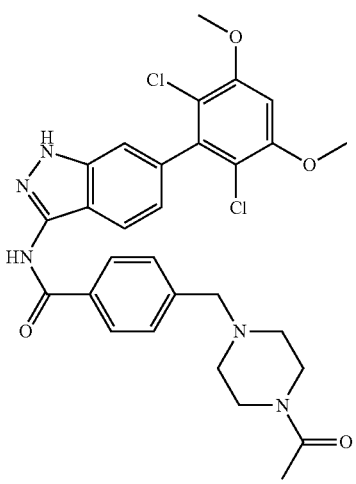

19

¹H NMR (DMSO-d6, 400 MHz) δ (ppm) 12.88 (s, 1H), 10.81 (s, 1H), 8.06 (d, 2H, J=8.0 Hz), 7.77 (d, 1H, J=8.0 Hz) 7.78 (d, 2H, J=8.0 Hz), 7.29 (s, 1H), 7.00 (s, 1H), 6.85 (d, 1H, J=8.0 Hz), 3.97 (s, 6H), 3.59 (s, 2H), 2.40 (t, 2H, J=4.8 Hz), 2.33 (t, 2H, J=4.8 Hz), 1.98 (s, 3H).

N-(6-(2,6-dichloro-3,5-dimethoxyphenyl)-1H-indazole-3-yl)-4-((2-(dimethylamino)ethyl)amino)benzamide

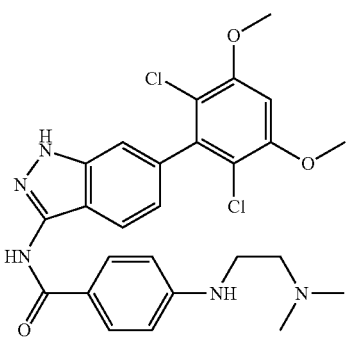

20

¹H NMR (400 MHz, DMSO-d6/D2O) δ (ppm) 7.87 (2H, s), 7.71 (1H, s), 7.29 (1H, s), 7.10-6.60 (4H, m), 3.91 (6H, s), 3.70 (2H, s), 3.48 (2H, s), 2.80 (6H, s).

N-(6-(2,6-dichloro-3,5-dimethoxyphenyl)-1H-indazole-3-yl)-5-((3R,5S)-3,5-dimethyl-1-yl)pyridine amide

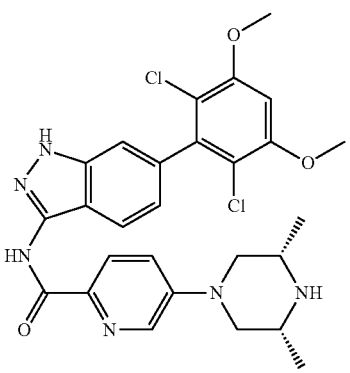

21

¹H NMR (DMSO-d6, 400 MHz) δ (ppm) 12.89 (1H, br), 10.48 (1H, s), 9.06 (1H, br), 8.51 (2H, br), 8.05 (1H, d, J=8.8 Hz), 7.94 (1H, d, J=8.4 Hz), 7.60-7.63 (1H, m), 7.29 (1H, s), 7.01 (1H, s), 4.22 (2H, d, J=14.4 Hz), 3.97 (6H, s), 2.84 (2H, t, J=12.6 Hz), 2.54-2.58 (2H, m), 1.30 (6H, d, J=6.4 Hz).

N-(6-(2,6-dichloro-3,5-dimethoxyphenyl)-1H-indazole-3-yl)-4-(3,3-dimethyl-1-yl)benzamide

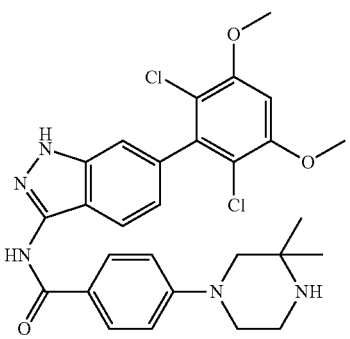

22

¹H NMR (400 MHz, DMSO-d6) δ (ppm) 12.85 (s, 1H), 10.57 (s, 1H), 8.01 (2H, d, J=8.8 Hz), 7.76 (1H, d, J=8.4 Hz), 7.29 (s, 1H), 7.07 (2H, d, J=8.8 Hz), 7.01 (1H, s), 6.85 (d, 1H, J=8.4 Hz), 3.98 (s, 6H), 3.18-3.50 (m, 6H), 1.31 (s, 6H).

N-(6-(2,6-dichloro-3,5-dimethoxyphenyl)-1H-indazole-3-yl)-3-(4-methyl-1-yl)benzamide

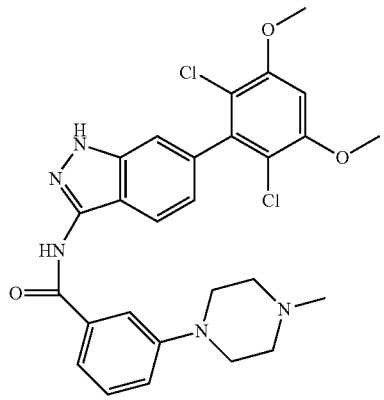

¹H NMR (400 MHz, DMSO-d6) δ (ppm) 12.92 (1H, s), 10.83 (1H, s), 9.60-9.20 (1H, m), 7.78 (1H, d, J=8.4 Hz), 7.68 (1H, s), 7.58 (1H, d, J=7.6 Hz), 7.44 (1H, t, J=8.0 Hz), 7.30 (1H, s), 7.26 (1H, dd, J₁=1.6 Hz, J₂=8.0 Hz), 7.00 (1H, s), 6.87 (1H, d, J=8.4 Hz), 3.97 (6H, s), 3.30-3.10 (4H, m), 3.10-2.80 (4H, m), 2.88 (3H, s).

N-(6-(2,6-dichloro-3,5-dimethoxyphenyl)-1H-indazole-3-yl)-4-(4-isopropyl-1-yl)benzamide

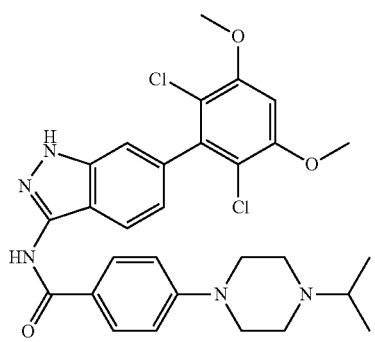

¹H NMR (MeOD, 400 MHz) δ (ppm) 8.08 (br, 2H), 7.99 (br, 1H), 7.33 (br, 1H), 7.18 (br, 2H), 7.02 (br, 1H), 6.89 (s, 1H), 4.11-4.17 (m, 2H), 3.57-3.64 (m, 3H), 3.19-3.37 (m, 4H), 1.42 (6H, d, J=6.4 Hz).

N-(6-(2,6-dichloro-3,5-dimethoxyphenyl)-1H-indazole-3-yl)-4-(piperazine-1-yl)benzamide

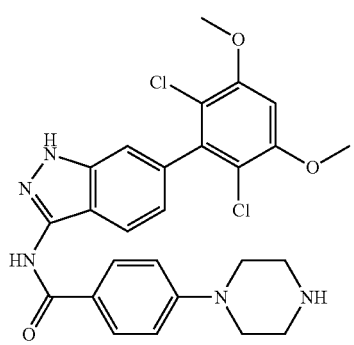

¹H NMR (MeOD, 400 MHz) δ (ppm) 8.00 (2H, d, J=9.2 Hz), 7.83 (1H, d, J=8.4 Hz), 7.28 (s, 1H), 7.10 (2H, d, J=9.2 Hz), 6.90 (1H, d, J=8.4 Hz), 6.88 (s, 1H), 3.97 (s, 6H), 3.48-3.51 (m, 4H), 3.18-3.25 (m, 4H).

N-(6-(2,6-dichloro-3,5-dimethoxyphenyl)-1H-indazole-3-yl)-4-((3(dimethylamino)propyl)amino)benzamide

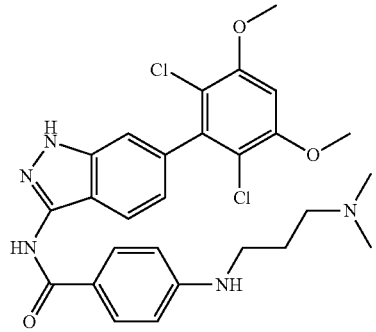

¹H NMR (400 MHz, DMSO-d6) δ (ppm) 12.87 (1H, br), 10.39 (s, 1H), 9.57 (1H, br), 7.80 (2H, d, J=8.8 Hz), 7.75 (1H, d, J=8.4 Hz), 7.27 (s, 1H), 6.84 (1H, d, J=8.4 Hz), 6.66 (2H, d, J=8.8 Hz), 3.98 (6H, s), 3.20 (4H, t, J=6.8 Hz), 2.80 (s, 6H), 10.89-10.96 (m, 2H).

N-(6-(2,6-dichloro-3,5-dimethoxyphenyl)-1H-indazole-3-yl)-4-(4-(2-hydroxyethyl)piperazinyl)benzamide

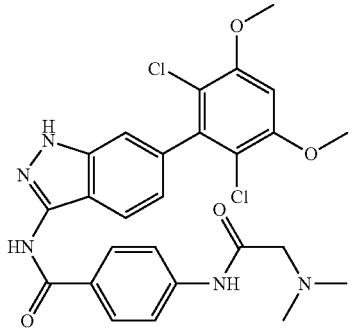

¹H NMR (400 MHz, DMSO-d6) δ (ppm) 12.85 (1H, br), 10.62 (1H, s), 9.73 (1H, br), 8.05 (2H, d, J=8.8 Hz), 7.76 (1H, d, J=8.4 Hz), 7.29 (1H, s), 7.13 (2H, d, J=8.8 Hz), 6.87 (1H, s), 6.86 (1H, d, J=8.4 Hz), 4.06-4.08 (m, 2H), 3.98 (6H, s), 3.80 (2H, t, J=4.8 Hz), 3.56-3.60 (m, 2H), 3.14-3.28 (m, 6H).

N-(6-(2,6-dichloro-3,5-dimethoxyphenyl)-1H-indazole-3-yl)-4-(2-(dimethylamino)acetylamino)benzamide ¹H NMR (400 MHz, DMSO-d6) δ (ppm) 12.92 (1H, s), 10.78 (1H, s), 10.08 (1H, s), 8.12 (2H, d, J=8.8 Hz), 7.89

(2H, d, J=8.8 Hz), 7.83 (1H, d, J=8.4 Hz), 7.34 (1H, s), 7.06 (1H, s), 6.91 (1H, d, J=8.4 Hz), 4.03 (6H, s), 3.18 (s, 2H), 2.35 (s, 6H).

N-(6-(3,5-dimethoxyphenyl)-1H-indazole-3-yl)-4-((3R, 5S)-3,5-dimethyl piperazine-1-yl)benzamide

29

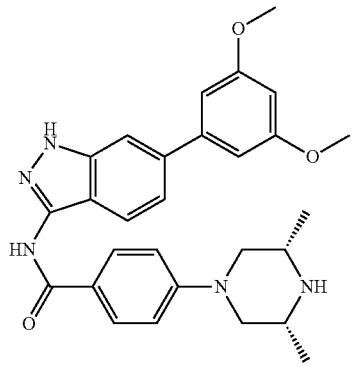

¹H NMR (d6-DMSO, 400 MHz) δ ppm 12.78 (s, 1H), 10.50 (s, 1H), 7.97 (d, 2H, J=9.2 Hz), 7.76 (d, 1H, J=8.4 Hz), 7.66 (s, 1H), 7.36 (d, 1H, J=8.4 Hz), 7.01 (d, 2H, J=8.8 Hz), 6.84 (d, 2H, J=2.0 Hz), 6.53 (s, 1H), 3.83 (s, 6H), 3.76 (d, 2H, J=6.8 Hz), 2.83 (s, 2H), 2.24 (t, 3H, J=6.8 Hz), 1.23 (s, 4H), 1.04 (d, 6H, J=6.4 Hz).

N-(6-(2,6-dichloro-3,5-dimethoxyphenyl)-1H-indazole-3-yl)-4-(4-pivaloyl piperazine-1-yl)benzamide

30

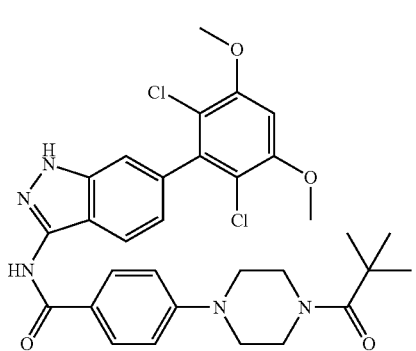

¹H NMR (d6-DMSO, 400 MHz) δ ppm 12.81 (s, 1H), 10.6 (s, 1H), 8.01 (d, 2H, J=8.8 Hz), 7.75 (d, 1H, J=4.4 Hz), 7.27 (s, 1H), 7.03 (d, 2H, J=8.8 Hz), 7.00 (s, 1H), 6.84 (d, 1H, j=8.8 Hz), 4.00 (s, 6H), 3.70-3.72 (m, 41H), 3.30-3.32 (m, 4H), 1.23 (s, 9H).

N-(6-(2,6-dichloro-3,5-dimethoxyphenyl)-1H-indazole-3-yl)-1-(2-hydroxyethyl)-1H-pyrazol-4-formamide

31

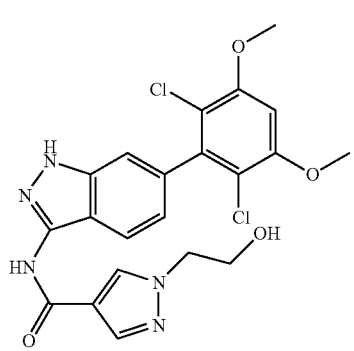

¹H NMR (d6-DMSO, 400 MHz) δ ppm 12.84 (brs, 1H), 10.53 (s, 1H) 8.41 (s, 1H) 8.11 (s, 1H), 7.80 (d, 1H, J=8.4 Hz), 7.26 (s, 1H) 7.01 (d, 1H, J=3.2 Hz), 6.84 (d, 1H, J=8.4 Hz) 4.21 (t, 2H, J=5.2 Hz), 3.94 (s, 6H) 3.77 (t, 2H, J=5.2 Hz).

N-(6-(2,6-dichloro-3,5-dimethoxyphenyl)-1H-indazole-3-yl)-2,3-dihydroimidazo[5,1-B]oxazole-7-formamide

32

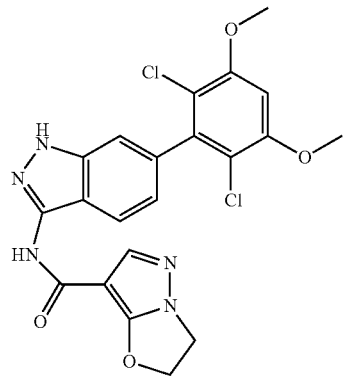

¹H NMR (d6-DMSO, 400 MHz) δ ppm 12.80 (brs, 1H), 10.18 (s, 1H), 8.07 (s, 1H), 7.77 (d, 1H, J=8.0 Hz), 7.25 (s, 1H), 7.00 (s, 1H), 6.83 (dd, 1H, J1=0.8 Hz, J2=8.4 Hz), 5.23 (t, 2H, J=7.6 Hz), 4.33 (t, 2H, J=8.0 Hz), 3.97 (s, 6H).

N-(6-(2,6-dichloro-3,5-dimethoxyphenyl)-1H-indazole-3-yl)-4-(3-(dimethylamino)-3-oxo propyl)benzamide

33

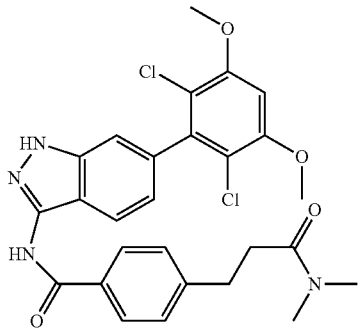

¹H NMR (d6-DMSO, 400 MHz) δ ppm 12.90 (s, 1H), 10.78 (s, 1H), 8.00 (d, 2H, J=8.4 Hz), 7.77 (d, 1H, J=8.4 Hz), 7.42 (d, 2H, J=8.0 Hz), 7.03 (s, 1H), 7.01 (d, 1H), 6.86 (d, 1H, J=8.4 Hz), 3.98 (s, 6H), 2.91 (t, 2H, J=14.4 Hz), 2.84 (s, 3H), 2.67 (t, 2H, J=14.4 Hz).

N-(6-(2,6-dichloro-3,5-dimethoxyphenyl)-1H-indazole-3-yl)-4-((dimethylamino)methyl)benzamide

34

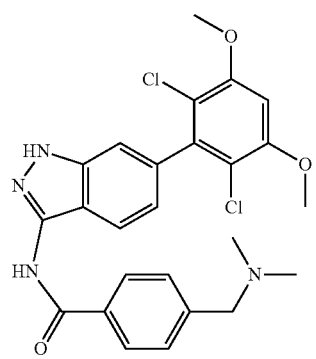

¹H NMR (d6-DMSO, 400 MHz) δ ppm 12.95 (s, 1H), 10.97 (s, 1H), 9.85 (d, 1H, J=2.8 Hz), 8.17 (d, 2H, J=8.0 Hz), 7.78 (d, 1H, J=8.0 Hz), 7.66 (d, 2H, J=8.4 Hz), 7.31 (s, 1H), 7.00 (s, 1H), 6.87 (d, 1H, J=8.4 Hz), 4.39 (d, 2H, J=4.4 Hz), 3.97 (s, 6H), 2.79 (t, 6H, J=3.6 Hz).

N-(6-(2,6-dichloro-3,5-dimethoxyphenyl)-1H-indazole-3-yl)-4-(dimethylamino)benzamide

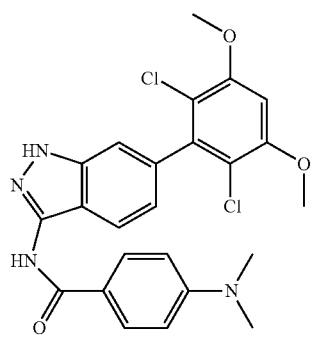

35

¹H NMR (d6-DMSO, 400 MHz) δ ppm 12.82 (s, 1H), 10.47 (s, 1H), 7.98 (d, 2H, J=6.4 Hz), 7.76 (d, 1H, J=8.0 Hz), 7.28 (s, 1H), 7.03 (s, 1H), 7.01 (s, 1H), 6.84 (d, 1H, J=8.41 Hz), 6.78 (d, 2H, J=6.8 Hz), 3.98 (s, 6H), 3.18 (s, 6H).

4-(4-acetylpiperazine-1-yl)-N-(6-(2,6-dichloro-3,5-dimethoxyphenyl)-1H-indazole-3-yl)benzamide

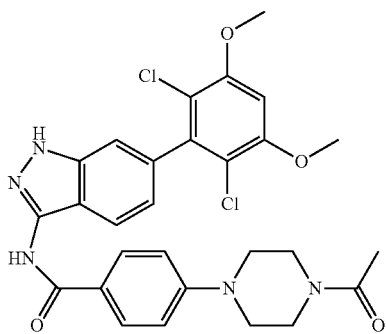

36

¹H NMR (d6-DMSO, 400 MHz) δ ppm 12.89 (s, 1H), 10.62 (s, 1H), 8.06 (d, 2H, J=8.8 Hz), 7.82 (d, 1H, J=8.4 Hz), 7.34 (s, 1H), 7.10 (d, 2H, J=8.8 Hz), 7.06 (s, 1H), 6.84 (d, 1H, j=8.4 Hz), 4.03 (s, 6H), 3.65-3.66 (m, 4H), 3.38-3.43 (m, 4H), 2.10 (s, 3H).

N-(6-(2,6-dichloro-3,5-dimethoxyphenyl)-1H-indazole-3-yl)-4-(4-(dimethylamino)piperidine-1-yl)benzamide

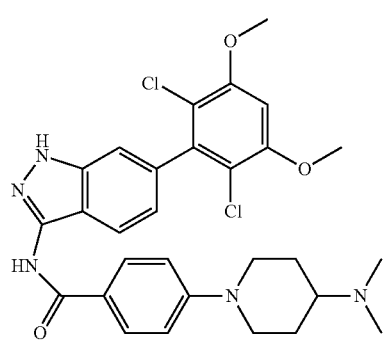

37

¹H NMR (CDCl3, 400 MHz) δ ppm 8.48 (s, 1H), 8.23 (d, 1H, J=8 Hz), 7.88 (d, 2H, J=8.8 Hz), 7.02 (d, 1H, J=8.8 Hz), 6.79 (d, 2H, J=8.41 Hz), 6.63 (s, 1H), 3.97 (s, 6H), 3.93 (d, 2H, J=14 Hz), 2.84-2.87 (m, 2H), 2.33 (m, 7H), 1.95 (d, 4H, J=12 Hz). LCMS: 568 (M+H)⁺, RT=1.25 min.

Synthetic Route II

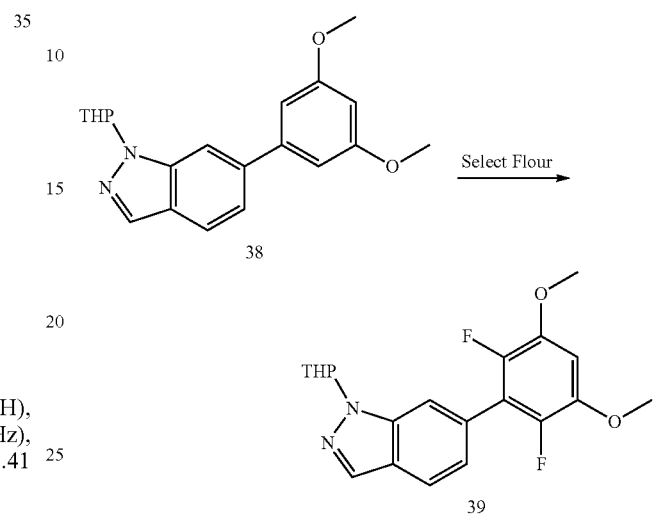

Compound 38 (1.20 g, 3.55 mmol) and acetonitrile (20.0 mL) were added to a dry 50 mL round-bottom flask. Under the protection of N₂, Select Flour (2.51 g, 7.1 mmol) was added in batches at 0° C., and stirred at room temperature for 18.0 h. The reaction solution was diluted with water and extracted with ethyl acetate. The organic phase was successively washed with water, saturated NaHCO₃, and saturated brine. Dried over anhydrous sodium sulfate, and the solvent was rotary evaporated to obtain the crude product, which was subjected to column chromatography (ethyl acetate: petroleum ether=1:8) to give the crude compound 39 (629 mg, 47%). LCMS: 374.9 (M+H)⁺, RT=1.243 min.

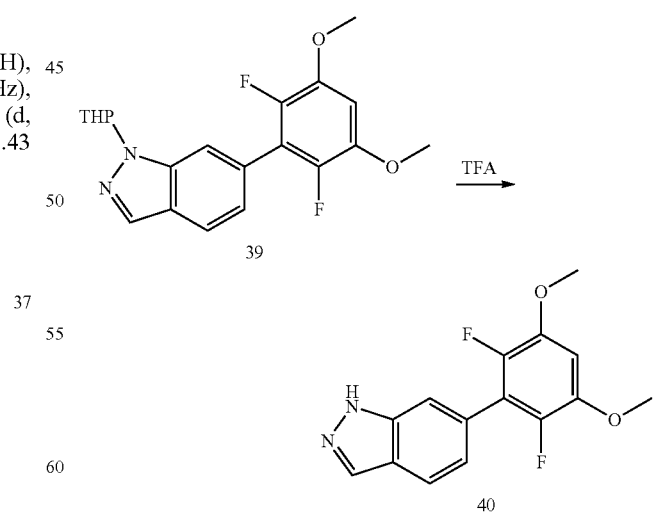

Compound 39 (629 mg, 1.68 mmol) and dichloromethane (10.0 mL) were added to a dry 50 mL round-bottom flask, and TFA (2 mL) was slowly added dropwise in ice bath, stirred at room temperature for 3.0 h. The solvent was rotary evaporated and the residue is diluted with iced water, and pH was adjusted to 8 with saturated NaHCO₃, extracted with ethyl acetate, and the organic phase was washed with water. Dried over anhydrous sodium sulfate, and the solvent was rotary evaporated to obtain the crude product compound 40 (460 mg, 94%). LCMS: 291.0 (M+H)⁺, RT=1.233 min.

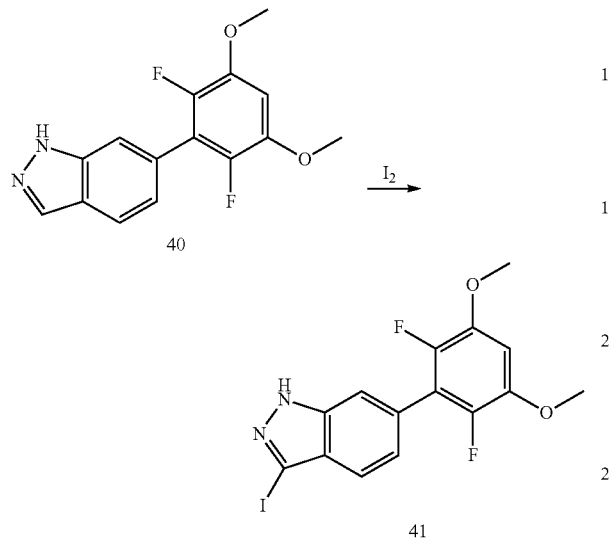

Compound 40 (460 mg, 1.59 mmol), NaOH aqueous solution (5.3 mL, 3N) and 1,4-dioxane (6.0 mL) were added to a dry 50 mL round-bottom flask. Iodine (484.0 mg, 1.90 mmol) in 1,4-dioxane was added dropwise at 0° C. Stirred at room temperature for 18 h. Washed with saturated sodium thiosulfate, and extracted with ethyl acetate, and the organic phase was washed successively with water and saturated brine, dried over anhydrous sodium sulfate and rotatory dried to give crude product 41 (633.0 mg, 95.6%) which was used without further purification in the next step. LCMS: 416.9 (M+H)⁺, RT=1.540 min.

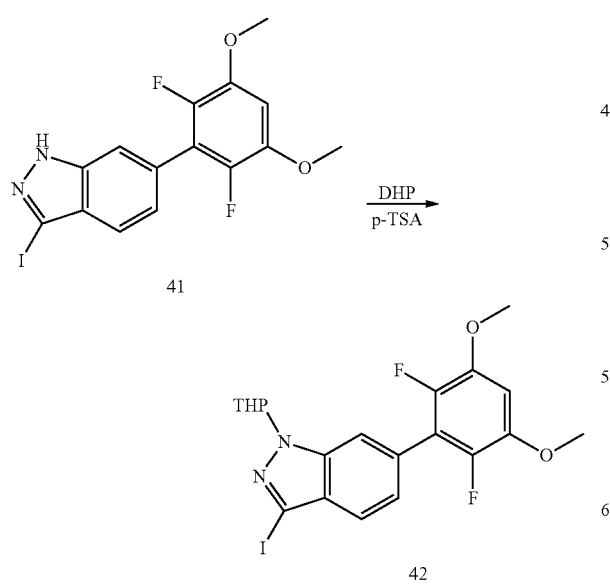

Compound 41 (633.0 mg, 1.52 mmol), p-TSA (58.0 mg, 0.30 mmol) and dichloromethane (6.0 mL) were added to a dry 50 mL round-bottom flask, and DHP (256.0 mg, 3.04 mmol) was slowly added dropwise, stirred at room temperature for 18.0 h. The reaction solution was diluted with 20.0 mL of water and extracted twice with 200 mL of dichloromethane. The organic phases were combined and dried over anhydrous sodium sulfate and the solvent was rotary dried to give the crude product, which was purified by column chromatography (ethyl acetate:petroleum ether=1:12) to give compound 42 (260.0 mg, 34%).

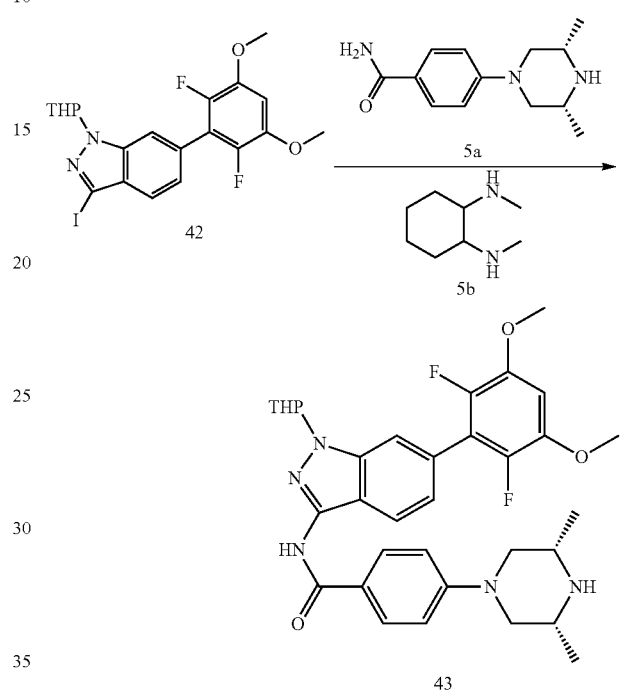

42 (260 mg, 0.52 mmol), 5a (145 mg, 0.62 mmol), 5b (148.0 mg, 1.04 mmol), K₃PO₄ (331.0 mg, 1.56 mmol), CuI (99 mg, 0.52 mmol), and dried DMF (3.0 mL) were added into a dry 25 mL three-neck flask, and stirred under 120° C. for 6.0 h. The reaction mixture was diluted with 20.0 mL of water, and extracted with ethyl acetate. The combined organic phase was washed successively with water and saturated brine, dried over anhydrous sodium sulfate and rotatory dried to give crude product 43 (290 mg, 92%) which was used without further purification in the next step. LCMS: 606.1 (M+H)⁺, RT=1.063 min.

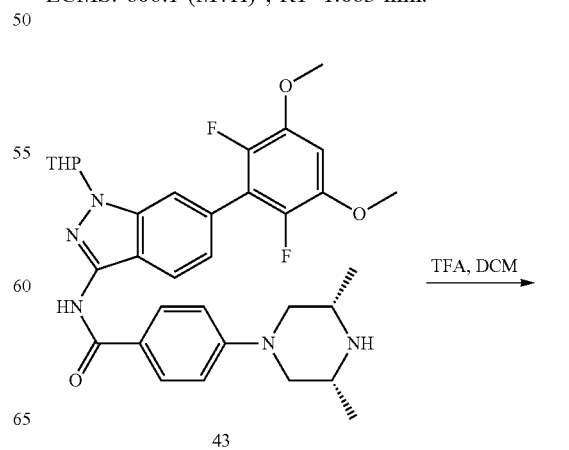

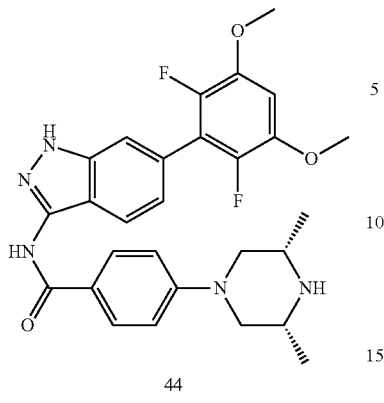

44

43 (290.0 mg, 0.48 mmol) and dichloromethane (10.0 mL) were added to a dry 25 mL round-bottom flask, and TFA (2.0 mL) was slowly added dropwise in ice bath, and stirred at room temperature for 4.0 h. The solvent was rotary dried to give the crude product, which was subjected to acidic prep-HPLC to give compound 44 (50.2 mg, 21%, TFA salt). LCMS: 522.1 (M+H)$^+$, RT=1.227 min.

$^1$H NMR (d6-DMSO, 400 MHz) δ ppm 12.91 (brs, 1H), 10.64 (d, 1H, J=3.2 Hz), 9.01 (m, 1H), 8.45 (m, 1H), 8.04 (d, 2H, J=8.8 Hz), 7.78 (d, 1H, J=8.4 Hz), 7.52 (s, 1H), 7.09 (m, 4H), 4.12 (d, 2H, J=13.8 Hz), 3.92 (s, 6H), 2.77 (m, 3H), 10.29 (d, 6H, J=6.4 Hz).

The following compounds were obtained by similar methods:

N-(6-(2,6-difluoro-3,5-dimethoxyphenyl)-1H-indazole-3-yl)-4-(4-methylpiperazine-1-yl)benzamide

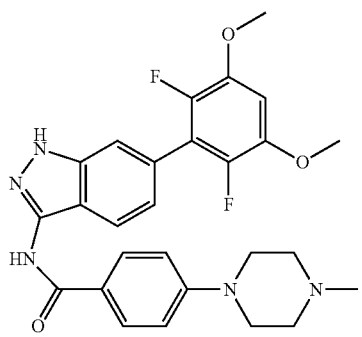

45

$^1$H NMR (d6-DMSO, 400 MHz) δ ppm 12.95 (s, 1H), 10.62 (s, 1H), 9.78 (s, 1H), 8.04 (d, 2H, J=8.8 Hz), 7.79 (d, 1H, J=8.4 Hz), 7.52 (s, 1H), 7.02-7.18 (m, 4H), 4.08 (d, 2H, J=12.0 Hz), 3.92 (s, 6H), 3.47-3.63 (m, 2H), 3.01-3.27 (m, 4H), 2.88 (s, 3H).

N-(6-(2,6-difluoro-3,5-dimethoxyphenyl)-1H-indazole-3-yl)-4-(3,3-dimethylpiperazine-1-yl)benzamide

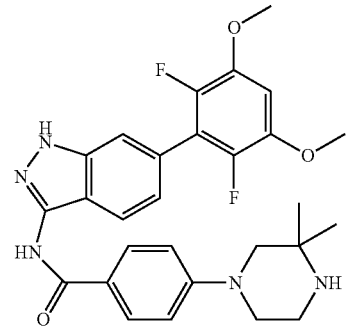

46

$^1$H NMR (d6-DMSO, 400 MHz) δ ppm 12.91 (s, 1H), 10.63 (s, 1H), 8.91 (s, 2H), 8.03 (d, 2H, J=9.2 Hz), 7.78 (d, 1H, J=8.0 Hz), 7.52 (s, 1H), 7.02-7.16 (m, 4H), 3.86 (s, 6H), 3.51 (m, 2H), 30.43 (m, 2H), 3.30 (s, 2H), 10.26 (t, 3H, J=7.2 Hz).

$^1$N-(6-(2,6-difluoro-3,5-dimethoxyphenyl)-1H-indazole-3-yl)-4-(4-ethylpiperazine-1-yl)benzamide

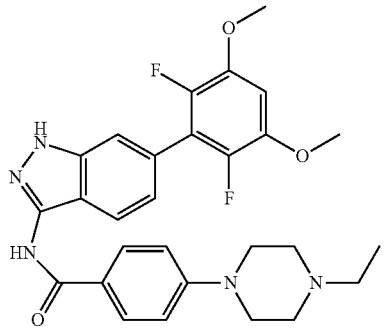

47

$^1$H NMR (d6-DMSO, 400 MHz) δ ppm 12.95 (s, 1H), 10.62 (s, 1H), 9.78 (s, 1H), 8.04 (d, 2H, J=8.8 Hz), 7.79 (d, 1H, J=8.4 Hz), 7.52 (s, 1H), 7.02-7.18 (m, 4H), 4.08 (d, 2H, J=12.0 Hz), 3.92 (s, 6H), 3.47-3.63 (n, 2H), 3.21-3.22 (m, 2H), 3.01-3.27 (m, 4H), 1.27 (t, 3H, J=7.2 Hz).

N-(6-(2,6-difluoro-3,5-dimethoxyphenyl)-1H-pyrazolo[3,4-b]pyridine-3-yl)-4-(4-methylpiperazine-1-yl)benzamide

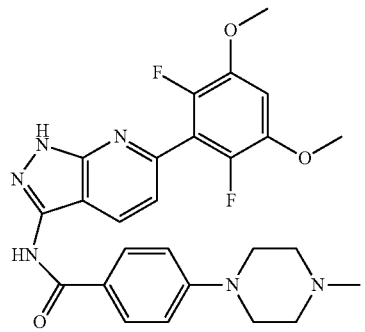

48

¹H NMR (d-MeOD, 400 MHz) δ ppm 8.50 (d, 1H, J=8.4 Hz)), 7.99 (d, 2H, J=8.8 Hz), 7.30 (d, 1H, J=8.4 Hz), 7.08 (d, 2H, J=8.8 Hz), 7.01 (s, 1H), 3.93 (s, 6H), 3.45 (s, 4H), 2.80 (s, 4H), 2.49 (s, 3H). LC MS: 509 (M+H)⁺, RT=1.18 min.

Synthetic Route III

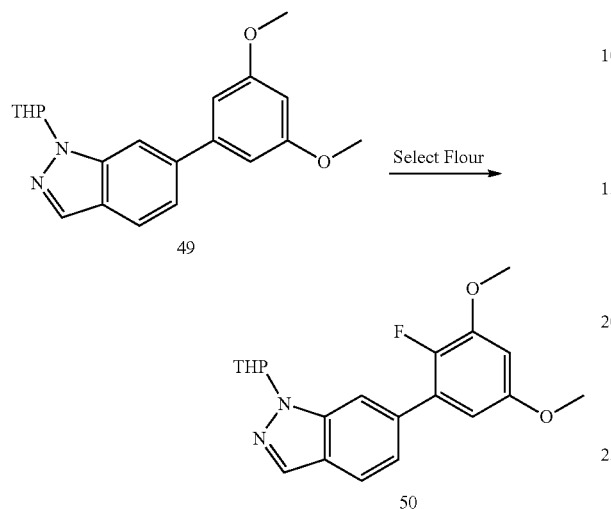

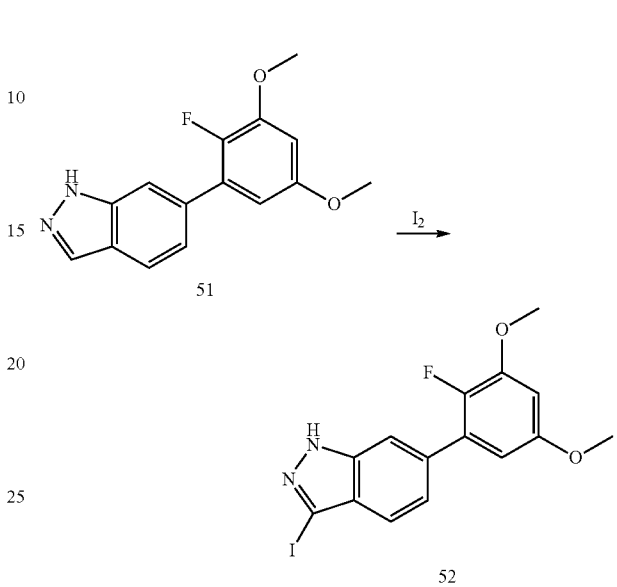

Compound 49 (1.20 g, 3.55 mmol) and acetonitrile (20.0 mL) were added to a dry 50 mL round-bottom flask. Under the protection of N₂, Select Flour (2.51 g, 7.1 mmol) was added in batches at 0° C., and stirred at room temperature for 18.0 h. The reaction solution was diluted with water and extracted with ethyl acetate. The organic phase was successively washed with water, saturated NaHCO₃, and saturated brine. Dried over anhydrous sodium sulfate, and the solvent was rotary evaporated to obtain the crude product, which was purified by column chromatography (ethyl acetate: petroleum ether=1:8) to give the crude product compound 50 (629 mg, 47%). LCMS: 374.9 (M+H)⁺, RT=1.243 min.

value was adjusted to 8 with saturated NaHCO3, and the mixture was extracted with ethyl acetate. The organic phase was washed with water. Dried over anhydrous sodium sulfate, and the solvent was rotary evaporated to obtain crude product compound 51 (460 mg, 95%). LCMS: 291.0 (M+H)⁺, RT=1.233 min.

Compound 51 (460 mg, 1.59 mmol), NaOH aqueous solution (5.3 mL, 3N) and 1,4-dioxane (6.0 mL) were added to a dry 50 mL round-bottom flask. Iodine (484.0 mg, 1.90 mmol) in 1,4-dioxane was added dropwise at 0° C. The mixture was stirred at room temperature for 18 h, washed with saturated sodium thiosulfate, and extracted with ethyl acetate. The organic phase was washed successively with water and saturated brine, dried over anhydrous sodium sulfate and rotatory dried to give crude product 52 (633.0 mg, 96%) which was used without further purification in the next step. LCMS: 416.9 (M+H)⁺, RT=1.540 min.

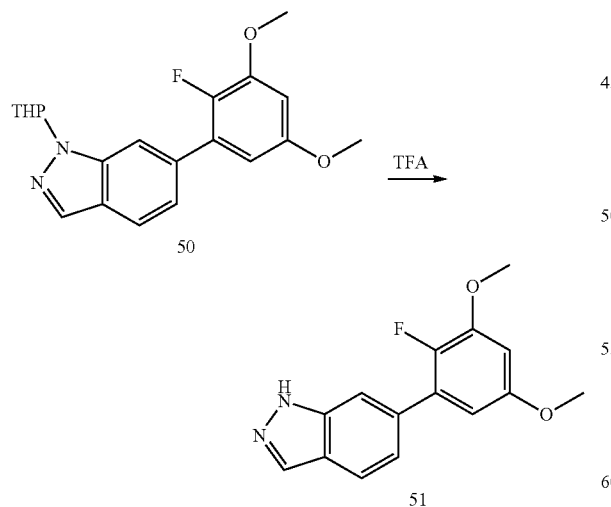

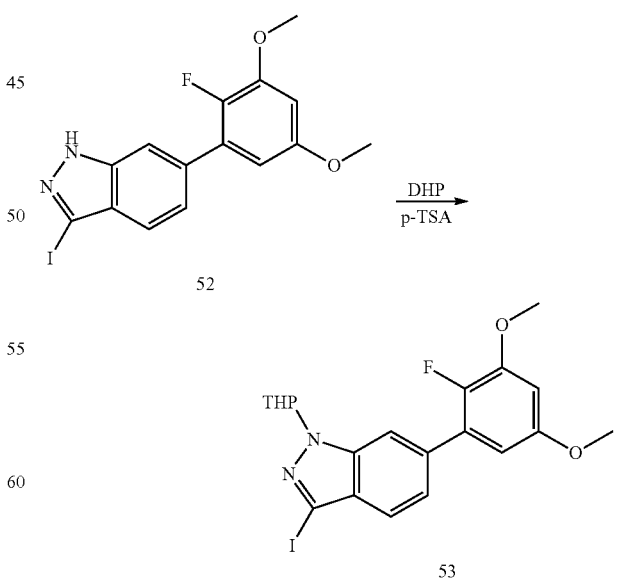

50 (629 mg, 1.68 mmol) and dichloromethane (10.0 mL) were added to a dry 50 mL round-bottom flask, and TFA (2 mL) was slowly added dropwise in ice bath, and stirred at room temperature for 3.0 h. The solvent was rotary evaporated and the residue was diluted with iced water. The pH Compound 52 (633.0 mg, 1.52 mmol), p-TSA (58.0 mg, 0.30 mmol) and dichloromethane (6.0 mL) were added to a dry 50 mL round-bottom flask, and DHP (256.0 mg, 3.04 mmol) was slowly added dropwise, stirred at room temperature for 18.0 h. The reaction solution was diluted with 20.0 mL of water and extracted with dichloromethane. The organic phases were combined and dried over anhydrous sodium sulfate and the solvent was rotary dried to give the crude product, which was purified by column chromatography (ethyl acetate:petroleum ether=1:12) to give compound 53 (265.0 mg, 26%).

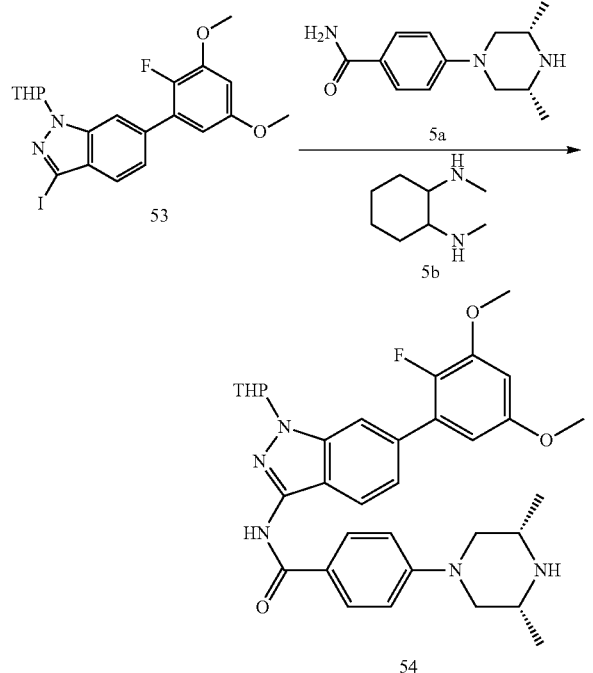

53 (193 mg, 0.40 mmol), 5a (112 mg, 0.48 mmol), 5b (114.0 mg, 0.81 mmol), K$_3$PO$_4$ (256.0 mg, 1.21 mmol), CuI (76 mg, 0.40 mmol), and dried DMF (3.0 mL) were added into a dry 25 mL three-neck flask, and stirred at 120° C. for 6.0 h. The reaction mixture was diluted with 30.0 mL of water, and extracted with ethyl acetate. The combined organic phase was washed successively with water and saturated brine, dried over anhydrous sodium sulfate and rotatory dried to give crude product 54 (240 mg, 99%) which was used without further purification in the next step. LCMS: 588.1 (M+H)$^+$, RT=1.320 min.

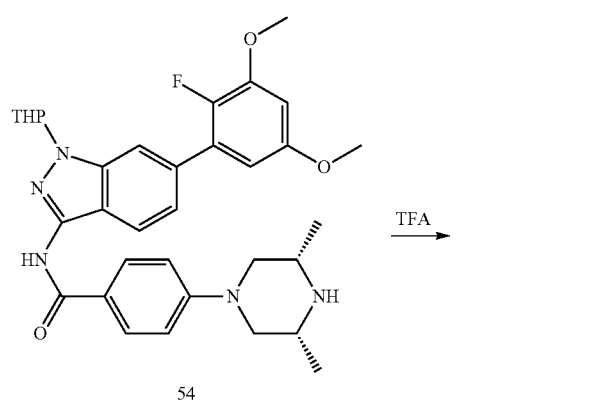

-continued

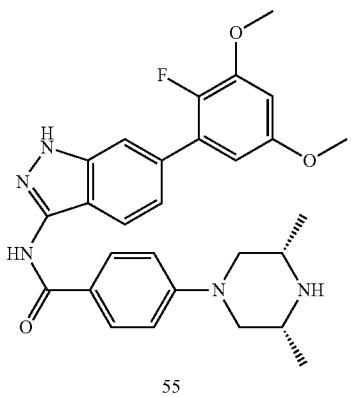

54 (240.0 mg, 0.41 mmol) and dichloromethane (7.5 mL) were added to a dry 25 mL round-bottom flask, and TFA (1.5 mL) was slowly added dropwise in ice bath, stirred at room temperature for 4.0 h. The solvent was rotary dried to give the crude product, which was subjected to acidic prep-HPLC to give compound 55 (70.8 mg, 34%, TFA salt). LCMS: 522.1 (M+H)$^+$, RT=1.227 min.

$^1$H NMR (d6-DMSO, 400 MHz) δ ppm 12.95 (brs, 1H), 10.61 (s, 1H), 9.17 (m, 1H), 8.57 (m, 1H), 8.03 (d, 2H, J=9.2 Hz), 7.76 (m, 1H), 7.59 (s, 1H), 7.22 (d, 1H, J=8.8 Hz), 7.13 (d, 2H, J=9.2 Hz), 6.76 (dd, 1H, J$_1$=2.8 Hz, J$_2$=6.8 Hz), 6.61 (m, 1H), 4.01 (d, 2H, J=12.4 Hz), 3.88 (s, 1H), 3.84 (s, 31H), 3.81 (s, 3H), 3.30-3.50 (m, 21H), 2.75 (t, 2H, J=6.4 Hz), 1.29 (d, 6H, J=6.4 Hz).

Synthetic Route IV

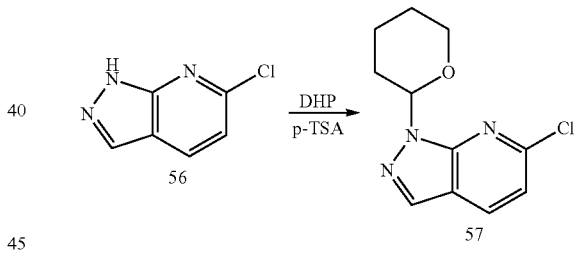

Compound 56 (10.00 g, 51.0 mmol), p-TSA (1.75 g, 10.2 mmol) and dichloromethane (100.0 mL) were added to a dry 250 mL round-bottom flask, and DHP (8.56 g, 102.0 mmol) was slowly added dropwise, stirred at room temperature for 4.0 h. After the reaction was completed, the solution was diluted with 100.0 mL of water and extracted twice with 200 mL of dichloromethane. The organic phases were combined and dried over anhydrous sodium sulfate and the solvent was rotary dried to give compound 57 (8.90 g, 62%). LCMS: 281 (M+H)$^+$, RT=1.626 min.

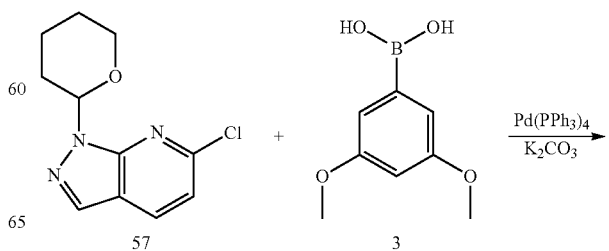

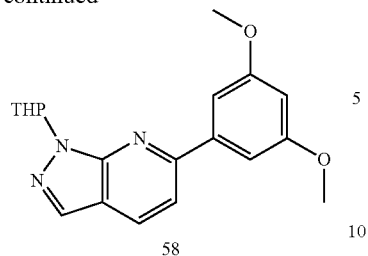

58

Compound 57 (8.90 g, 31.7 mmol), 3 (5.77 g, 31.7 mmol), Pd(PPh₃)₄ (3.66 g, 3.17 mmol), K₂CO₃ (8.75 g, 63.4 mmol), 1,4-dioxane (60.0 mL) and water (15.0 mL) were added successively into a 250 mL dry round-bottom flask at room temperature, and stirred evenly. The reaction was heated to reflux for 4.0 h under the protection of nitrogen. The reaction solution was cooled to room temperature, and the solvent was rotary evaporated to obtain the crude product, which was purified by column chromatography (ethyl acetate: petroleum ether=1:10) to give compound 58 (8.10 g, 76%). LCMS: 339 (M+H)⁺, RT=1.626 min.

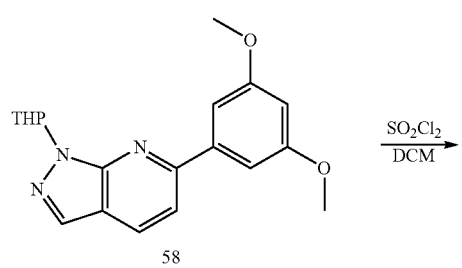

58

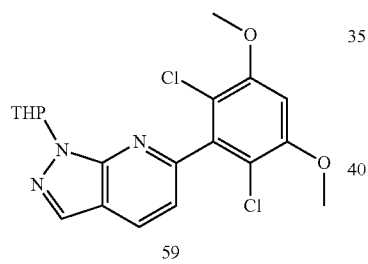

59

Compound 58 (7.90 g, 23.4 mmol) and dichloromethane (50.0 mL) were added to a dry 250 mL round-bottom flask, and SO₂Cl₂ (7.15 g, 46.7 mmol) was slowly added dropwise, stirred at room temperature for 4.0 h. The reaction solution was diluted with 50.0 mL of water, extracted twice with 200 mL of dichloromethane, and washed with saturated NaHCO₃ solution. The organic phases were combined and dried over anhydrous sodium sulfate and the solvent was rotary dried to give compound 59 (8.50 g, 89%). LCMS: 407 (M+H)⁺, RT=1.798 min.

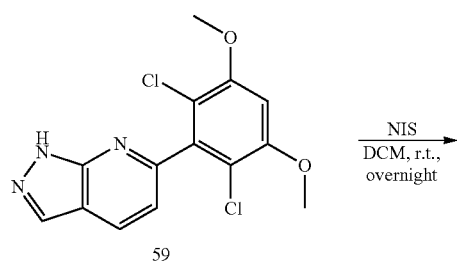

59

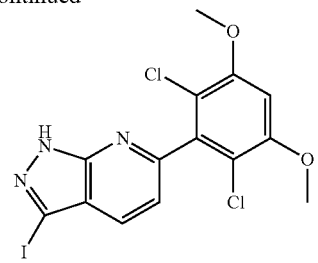

60

Compound 59 (0.972 g, 3 mmol), NIS (1.6 g, 7 mmol) and DCM (10.0 mL) were added to a dry 250 mL round-bottom flask. The reaction mixture was stirred at room temperature for 2.0 hours. After completion of the reaction, the reaction solution was added with 200 mL of water and extracted twice with 200 mL dichloromethane. The organic phases were washed with saturated sodium thiosulfate, combined and dried over anhydrous sodium sulfate, and the solvent was rotary dried to give compound 60 (1.1 g, 82%). LCMS: 450 (M+H)+, RT=1.644 min.

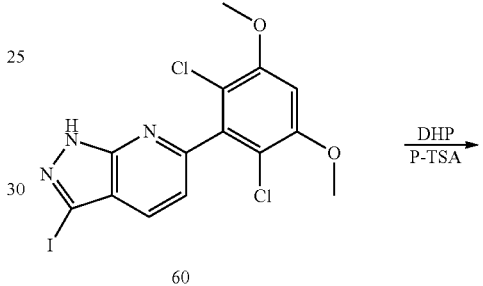

60

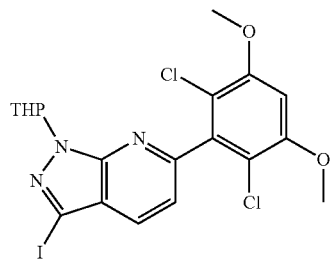

61

60 (9.30 g, 20.76 mmol), p-TSA (0.71 g, 4.152 mmol) and dichloromethane (50.0 mL) were added to a dry 250 mL round-bottom flask, and DHP (3.48 g, 41.52 mmol) was slowly added dropwise, stirred at room temperature for 4.0 h. The reaction solution was diluted with 50.0 mL of water and extracted twice with 200 mL of dichloromethane. The organic phases were combined and dried over anhydrous sodium sulfate and the solvent was rotary dried to give compound 61 (7.70 g, 70%). LCMS: 281 (M+H)⁺, RT=2.165 min.

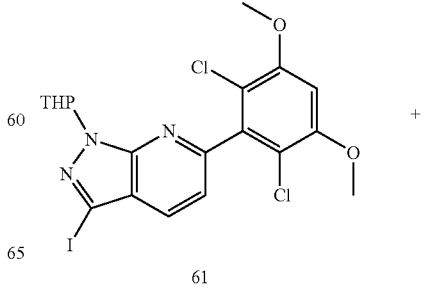

61

-continued

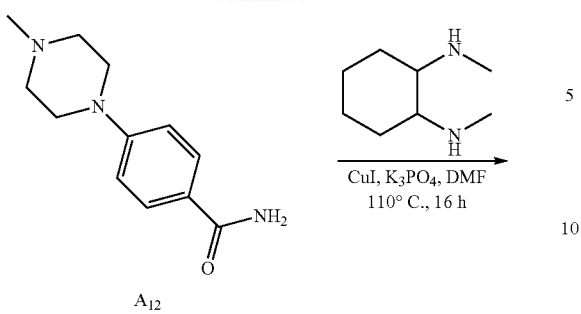

Compound 61 (2.0 g, 3.75 mmol) was dissolved in 20 mL of anhydrous DMF, and trans-N, N'-dimethyl-1,2-cyclohexanediamine (107 mg, 0.75 mmol), CuI (36 mg, 0.19 mmol), K₃PO₄ (1.6 g, 7.5 mmol) and A₁₂ (1.05 g, 4.5 mmol) were successively added into the solution at room temperature. It was purged with nitrogen for three times, heated to 110° C., and stirred for 16 hours. After completion of the reaction, the solvent was rotary evaporated to obtain the crude product, which was purified by column chromatography (dichloromethane:methanol=40:1) to give white solid (0.98 g), yield 41%.

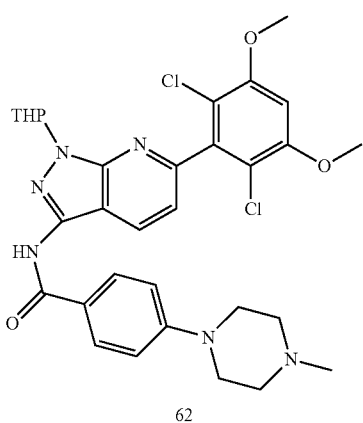

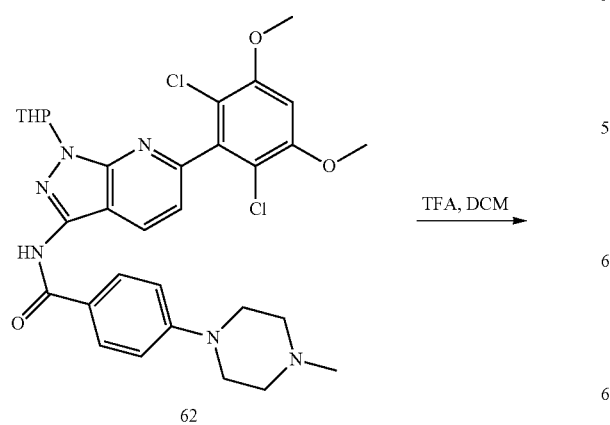

-continued

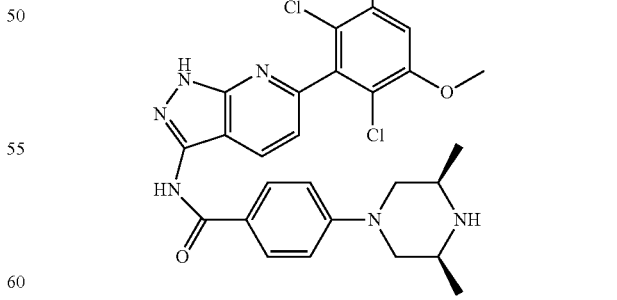

Compound 62 (0.86 g, 1.35 mmol) was dissolved in 10 mL of dichloromethane, and trifluoroacetic acid (5 mL) was added to the solution at room temperature. The mixture was stirred at room temperature for 4 hours. After completion of the reaction, the solvent was rotary evaporated to obtain the crude product, which was purified by column chromatography (dichloromethane:methanol=20:1) to give white solid 63 (0.618 g), yield 82%.

N-(6-(2,6-dichloro-3,5-dimethoxyphenyl)-1H-pyrazolo [3,4-b]pyridin-3-yl)-4-(4-methylpiperazine-1-yl)benzamide ¹H NMR (d6-DMSO, 400 MHz) δ ppm 13.37 (s, 1H), 10.81 (s, 1H), 8.39 (d, 1H, J=8.4 Hz), 8.01 (d, 2H, J=8.8 Hz), 7.08-7.02 (m, 4H), 3.98 (s, 6H), 3.32 (m, 4H), 2.45 (m, 4H), 2.23 (s, 3H).

The following compounds were obtained by similar methods:

N-(6-(2,6-dichloro-3,5-dimethoxyphenyl)-1H-pyrazolo [3,4-b] pyridin-3-yl)-4-((3S,5R)-3,5-dimethyl-piperazine-1-yl)benzamide ¹H NMR (CDCl₃, 400 MHz) δ ppm 10.76 (br s, 1H), 8.97 (s, 1H), 8.87 (d, 1H, J=8.4 Hz), 7.90 (d, 2H, J=8.8 Hz), 7.16 (d, 1H, J=8.4 Hz), 6.95 (d, 2H, J=8.8 Hz), 6.66 (s, 1H), 3.97 (s, 6H), 3.70 (d, 2H, J=12.0 Hz), 3.02 (m, 2H), 2.46 (t, 2H, J=11.2 Hz), 1.16 (d, 6H, J=6.4 Hz).

89

N-(6-(2,6-dichloro-3,5-dimethoxyphenyl)-1H-pyrazolo [3,4-b] pyridin-3-yl)-4-(4-ethylpiperazine-1-yl)benzamide

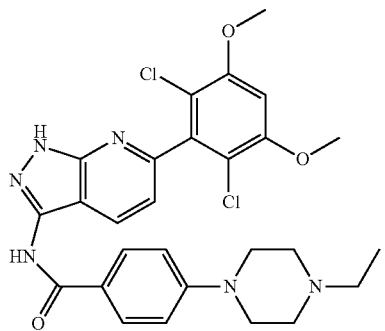

65

¹H NMR (CDCl₃, 400 MHz) δ ppm 10.13 (s, 1H), 8.86 (d, 1H, J=8.4 Hz), 8.66 (s, 1H), 7.90 (d, 2H, J=8.8 Hz), 7.16 (d, 1H, J=8.4 Hz), 6.95 (d, 2H, J=8.8 Hz), 6.67 (s, 1H), 3.97 (s, 6H), 3.41-3.79 (m, 4H), 2.64-2.60 (m, 4H), 2.49 (q, 2H, J=7.2 Hz), 1.15 (t, 3H, J=7.2 Hz)

90

N-(6-(2,6-dichloro-3,5-dimethoxyphenyl)-1H-pyrazolo[3,4-b] pyridin-3-yl)-4-(4-(dimethylamino)piperidine-1-yl)benzamide

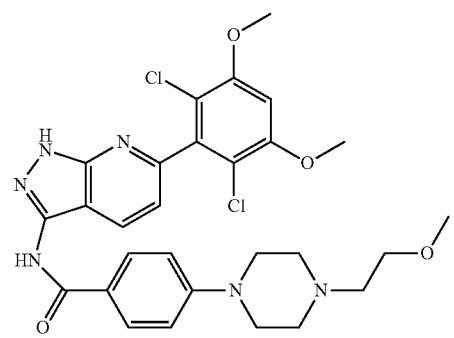

67

¹H NMR (d6-DMSO, 400 MHz) δ ppm 10.81 (s, 1H), 8.381 (d, 1H, J=8.4 Hz), 8.00 (d, 2H, J=8.8 Hz), 7.01-7.07 (m, 4H), 3.99 (s, 6H), 3.49-3.51 (m, 3H), 3.26 (s, 4H), 3.17 (s, 3H), 2.55-2.58 (m, 5H). LCMS: 585 (M+H)⁺, RT=1.225 min.

N-(6-(2,6-dichloro-3,5-dimethoxyphenyl)-1H-pyrazolo [3,4-b] pyridin-3-yl)-4-((3R,5S)-3,5-dimethylpiperazine-1-yl)benzamide

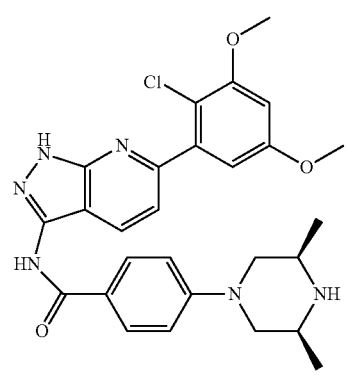

66

¹H NMR (d6-DMSO, 400 MHz) δ ppm 13.36 (s, 1H), 10.77 (s, 1H), 8.34 (d, 1H, J=8.4 Hz), 7.98 (d, 2H, J=8 Hz), 7.30 (d, 1H, J=8 Hz), 7.00 (d, 2H, J=8.8 Hz), 6.82 (d, 1H, J=2.8 Hz), 6.73 (d, 1H, J=2.8 Hz), 3.91 (s, 3H), 3.84 (s, 3H), 3.75 (d, 2H, J=10.4 Hz), 2.81 (s, 2H), 2.26 (s, 1H), 2.22 (d, 2H, J=11.2 Hz), 1.04 (s, 3H), 1.03 (s, 3H). LCMS: 521 (M+H)+, RT=1.233 min.

N-(6-(3,5-dimethoxyphenyl)-1H-pyrazolo [3,4-b] pyridin-3-yl)-4-(((3R,5S)-3,5-dimethylpiperazine-1-yl))benzamide

68

¹H NMR (d6-DMSO, 400 MHz) δ ppm 13.34 (s, 1H), 10.77 (s, 1H) 8.36 (d, 1H, J=8.8 Hz), 7.98 (d, 2H, J=8.8 Hz), 7.74 (s, 1H), 7.31 (d, 2H, J=1.6 Hz), 7.00 (d, 2H, J=8.8 Hz), 6.62 ((s, 1H), 3.84 (s, 6H), 3.75 (d, 2H, J=11.2 Hz), 2.81 (s, 2H), 2.26 (s, 1H), 2.22 (d, 2H, J=10.8 Hz), 1.04 (d, 6H, J=6 Hz). LCMS: 487 (M+H)+, RT=1.113 min.

N-(6-(2,6-dichloro-3,5-dimethoxyphenyl)-1H-pyrazolo [3,4-b] pyridin-3-yl)pyridine formamide

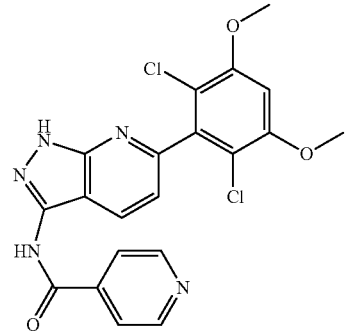

¹H NMR (d6-DMSO, 400 MHz) δ ppm 8.74 (s, 2H), 8.41 (d, 1H, J=8.0 Hz), 8.02 (d, 2H, J=5.6 Hz), 7.04 (s, 2H), 3.98 (s, 6H). LCMS: 445 (M+H)⁺, RT=1.409 min.

N-(6-(2,6-dichloro-3,5-dimethoxyphenyl)-1H-pyrazolo [3,4-b]pyridin-3-yl)-4-morpholino benzamide

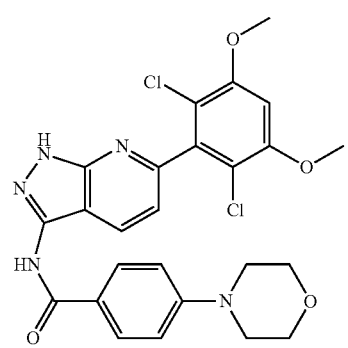

¹H NMR (d6-DMSO, 400 MHz) δ ppm 13.42 (s, 1H), 10.86 (s, 1H), 8.41 (d, 1H, J=7.2 Hz), 8.05 (s, 3H), 7.07 (s, 4H), 4.00 (s, 6H), 3.77 (s, 4H), 3.30 (s, 4H). LCMS: 528 (M+H)⁺. RT=1.643 min.

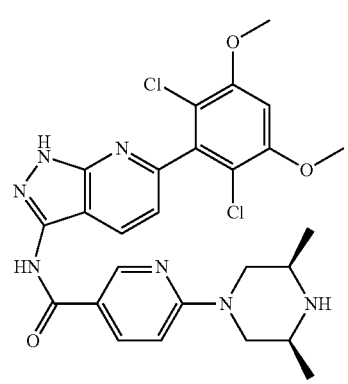

¹H NMR (d6-DMSO, 400 MHz) δ ppm 13.47 (brs, 1H), 11.03 (s, 1H), 9.28 (s, 1H), 8.89 (s, 1H), 8.71 (s, 1H), 8.41 (d, J=8.0 Hz, 1H), 8.28-8.30 (m, 1H), 7.05-7.12 (m, 3H), 4.66 (d, J=9.2 Hz, 2H), 3.98 (s, 6H), 3.46 (brs, 2H), 2.83-2.92 (m, 2H), 1.30 (d, J=6.4 Hz, 6H).

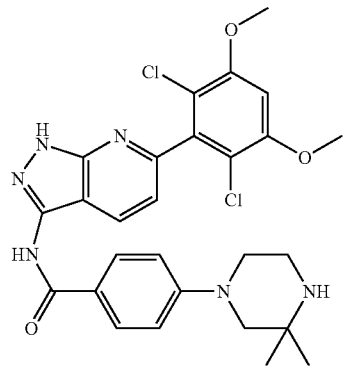

¹H NMR (d-MeOD, 400 MHz) δ ppm 8.52 (d, J=8.0 Hz, 1H), 8.03 (d, J=8.0 Hz, 2H), 7.15-7.13 (m, 3H), 6.94 (s, 1H), 3.99 (s, 6H), 3.58-3.57 (m, 2H), 3.44-3.40 (m, 4H), 10.50 (s, 6H).

N-(6-(2,6-dichloro-3,5-dimethoxyphenyl)-1H-pyrazolo [3,4-b] pyridin-3-yl)-4-(2,6-diazaspiro [3.3] heptane-2-yl)benzamide

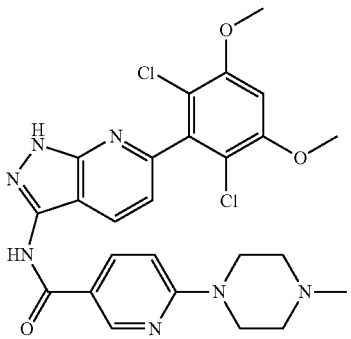

¹H NMR (d-MeOD, 400 MHz) δ ppm 8.49 (d, 1H, J=8.4 Hz), 7.94 (d, 2H, J=8.8 Hz), 7.12 (d, 1H, J=8.4 Hz), 6.94 (S, 1H), 6.55 (d, 2H, J=8.4 Hz), 4.08 (S, 4H), 3.98 (S, 6H), 3.83 (S, 4H).

N-(6-(2,6-dichloro-3,5-dimethoxyphenyl)-1H-pyrazolo [3,4-b]pyridin-3-yl)-6-(4-methylpiperazine-1-yl)nicotinamide ¹H NMR (DMSO-d6, 400 MHz) δ ppm 8.84 (s, 1H), 8.37 (d, 1H, J=8.4 Hz), 8.20 (d, 1H, J=7.6 Hz), 7.03 (s, 2H), 6.92 (d, 1H, J=8.8 Hz), 3.98 (s, 6H), 3.63 (s, 4H), 2.41 (t, 4H, J=4.0 Hz), 2.22 (s, 3H). LCMS: 542.2 [M+H]⁺, RT=1.18 min.

N-(6-(2,6-dichloro-3,5-dimethoxyphenyl)-1H-pyrazolo [3,4-b]pyridin-3-yl)-6-(4-ethylpiperazine-1-yl) nicotinamide

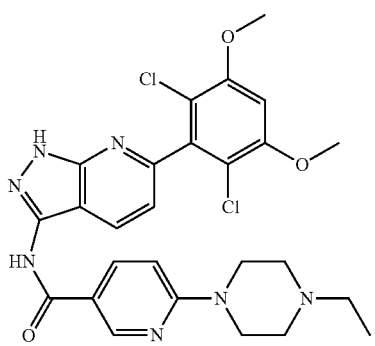

86

1H NMR (DMSO-d6, 400 MHz) δ ppm 13.40 (s, 1H), 10.91 (s, 1H), 8.84 (d, 1H, J=2.4 Hz), 8.41 (d, 1H, J=8.4 Hz), 8.19 (dd, 1H, J₁=J₂=2.4 Hz), 7.09 (t, 2H, J=12.4 Hz), 6.93 (d, 1H, J=9.2 Hz), 3.98 (s, 6H), 3.65 (t, 4H, J=3.6 Hz), 2.45 (t, 4H, J=4.8 Hz), 2.39 (q, 2H, J=7.2 Hz), 1.05 (t, 3H, J=6.8 Hz) LCMS: 556.2 [M+H]⁺, RT=1.19 min.

N-(6-(2,6-dichloro-3,5-dimethoxyphenyl)-1H-pyrazolo [3,4-b]pyridin-3-yl)-6-(3,3-dimethylpiperazine-1-yl)nicotinamide

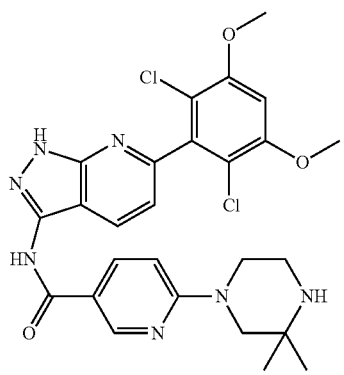

87

¹H NMR (DMSO-d6, 400 MHz) δ ppm 13.39 (s, 1H), 10.86 (s, 1H), 8.81 (d, 1H, J=2.0 Hz), 8.40 (d, 1H, J=8.0 Hz), 8.16 (dd, 1H, J₁=2.4 Hz, J₂=2.4 Hz), 7.08 (t, 2H, J=8.4 Hz), 6.90 (d, 1H, J=9.2 Hz), 3.99 (s, 6H), 3.60 (t, 2H, J=4.0 Hz), 3.43 (s, 2H), 2.82 (t, 2H, J=4.4 Hz), 1.04 (s, 6H). LCMS: 556.2 [M+H]⁺, RT=1.21 min.

6-(4-cyclopropylpiperazine-1-yl)-N-(6-(2,6-dichloro-3,5-dimethoxyphenyl)-1H-pyrazolo [3,4-b] pyridin-3-yl)nicotinamide

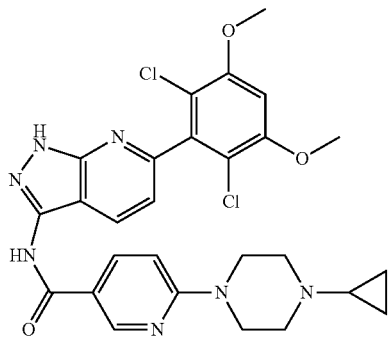

88

1H NMR (DMSO-d6, 400 MHz) δ ppm 13.40 (s, 1H), 10.92 (s, 1H), 8.85 (d, 1H, J=1.6 Hz), 8.41 (d, 1H, J=8.4 Hz), 8.20 (dd, 1H, J₁=2.0 Hz, J₂=1.6 Hz), 7.08 (t, 2H, J=8.0 Hz), 6.94 (d, 1H, J=9.2 Hz), 3.98 (s, 6H), 3.62 (s, 4H), 2.62 (s, 4H), 1.66 (d, 1H, J=3.6 Hz), 0.46 (d, 2H, J=4.4 Hz), 0.38 (d, 2H, J=2.4 Hz). LCMS: 568.2 [M+H]⁺, RT=1.21 min.

N-(6-(2,6-dichloro-3,5-dimethoxyphenyl)-1H-pyrazolo [3,4-b] pyridin-3-yl)-4-(4-cyclopropylpiperidine-1-yl)benzamide

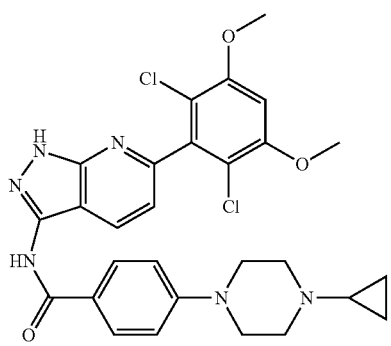

89

¹H NMR (d6-DMSO, 400 MHz) δ ppm 8.34 (d, 1H, J=8 Hz), 8.00 (d, 2H, J=8.8 Hz), 7.02 (t, 4H, J=7.8 Hz), 3.98 (s, 6H), 3.26 (s, 4H), 2.67 (s, 4H), 1.66 (s, 1H), 0.45 (d, 2H, J=4.8 Hz), 0.363 (s, 2H). LCMS: 567 (M+H)⁺. RT=1.22 min.

Synthetic Route V

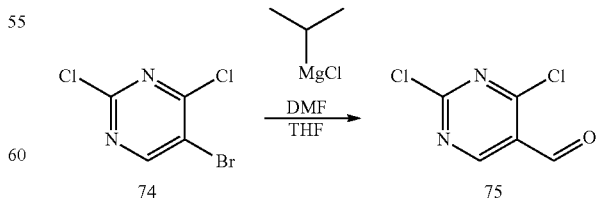

Under nitrogen protection, 74 (10.00 g, 43.9 mmol) and tetrahydrofuran (100.0 mL) were added into a dry 250 mL three-neck flask, and isopropylmagnesium chloride lithium chloride complex solution (2M) (24.2 mL, 48.3 mmol) was slowly added dropwise at −78° C., stirred at −78° C.-35° C.

for 0.5 hour, and then DMF (9.6 g, 131.6 mmol) was slowly added dropwise at −78° C., stirred at −35° C. for 4 hours. The reaction was quenched with saturated ammonium chloride solution at −78° C., and the reaction solution was diluted with 100.0 mL of water and extracted twice with 200 mL of ethyl acetate. The organic phases were combined and dried over anhydrous sodium sulfate and the solvent was rotary dried to give compound 75 (2.1 g, 31%) as white solid.

¹H NMR (DMSO-d6, 400 MHz) δ ppm 10.19 (s, 1H), 9.12 (s, 1H).

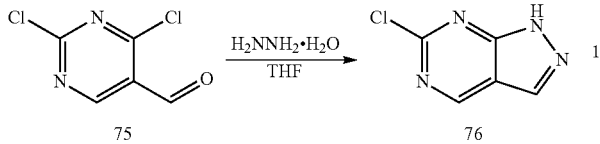

Compound 75 (2.0 g, 11.3 mmol) was dissolved in THF (10 mL), and hydrazine hydrate (1.33 g, 22.6 mmol) in THF (20 mL) was added at 0° C. The reaction was stirred at room temperature for 0.5 hour, and purified with silica gel column to provide compound 76 as yellow solid (1.0 g, 57%). LCMS: 155 (M+H)⁺, RT=0.929 min.

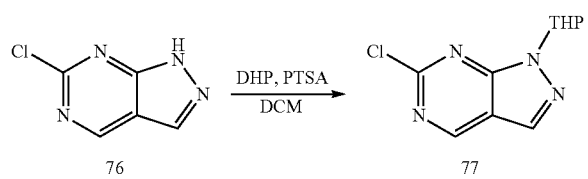

Compound 76 (1.0 g, 6.5 mmol), DHP (1.1 g, 13 mmol) and PTSA (224 mg, 1.3 mmol) were dissolved in 30 mL of methylene chloride overnight at room temperature, and the mixture was purified by column chromatography on silica gel to provide yellow solid compound 77 (1.0 g, 65%). LCMS: 239 (M+H)⁺, RT=1.32 min.

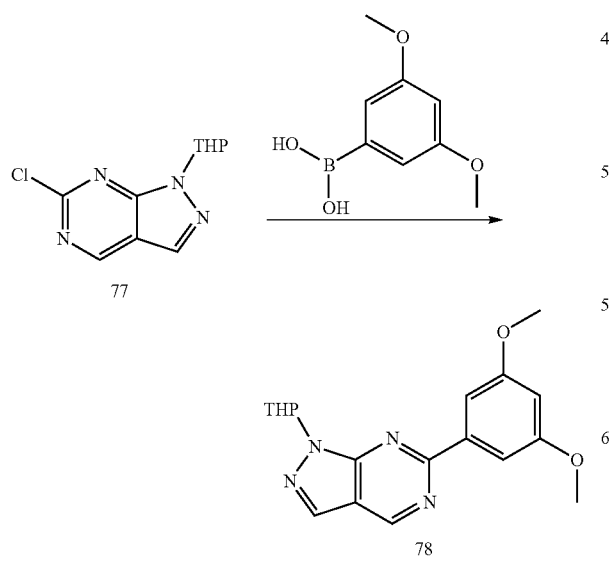

Compound 77 (900 mg, 3.8 mmol), 3,5-dimethoxyphenylboronic acid (826 mg, 4.5 mmol), Pd(dppf)Cl₂ (415 mg, 0.57 mmol) and potassium phosphate (960 mg, 4.5 mmol) were dissolved in 1,4-dioxane (12 mL), reacted under microwave at 110° C. for 90 minutes, and purified with silica gel column to provide yellow solid compound 78 (950 mg, 74%). LCMS: 341 (M+H)⁺, RT=1.803 min.

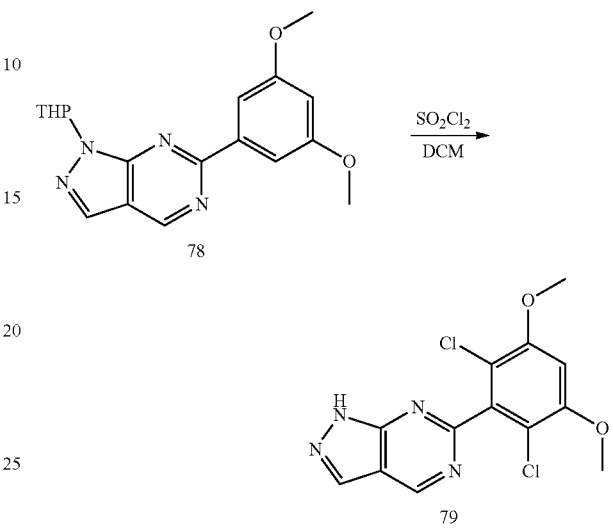

Compound 78 (500 mg, 1.5 mmol) was dissolved in 10 mL of methylene chloride. Sulfonyl chloride (446 mg, 3.3 mmol) was added at 0° C. and stirred at room temperature for 4 hours. LCMS showed no residual material. The reaction solution was quenched with a small amount of water, and purified with silica gel column to provide white solid Compound 79 (460 mg, 84%). LC MS: 325 (M+H)⁺, RT=1.24 min.

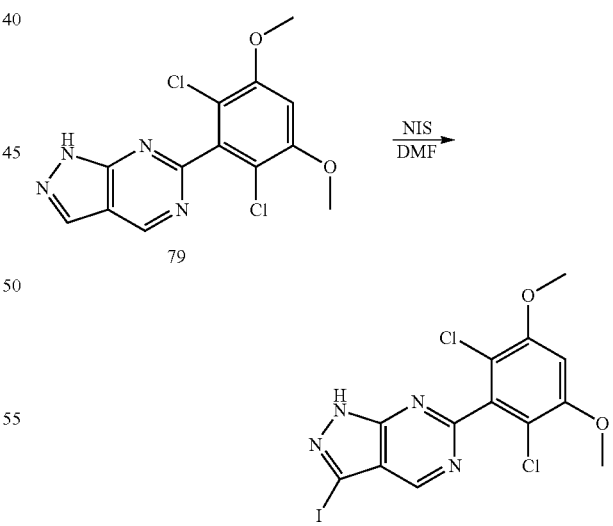

Compound 79 (400 mg, 1.23 mmol) and NIS (554 mg, 2.46 mmol) were dissolved in 5 mL of DMF at 80° C. overnight. The reaction mixture was rotary dried and purified over silica gel to provide compound 80 (370 mg, 67%). LCMS: 450 (M+H)⁺, RT=1.577 min.

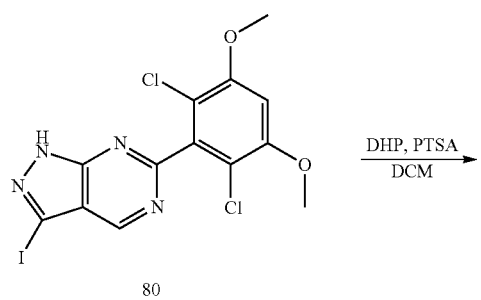

80

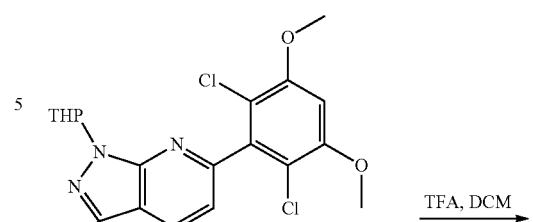

82

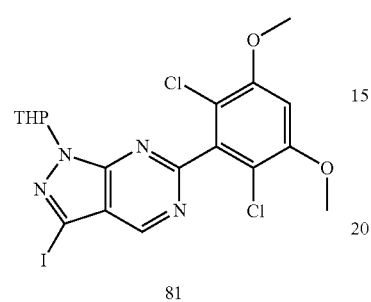

81

Compound 80 (370 mg, 0.82 mmol), DHP (138 mg, 1.64 mmol) and PTSA (28 mg, 0.16 mmol) were dissolved in 10 mL of dichloromethane, and stirred for 4 hours at room temperature. The mixture was purified by column to provide yellow solid compound 81 (450 mg, 100%). LCMS: 534 (M+H)⁺, RT=1.964 min.

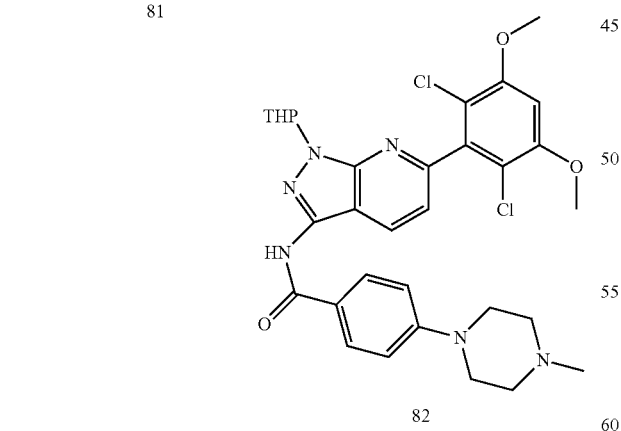

81

82

Compound 81 (100 mg, 0.19 mmol), 4-(4-methylpiperazin-1-yl)benzamide (82 mg, 0.37 mmol), CuI (7 mg, 0.037 mmol), K₃PO₄ (119 mg, 0.56 mmol) and N, N'-dimethyl-1,2-cyclohexanediamine (5 mg, 0.037 mmol) were dissolved in 3 mL of DMF, and stirred overnight at 110° C., rotary dried and column purified to provide brown oil compound 82, 55 mg, yield 47%. LCMS: 626 (M+H)⁺, RT=1.37 min.

83

Compound 82 (55 mg, 0.088 mmol) and 2 mL of trifluoroacetic acid were dissolved in 2 mL of dichloromethane overnight at room temperature. After the reaction was completed, the solvent was rotary evaporated to provide crude product, which was purified by pre-TLC and then pre-HPLC to obtain 4 mg of the yellow solid product 83, yield 8%. LCMS: 542 (M+H)⁺, RT=1.27 min.

¹H NMR (d-MeOD, 400 MHz) δ ppm 9.76 (s, 1H), 8.06 (d, 2H, J8.8 Hz), 7.16 (d, 2H, J=8.8 Hz), 6.96 (s, 1H), 4.13 (d, 2H, J=10 Hz), 3.99 (s, 6H), 3.63 (d, 2H, J=2.8 Hz), 3.21-3.17 (m, 4H), 2.99 (s, 3H).

The following compounds were obtained by similar methods:

N-(6-(2,6-dichloro-3,5-dimethoxyphenyl)-1H-pyrazolo [3,4-d]pyrimidine-3-yl)-4-((3R,5S)-3,5-dimethylpiperazine-1-yl)benzamide

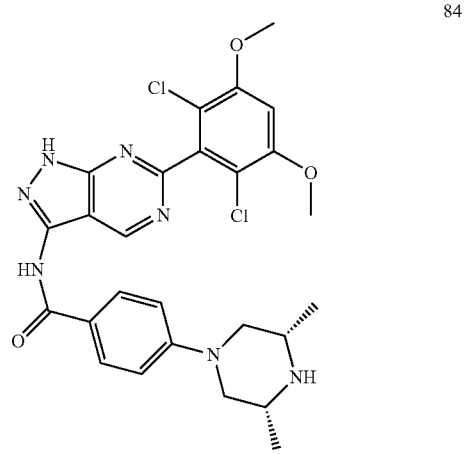 [SMILES: COc1cc(OC)c(Cl)c(-c2ncc3c(NC(=O)c4ccc(N5C[C@@H](C)N[C@@H](C)C5)cc4)n[nH]c3n2)c1Cl]

84

¹H NMR (d-MeOD, 400 MHz) δ ppm 9.76 (s, 1H), 8.05 (d, 2H, J=8.8 Hz), 7.17 (d, 2H, J=8.8 Hz), 6.96 (s, 1H), 3.99 (s, 6H), 3.53-3.49 (m, 2H), 3.42-3.38 (m, 2H), 2.86-2.80 (m, 2H), 1.48 (d, 6H, J=5.2 Hz). LCMS: 556 (M+H)⁺, RT=1.33 min.

The following compounds can be obtained by the synthetis method of compound 63:

N-(6-(2,6-dichloro-3,5-dimethoxyphenyl)-1H-pyrazolo [3,4-b]pyridin-3-yl)-6-(4-methylpiperazine-1-yl)nicotinamide

85

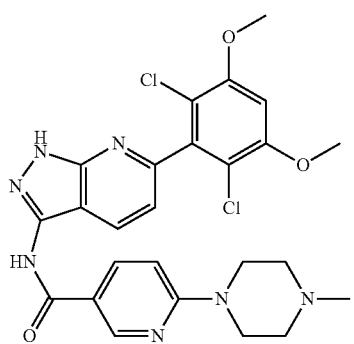

¹H NMR (DMSO-d6, 400 MHz) δ ppm 8.84 (s, 1H), 8.37 (d, 1H, J=8.4 Hz), 8.20 (d, 1H, J=7.6 Hz), 7.03 (s, 2H), 6.92 (d, 1H, J=8.8 Hz), 3.98 (s, 6H), 3.63 (s, 4H), 2.41 (t, 4H, J=4.0 Hz), 2.22 (s, 3H). LCMS: 542.2 [M+H]⁺, RT=1.18 min.

N-(6-(2,6-dichloro-3,5-dimethoxyphenyl)-1H-pyrazolo [3,4-b]pyridin-3-yl)-6-(4-ethylpiperazine-1-yl)nicotinamide

86

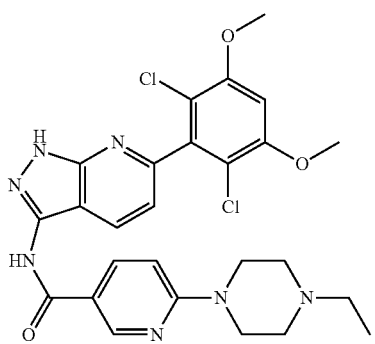

1H NMR (DMSO-d6, 400 MHz) δ ppm 13.40 (s, 1H), 10.91 (s, 1H), 8.84 (d, 1H, J=2.4 Hz), 8.41 (d, 1H, J=8.4 Hz), 8.19 (dd, 1H, J₁=J₂=2.4 Hz), 7.09 (t, 2H, J=12.4 Hz), 6.93 (d, 1H, J=9.2 Hz) 3.98 (s, 6H), 3.65 (t, 4H, J=3.6 Hz), 2.45 (t, 4H, J=4.8 Hz), 2.39 (q, 2H, J=7.2 Hz), 1.05 (t, 3H, J=6.8 Hz), LCMS: 556.2 [M+H]⁺, RT=1.19 min.

N-(6-(2,6-dichloro-3,5-dimethoxyphenyl)-1H-pyrazolo [3,4-b]pyridin-3-yl)-6-(3,3-dimethylpiperazine-1-yl)nicotinamide

87

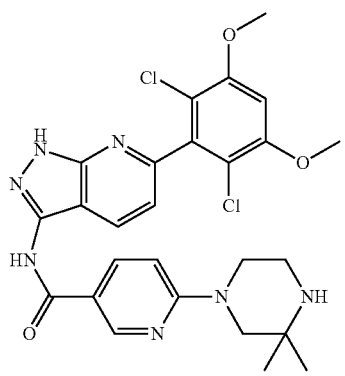

1H NMR (DMSO-d6, 400 MHz) δ ppm 13.39 (s, 1H), 10.86 (s, 1H), 8.81 (d, 1H, J=2.0 Hz), 8.40 (d, 1H, J=8.0 Hz), 8.16 (dd, 1H, J1=2.4 Hz, J2=2.4 Hz), 7.08 (t, 2H, J=8.4 Hz), 6.90 (d, 1H, J=9.2 Hz), 3.99 (s, 6H), 3.60 (t, 2H, J=4.0 Hz), 3.43 (s, 2H), 2.82 (t, 2H, J=4.4 Hz), 1.04 (s, 6H). LCMS: 556.2 [M+H]+, RT=1.21 min.

6-(4-cyclopropylpiperazine-1-yl)-N-(6-(2,6-dichloro-3,5-dimethoxyphenyl)-1H-pyrazolo [3,4-b]pyridin-3-yl)nicotinamide

88

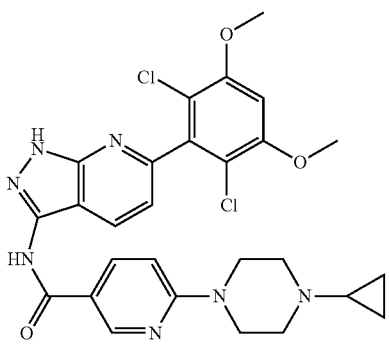

1H NMR (DMSO-d6, 400 MHz) δ ppm 13.40 (s, 1H), 10.92 (s, 1H), 8.85 (d, 1H, J=1.6 Hz), 8.41 (d, 1H, J=8.4 Hz), 8.20 (dd, 1H, J1=2.0 Hz, J2=1.6 Hz), 7.08 (t, 2H, J=8.0 Hz), 6.94 (d, 1H, J=9.2 Hz), 3.98 (s, 6H), 3.62 (s, 4H), 2.62 (s, 4H), 10.66 (d, 1H, J=3.6 Hz), 0.46 (d, 2H, J=4.4 Hz), 0.38 (d, 2H, J=2.4 Hz). LCMS: 568.2 [M+H]⁺, RT=1.21 min.

101

N-(6-(2,6-dichloro-3,5-dimethoxyphenyl)-1H-pyrazolo [3,4-b]pyridin-3-yl)-4-(4-cyclopropylpiperidine-1-yl)benzamide

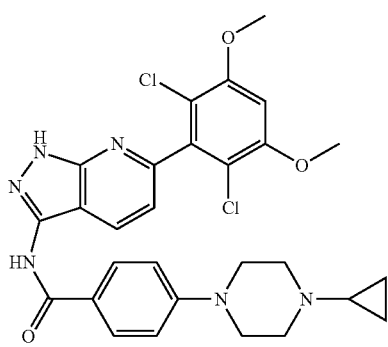

1H NMR (d6-DMSO, 400 MHz) δ ppm 8.34 (d, 1H, J=8 Hz), 8.00 (d, 2H, J=8.8 Hz), 7.02 (t, 4H, J=7.8 Hz), 3.98 (s, 6H), 3.26 (s, 4H), 2.67 (s, 4H), 10.66 (s, 1H), 0.45 (d, 2H, J=4.81 Hz), 0.363 (s, 2H). LCMS: 567 (M+H)+, RT=1.22 min.

102

N-(6-(2,6-dichloro-3,5-dimethoxyphenyl)-1H-pyrazolo [3,4-b] pyridin-3-yl)-4-(3,3-dimethylpiperazine-1-yl)-3-fluorobenzamide

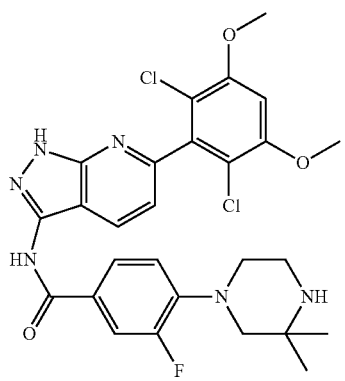

1H NMR (400 MHz, DMSO-d6): 13.48 (s, 1H), 11.10 (s, 1H), 8.86 (brs, 1H), 8.39 (d, 1H, J=8.0 Hz), 7.96-7.92 (m, 2H), 7.25 (t, 1H, J=8.8 Hz), 7.10 (d, 1H, J=2.8 Hz), 7.05 (s, 1H), 3.99 (s, 6H), 3.35 (s, 4H), 3.18 (s, 2H), 1.41 (s, 6H).

N-(6-(2,6-dichloro-3,5-dimethoxyphenyl)-1H-pyrazolo [3,4-b] pyridin-3-yl)-4-((3S, 5R)-3,4,5-trimethylpiperidine-1-yl)benzamide

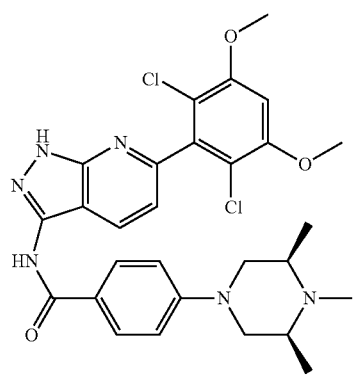

1H NMR (400 MHz, DMSO-d6): 13.41 (s, 1H), 10.90 (s, 1H), 9.38 (s, 1H), 8.39 (d, 1H, J=8.0 Hz), 8.06 (d, 2H, J=8.8 Hz), 7.16 (d, 2H, J=9.2 Hz), 7.09 (d, 1H, J=12.4 Hz), 7.05 (s, 1H), 4.19 (d, 2H, J=13.6 Hz), 3.99 (s, 6H), 3.35-3.44 (m, 2H), 2.90-2.95 (m, 2H), 2.88 (d, 3H, J=4.4 Hz), 1.39 (d, 6H, J=6.4 Hz).

N-(6-(2,6-dichloro-3,5-dimethoxyphenyl)-1H-pyrazolo [3,4-b] pyridin-3-yl)-2-(4-methylpiperazine-1-yl)pyrimidine-5-formamide

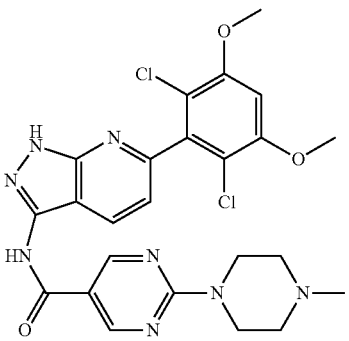

1H NMR (400 MHz, DMSO-d6): 13.46 (s, 1H), 11.08 (s, 1H), 9.00 (s, 2H), 8.42 (d, 1H, J=8.4 Hz), 8.33 (s, 1H), 7.09 (d, 1H, J=8.4 Hz), 7.05 (s, 1H), 3.99 (s, 6H), 3.85-3.88 (m, 4H), 2.38-2.40 (m, 4H), 2.23 (s, 3H).

The following compounds were obtained by similar synthetis method of compound 44:

103

N-(6-(2,6-difluoro-3,5-dimethoxyphenyl)-1H-indazole-3-yl)-4-(piperidine-1-yl)benzamide

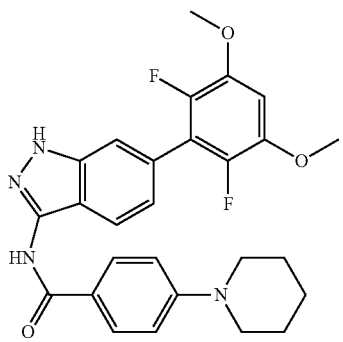

1H NMR (400 MHz, DMSO-d6): 12.85 (s, 1H), 10.38 (s, 1H), 7.87 (d, 2H, J=8.8 Hz), 7.77 (d, 1H, J=8.4 Hz), 7.50 (s, 1H), 7.08 (t, 2H, J=8.4 Hz), 6.62 (d, 2H, J=8.8 Hz), 6.34 (d, 1H, J=6.4 Hz), 3.92 (s, 6H), 3.77-3.82 (m, 1H), 1.91-2.00 (m, 2H), 1.65-1.73 (m, 2H), 1.55-1.62 (m, 2H), 1.45-1.51 (m, 2H).

104

N-(6-(2,6-difluoro-3,5-dimethoxyphenyl)-1H-indazole-3-yl)-4-(4-methyl-1,4-diazepane-1-yl)benzamide

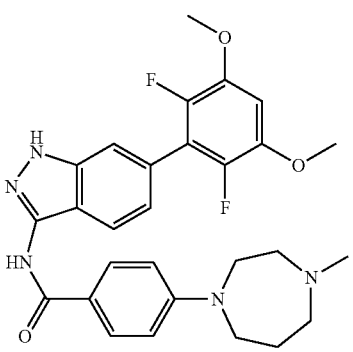

1H NMR (400 MHz, DMSO-d6): 13.91 (s, 1H), 10.56 (s, 1H), 9.81 (s, 1H), 8.02 (d, 2H, J=8.4 Hz), 7.78 (d, 1H, J=8.4 Hz), 7.52 (s, 1H), 7.06-7.09 (m, 2H), 6.89 (d, 2H, J=8.8 Hz), 3.92 (s, 6H), 3.85-3.96 (m, 2H), 3.67-3.74 (m, 1H), 3.45-3.58 (m, 3H), 3.12-3.26 (m, 1H), 2.86 (d, 3H, J=3.6 Hz), 2.15-2.25 (m, 2H).

N-(6-(2,6-difluoro-3,5-dimethoxyphenyl)-1H-indazole-3-yl)-4-((4-methylpiperazine-1-yl)methyl)benzamide

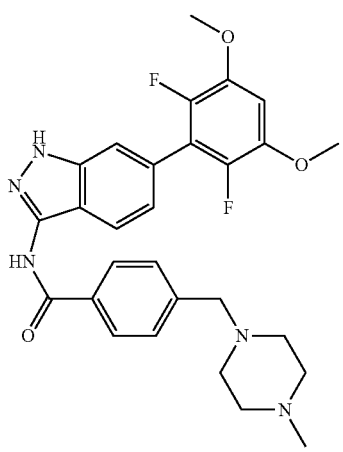

1H NMR (400 MHz, DMSO-d6): 13.01 (s, 1H), 10.91 (s, 1H), 8.10 (s, 2H), 7.79 (s, 1H), 7.54 (s, 3H), 7.08 (s, 2H), 3.91 (s, 6H), 3.83 (s, 2H), 3.36-3.48 (m, 2H), 2.95-3.14 (m, 4H), 2.79 (s, 3H), 2.50-2.58 (m, 2H).

N-(6-(2,6-difluoro-3,5-dimethoxyphenyl)-1H-indazole-3-yl)-2-(4-methylpiperazine-1-yl) pyrimidine-5-formamide

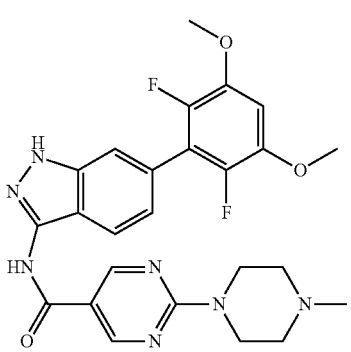

1H NMR (400 MHz, DMSO-d6): 12.99 (s, 1H), 10.95 (s, 1H), 9.08 (s, 2H), 7.84 (d, 1H, J=8.4 Hz), 7.54 (s, 1H), 7.06-7.11 (m, 2H), 4.75-4.95 (m, 2H), 3.92 (s, 6H), 3.35-3.55 (m, 2H), 3.05-3.35 (m, 4H), 2.84 (s, 3H).

N-(6-(2,6-difluoro-3,5-dimethoxyphenyl)-1H-indazole-3-yl)-4-(3,3-dimethylpiperazine-1-yl)-3-methoxybenzamide

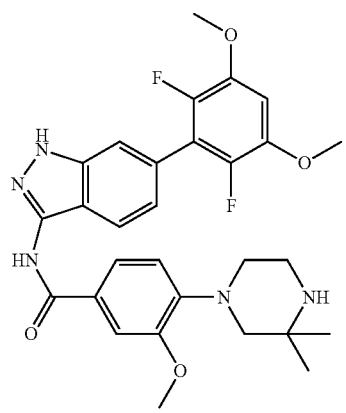

97

1H NMR (400 MHz, MeOD): 7.86 (d, 1H, J=8.4 Hz), 7.69-7.72 (m, 2H), 7.54 (s, 1H), 7.18 (d, 1H, J=8.4 Hz), 7.09 (d, 1H, J=8.0 Hz), 6.94 (t, 1H, J=8.0 Hz), 3.98 (s, 3H), 3.93 (s, 6H), 3.42-3.45 (m, 2H), 3.35-3.39 (m, 2H), 3.19 (s, 2H), 1.54 (s, 6H).

N-(6-(2,6-difluoro-3,5-dimethoxyphenyl)-1H-indazole-3-yl)-4-(3-(dimethylamino)pyrrolidine-1-yl)benzamide

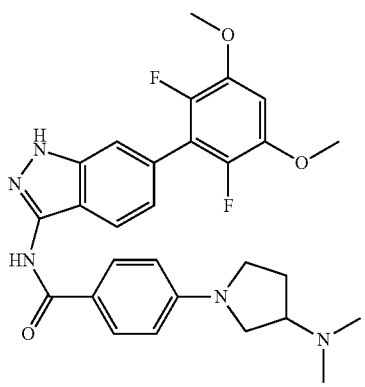

98

1H NMR (400 MHz, DMSO-d6): 12.88 (s, 1H), 10.51 (s, 1H), 8.00-8.01 (m, 2H), 7.78-7.80 (m, 1H), 7.51 (s, 1H), 7.08 (s, 2H), 6.65-6.67 (m, 2H), 3.92 (s, 6H), 3.62-3.71 (m, 1H), 3.51-3.60 (m, 1H), 2.50 (s, 6H), 2.26-2.35 (m, 2H), 1.97-2.15 (m, 1H).

The following compounds can be obtained by the synthesis method of compound 63:

N-(6-(2,6-dichloro-3,5-dimethoxyphenyl)-1H-pyrazolo [3,4-b] pyridin-3-yl)-4-(3,3,5,5-tetramethylpiperidine-1-yl)benzamide

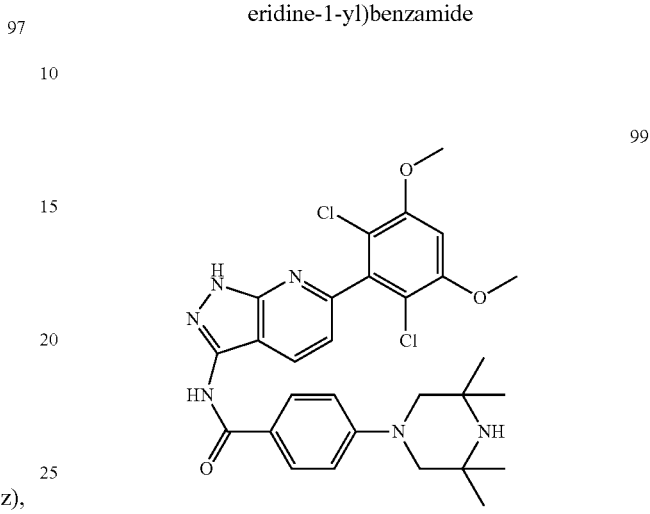

99

1H NMR (400 MHz, MeOD): 8.51 (d, 1H, J=8.4 Hz), 8.03 (d, 1H, J=7.6 Hz), 7.12-7.22 (m, 3H), 6.95 (s, 1H), 3.99 (s, 6H), 3.47 (s, 4H), 1.52 (s, 12H).

N-(6-(2,6-dichloro-3,5-dimethoxyphenyl)-1H-pyrazolo [3,4-b]pyridin-3-yl)yl)-4-(3-(dimethylamino)pyrrolidine-1-yl)benzamide

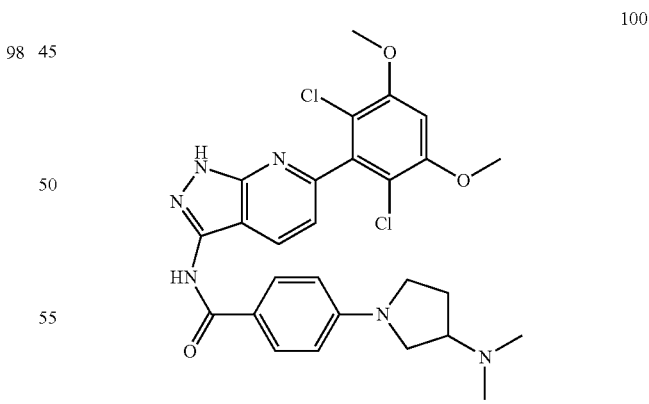

100

1H NMR (400 MHz, MeOD): 8.27 (d, 1H, J=8.4 Hz), 8.01 (d, 2H, J=8.4 Hz), 7.12 (d, 1H, J=8.4 Hz), 6.94 (s, 1H), 6.79 (d, 2H, J=8.4 Hz), 4.06-4.13 (m, 1H), 3.99 (s, 6H), 3.85-3.93 (m, 1H), 3.70-3.75 (m, 1H), 3.61-3.65 (m, 1H), 3.46-3.52 (m, 1H), 3.01 (s, 6H), 2.60-2.67 (m, 1H), 2.26-2.36 (m, 1H).

N-(6-(2,6-dichloro-3,5-dimethoxyphenyl)-1H-pyrazolo [3,4-b] pyridin-3-yl)-4-(3,3-dimethylpiperazine-1-yl)-3-methoxybenzamide

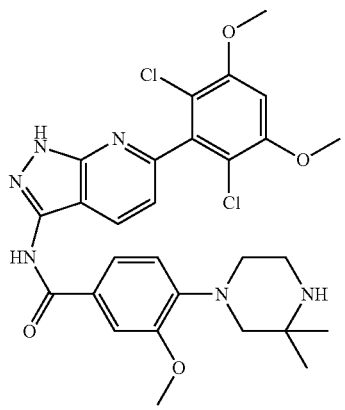

1H NMR (400 MHz. DMSO-d6): 13.46 (s, 1H), 11.07 (s, 1H), 8.41 (d, 1H, J=8.4 Hz), 7.23-7.50 (m, 2H), 7.06-7.11 (m, 3H), 3.99 (s, 6H), 3.92 (s, 3H), 3.29 (s, 2H), 3.25 (s, 2H), 3.07 (s, 2H), 2.58 (s, 1H), 1.41 (s, 6H).

Example 2

Effect of the Compounds on FGFR1, FGFR2, FGFR3, KDR Kinase Activity at the Molecular Level 1. Experimental Method The enzyme reaction substrate Poly(Glu,Tyr) 4:1 was diluted with PBS without potassium ion (10 mM sodium phosphate buffer, 150 mM NaCl, pH7.2-7.4) to 20 µg/mL, 125 µL/well to coat the enzyme plate, and reacted at 37° C. for 12-16 hours. After the liquid was removed from the wells, the plate was washed three times with 200 µL/well of T-PBS (PBS containing 0.1% Tween-20) for 5 minutes each. The enzyme plate was dried in a 37° C. oven for 1-2 hours. 50 µL of the ATP solution diluted with the reaction buffer (50 mM HEPES pH 7.4, 50 mM MgCl$_2$, 0.5 mM MnCl$_2$, 0.2 mM Na$_3$VO$_4$, 1 mM DTT) was added into each well at a 5 µM final concentration. The compounds were diluted to the appropriate concentration in DMSO, 1 µL/well or containing the corresponding concentrations of DMSO (negative control wells). The reaction was initiated by addition of each kinase domain recombinant protein diluted with 49 µL of reaction buffer. Two control wells without ATP were set in each experiment. The reaction mixtures were placed on a shaker (100 rpm) to react at 37° C. for 1 hour. The plates were washed with T-PBS for three times. 100 µL/well of the primary antibody PY99 dilution was added, and reacted on a shaker (100 rpm) at 37° C. for 0.5 hour. The plates were washed with T-PBS for three times. 100 µL/well of the secondary anti-horseradish peroxidase-labeled goat anti-mouse IgG dilution was added, and reacted on a shaker at 37° C. for 0.5 hour. The plates were washed with T-PBS for three times. 100 µL/well of 2 mg/mL OPD developing solution (diluted with 0.1M citric acid-sodium citrate buffer containing 0.03% H$_2$O$_2$ (pH=5.4)), and reacted in dark for 1-10 minutes at 25° C. (Ultrasound is needed in OPD dissolution, and the developing solution should be prepared on the site). The reaction was quenched with 50 µL/well of 2M H$_2$SO$_4$, and read out at 490 nm using a tunable microplate microplate reader SPECTRA MAX 190.

The inhibition ratio of the samples was determined by the following formula:

$$\text{inhibition rate (\%)} = \left(1 - \frac{OD \text{ of the compound}}{OD \text{ of the negative control}} - OD \text{ of the control well (without } ATP)\right) \times 100\%$$

The IC$_{50}$ values were obtained by four-parameter regression analysis using the software accompanying the microplate reader.

2. Results

Some of the IC$_{50}$ values are listed in the following table. The symbol + represents an IC$_{50}$ of less than 100 nm, the symbol ++ represents an IC$_{50}$ of 100 nm to 500 nm, and N/A represents no data.

| Example No. | FGFR1 IC$_{50}$(nm) | FGFR2 IC$_{50}$(nm) | FGFR3 IC$_{50}$(nm) |
| --- | --- | --- | --- |
| 14 | + | + | + |
| 15 | + | + | + |
| 16 | + | + | + |
| 17 | + | + | + |
| 18 | + | + | + |
| 19 | + | + | + |
| 20 | + | + | N/A |
| 21 | + | + | N/A |
| 22 | + | + | N/A |
| 23 | + | + | N/A |
| 24 | + | + | N/A |
| 25 | + | + | N/A |
| 26 | + | + | N/A |
| 27 | + | + | N/A |
| 28 | + | + | N/A |
| 29 | + | + | N/A |
| 30 | + | + | N/A |
| 31 | + | + | N/A |
| 32 | + | + | N/A |
| 33 | + | + | N/A |
| 34 | + | + | N/A |
| 35 | + | + | N/A |
| 36 | + | + | N/A |
| 37 | + | + | N/A |
| 44 | + | + | N/A |
| 45 | + | + | N/A |
| 46 | + | + | N/A |
| 47 | + | + | N/A |
| 48 | + | + | N/A |
| 55 | + | + | N/A |
| 63 | + | + | + |
| 64 | + | + | N/A |
| 65 | + | + | N/A |
| 66 | + | + | N/A |
| 67 | + | + | N/A |
| 68 | + | + | N/A |
| 69 | + | + | N/A |
| 70 | + | + | N/A |
| 71 | + | + | N/A |
| 72 | + | + | N/A |
| 73 | + | + | N/A |
| 83 | + | + | N/A |
| 85 | + | + | N/A |
| 86 | + | + | N/A |
| 87 | + | + | N/A |
| 88 | + | + | N/A |
| 89 | + | + | N/A |
| 90 | + | + | N/A |
| 91 | + | + | N/A |
| 92 | + | + | N/A |
| 93 | + | + | N/A |

| Example No. | FGFR1 IC$_{50}$(nm) | FGFR2 IC$_{50}$(nm) | FGFR3 IC$_{50}$(nm) |
|---|---|---|---|
| 94 | + | + | N/A |
| 95 | + | + | N/A |
| 96 | + | + | N/A |
| 97 | + | + | N/A |
| 98 | + | + | N/A |
| 99 | + | + | N/A |
| 100 | + | + | N/A |
| 101 | + | + | N/A |

The results have shown that the compounds of the invention can effectively inhibit the activity of the various kinds of FGFR kinase at an extremely low concentration (≤100 nm).

Example 3

Effect of the Compounds on FGFR1-Mediated Proliferation Ability of Tumor Cells

1. Experimental Method

The growth inhibition of the acute myelogenous leukemia cell strain KG1 (FGFR1-dependent tumor cell strain; the FGFR1 fusion protein in the cell was expressed in the cytoplasm; purchased from ATCC cell bank) by the compounds was detected with CCK-8 cell count kit (Dojindo). The specific steps are as follows: KG1 cells in logarithmic growth phase were seeded onto a 96-well culture plate in appropriate density, 90 ul per well. After overnight culture, different concentrations of compounds were added and the treatment continued for 72 h, and solvent control group (negative control) was set. After treatment for 72 h, the effect of the compounds on cell proliferation was observed by CCK-8 cell counting kit (Dojindo). 10 µL of CCK-8 reagent was added to each well. After incubated for 2-4 hours in a 37 □ incubator, read with SpectraMax 190 microplate reader at 450 nm wavelength. The inhibition rate (%) of the compounds on tumor cell growth was calculated using the following formula: Inhibition rate (%)=(OD negative control well−OD administered well)/OD negative control well× 100%. The IC$_{50}$ values were obtained by four-parameter regression analysis using the software accompanying the microplate reader.

2. Results

The IC$_{50}$ values of some compounds are listed in the following table. The symbol + represents an IC$_{50}$ of less than 200 nm, and the symbol ++ represents an IC$_{50}$ of 200 nm to 1000 nm.

| Example No. | KG1 IC$_{50}$(nm) |
|---|---|
| 14 | + |
| 15 | + |
| 16 | ++ |
| 17 | ++ |
| 18 | + |
| 19 | ++ |

The results have shown that the compounds of the present invention can effectively inhibit the proliferation of tumor cells at extremely low concentrations (≤1000 nm, preferably ≤200 nm).

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of formula (I), or a pharmaceutically acceptable salt thereof,

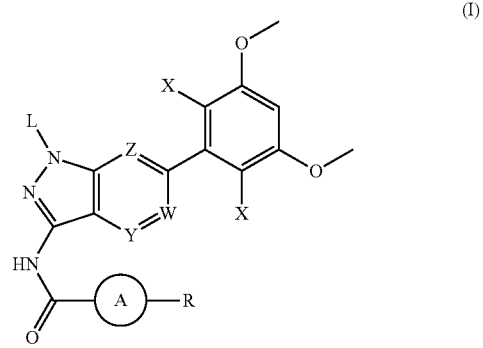

(I)

wherein:

L is selected from the group consisting of H and tetrahydropyranyl (THP);

each X is independently selected from the group consisting of Cl, F, H, and CN;

W, Y, Z are each independently selected from the group consisting of N and CH;

ring A is unsubstituted or substituted 5- to 8-membered arylene group, or a unsubstituted or substituted 5- to 8-membered heteroarylene group, wherein the heteroarylene group contains at least one heteroatom selected from the group consisting of nitrogen, oxygen, and sulfur; unsubstituted or substituted 3- to 12-membered saturated heterocyclic ring or carbocyclic ring, wherein the heterocyclic ring contains at least one heteroatom selected from the group consisting of nitrogen, oxygen, and sulfur; or

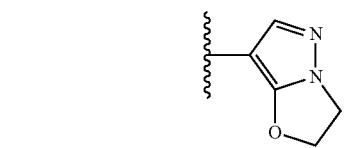 [SMILES: *c1cnn2c1OCC2]

R is H, or a substituted or unsubstituted group selected from the group consisting of

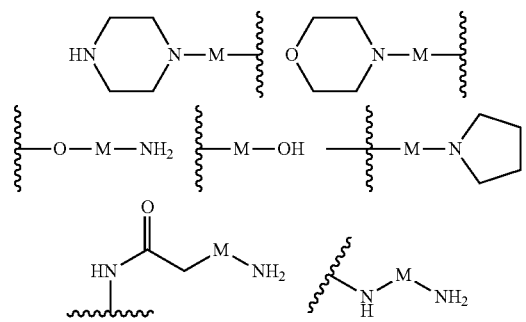

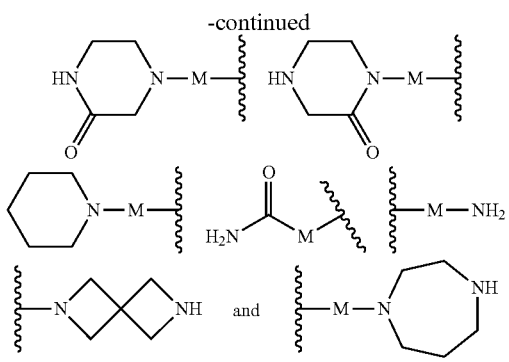

wherein M is absent or selected from the group consisting of substituted or unsubstituted C1-C6 alkylene, substituted or unsubstituted C6-C10 arylene, and substituted or unsubstituted C1-C10 heteroarylene;

wherein substituted means that one or more hydrogen atoms on said group are substituted with a substituent selected from the group consisting of halogen, unsubstituted or halogenated C1-C6 alkyl, unsubstituted or halogenated C1-C6 alkoxy group, unsubstituted or halogenated C2-C6 alkoxyalkyl group, unsubstituted or halogenated C3-C8 cycloalkyl group, unsubstituted or halogenated C2-C6 alkylcarbonyl group, unsubstituted or halogenated C1-C6 alkylene-hydroxy, and unsubstituted or C1-C6 alkyl-substituted amine group.

2. The compound according to claim 1, wherein,
ring A is unsubstituted or substituted 6-membered aryl group, or unsubstituted or substituted 5- to 6-membered heteroaryl group, wherein the heteroaryl group contains at least one heteroatom selected from the group consisting of nitrogen, oxygen, and sulfur; or unsubstituted or substituted 5- to 6-membered saturated heterocyclic ring or carbocyclic ring, wherein the heterocyclic ring contains at least one heteroatom selected from the group consisting of nitrogen, oxygen, and sulfur;
M is absent or unsubstituted or substituted C1-C4 alkylene group;
wherein substituted means that one or more hydrogen atoms on said group are substituted with a substituent selected from the group consisting of halogen, unsubstituted or halogenated C1-C4 alkyl, unsubstituted or halogenated C1-C4 alkoxy group, unsubstituted or halogenated C1-C4 alkoxyalkyl group, unsubstituted or halogenated C3-C8 cycloalkyl group, unsubstituted or halogenated C2-C6 alkylcarbonyl group, unsubstituted or halogenated C1-C4 alkyl-hydroxy, and unsubstituted or C1-C6 alkyl-substituted amine group.

3. The compound according to claim 1, wherein,
L is H;
each X is independently selected from the group consisting of H, Cl, and F;
ring A is phenyl, pyrazolyl, pyridyl, thiazolyl, pyrimidinyl, pyrazinyl, or piperidinyl;
M is selected from the group consisting of unsubstituted or substituted C1-C3 alkylene group, and absent;
wherein substituted means that one or more hydrogen atoms on said group are substituted with a substituent selected from the group consisting of halogen, unsubstituted or halogenated C1-C4 alkyl, unsubstituted or halogenated C1-C4 alkoxy group, unsubstituted or halogenated C2-C4 alkoxyalkyl group, unsubstituted or halogenated C3-C8 cycloalkyl group, unsubstituted or halogenated C2-C6 alkylcarbonyl group, or halogenated C1-C4 alkyl-hydroxy, and unsubstituted or C1-C6 alkyl-substituted amine group.

4. The compound of formula (I) according to claim 1, wherein the compound of formula (I) is selected from the group consisting of the following compounds: 14, 15, 16, 17, 18, 19, 20, 21, 22, 23, 24, 25, 26, 27, 28, 29, 30, 31, 32, 33, 34, 35, 36, 37, 44, 45, 46, 47, 48, 54, 55, 62, 63, 64, 65, 66, 67, 68, 69, 70, 71, 72, 73, 83, 84, 85, 86, 87, 88, 89, 90, 91, 92, 93, 94, 95, 96, 97, 98, 99, 100, 101, and a compound of the formula:

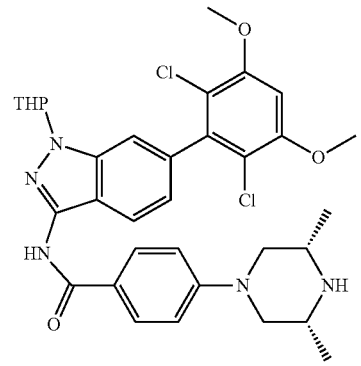

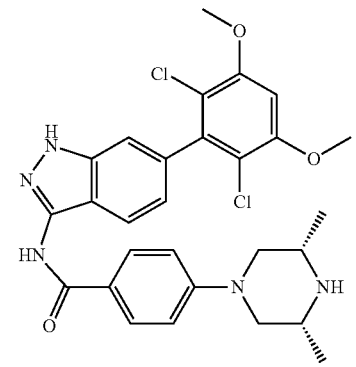

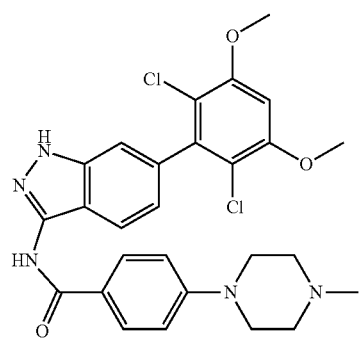

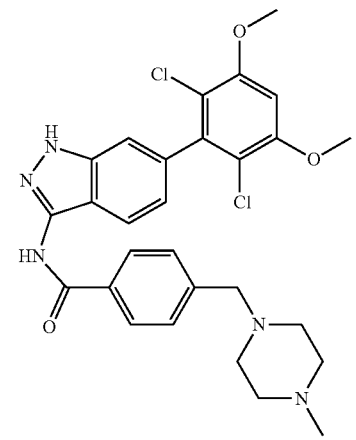

113
-continued
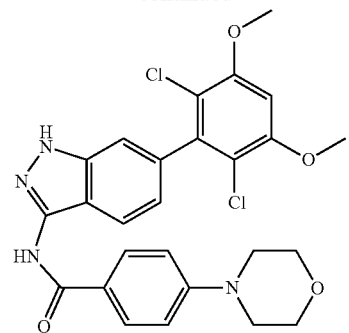
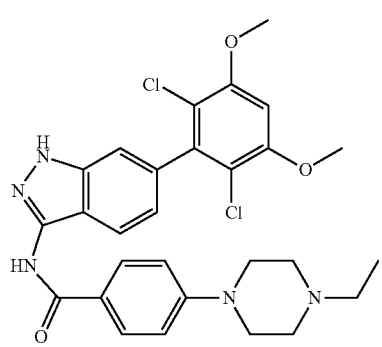
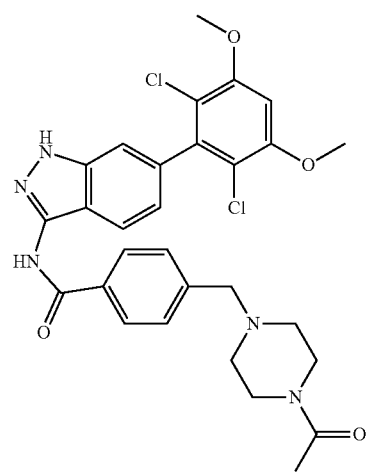
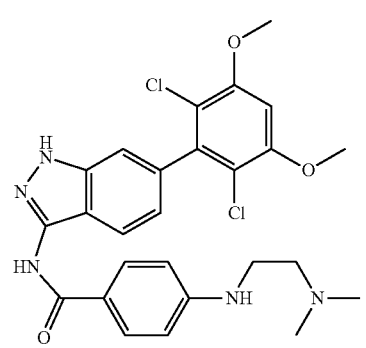
114
-continued
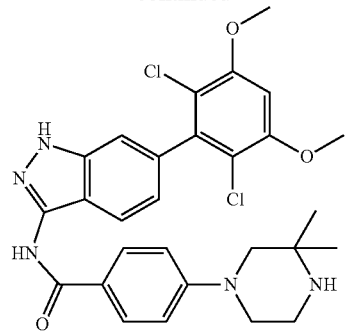
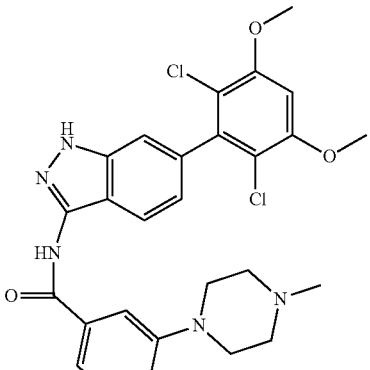
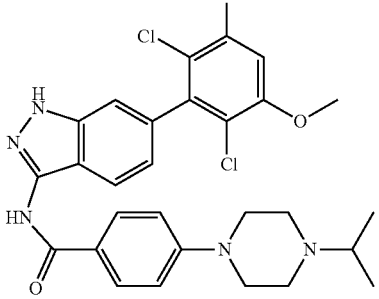
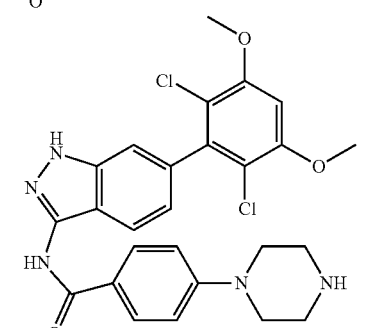
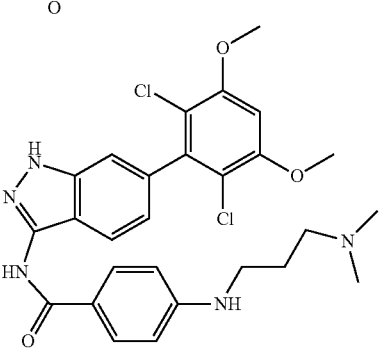

115
-continued
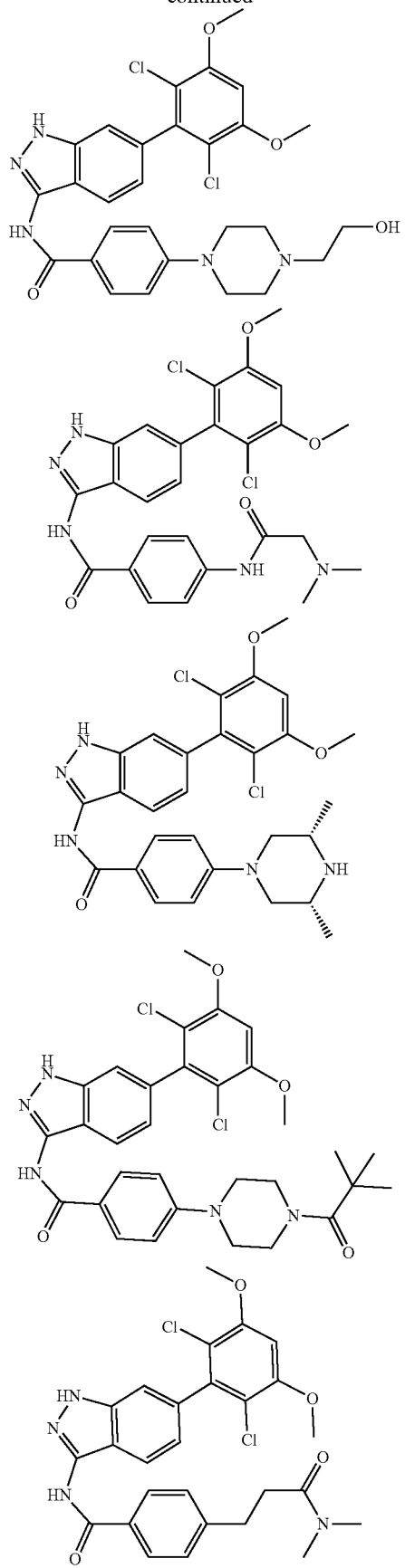
116
-continued
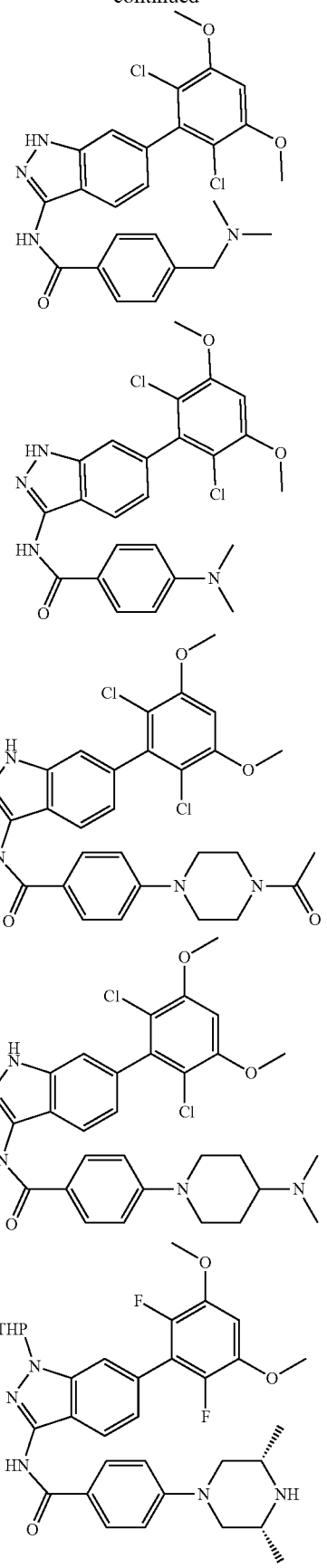

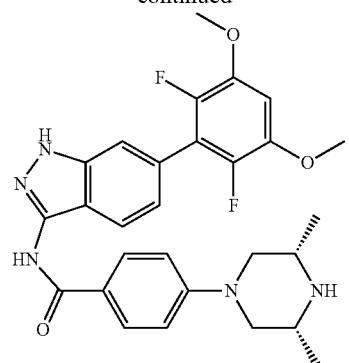
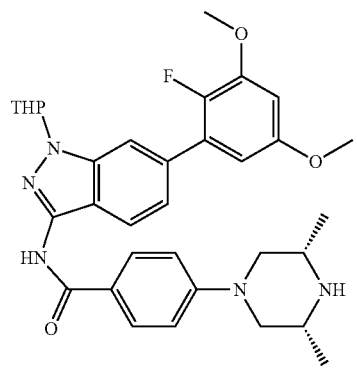
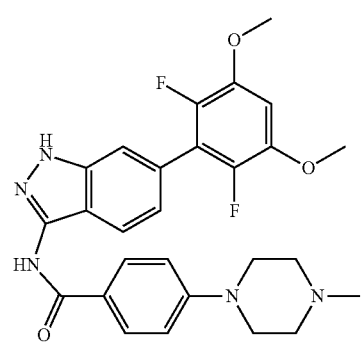
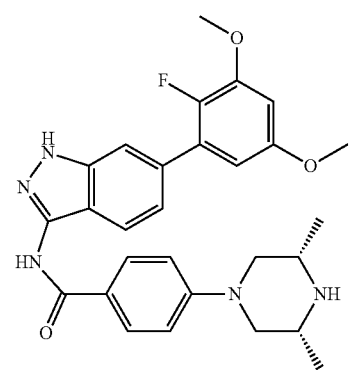
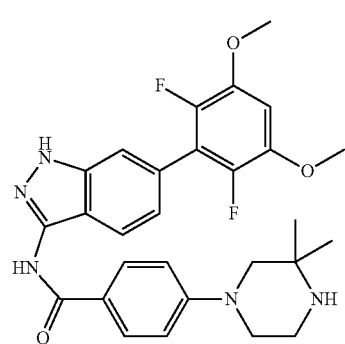
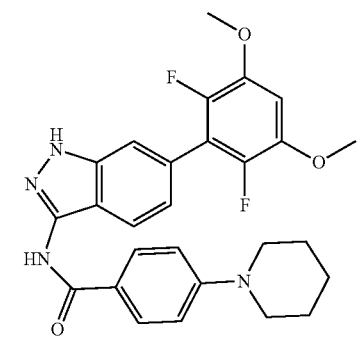
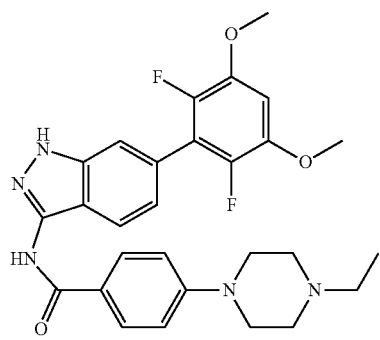
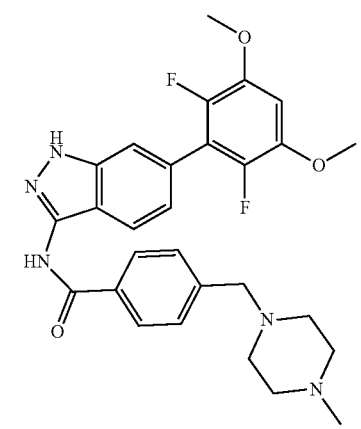

119
-continued
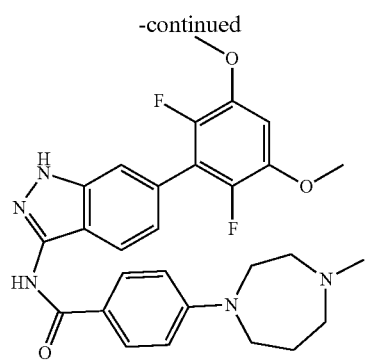
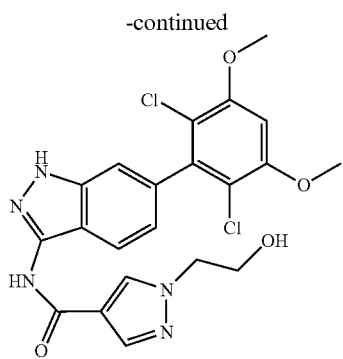
120
-continued
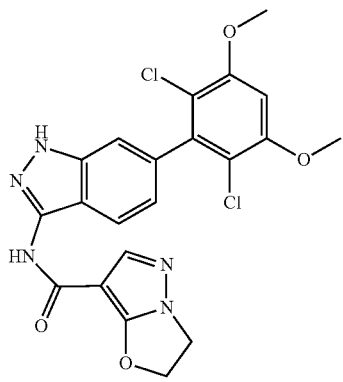
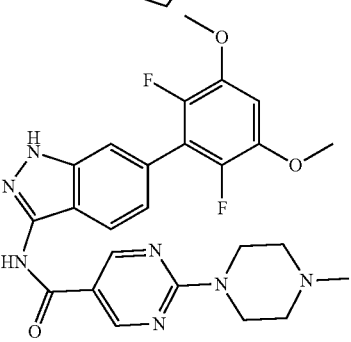
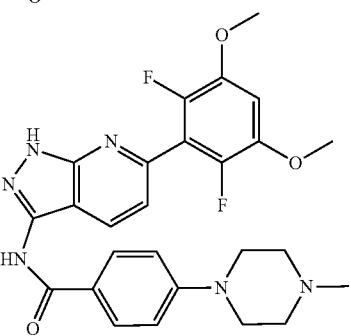
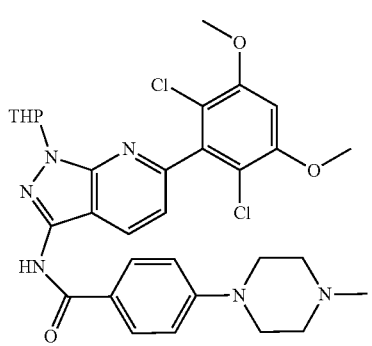

121
-continued
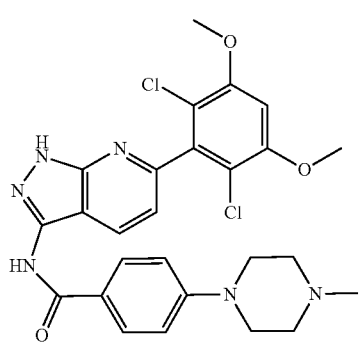
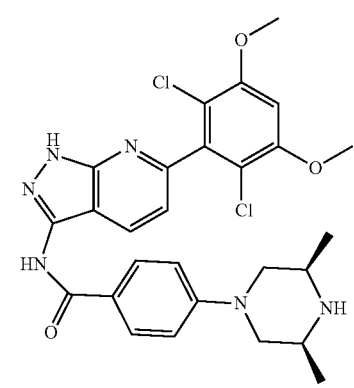
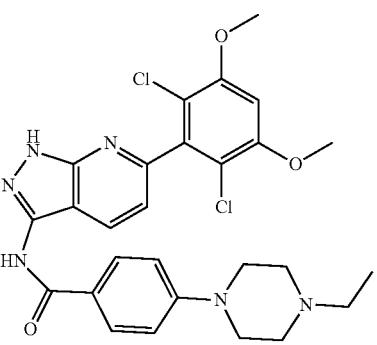
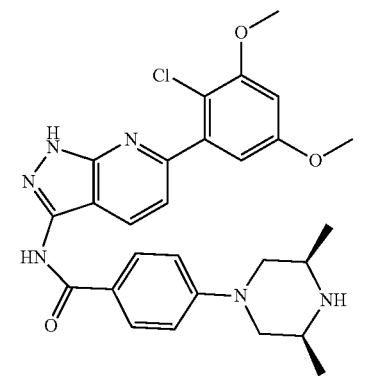
122
-continued
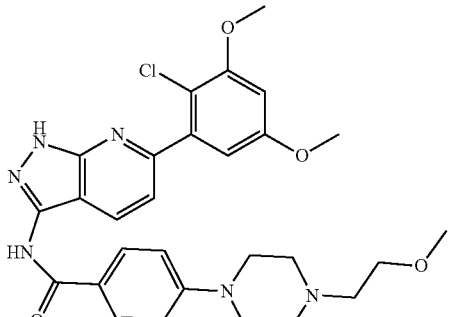
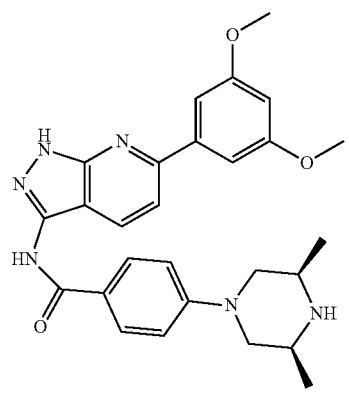
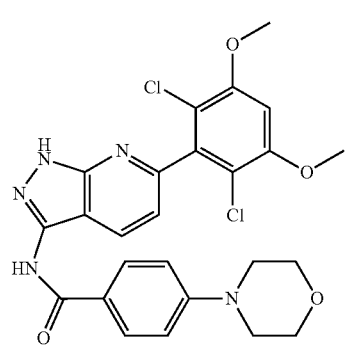
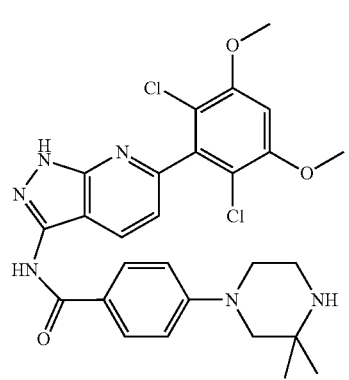

| 123 -continued | 124 -continued |
|---|---|
| 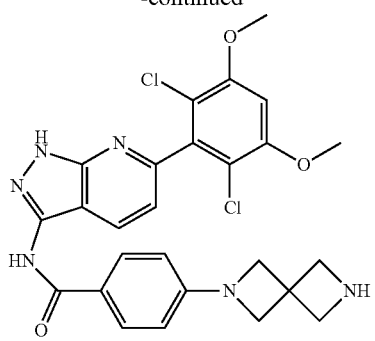 | 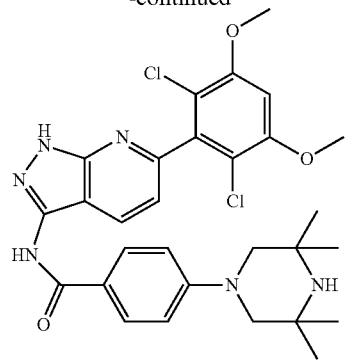 |
| 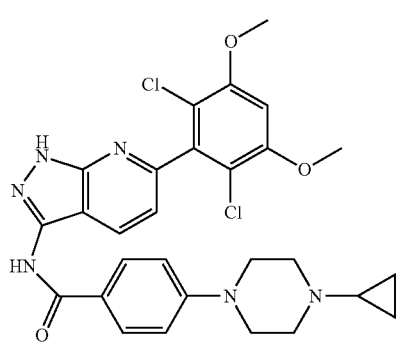 | 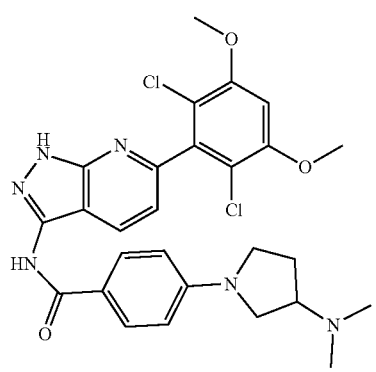 |
| 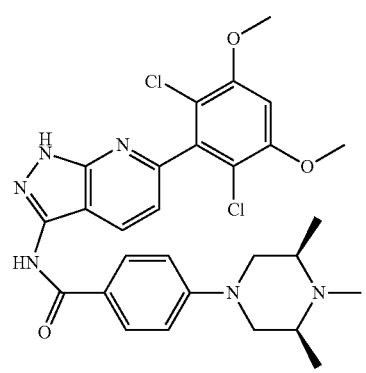 | 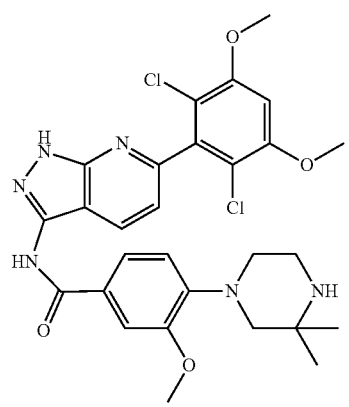 |
| 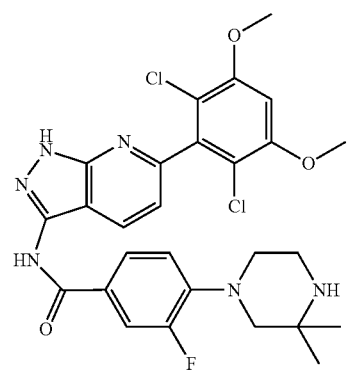 | 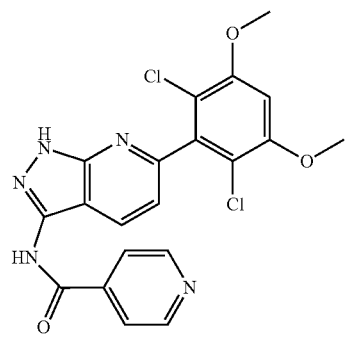 |

125
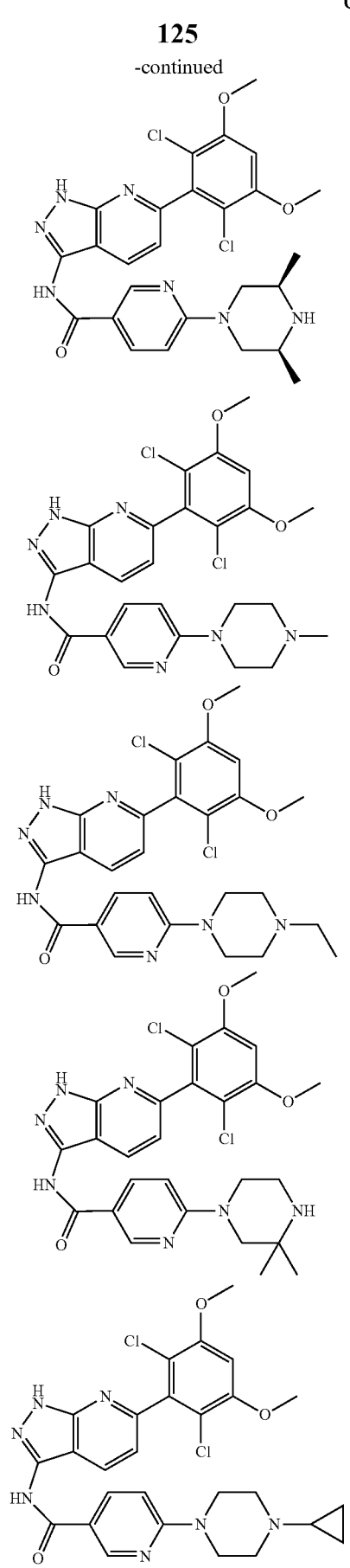
126
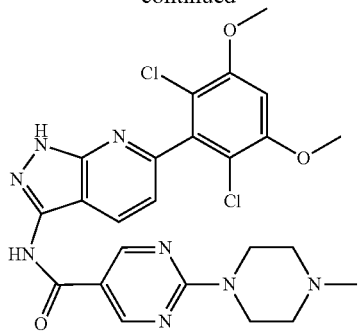
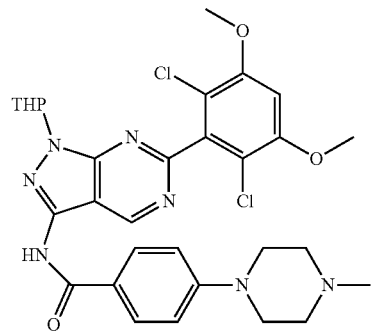
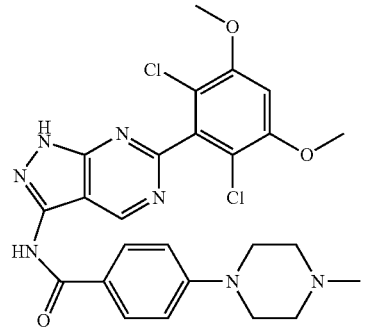

127
-continued
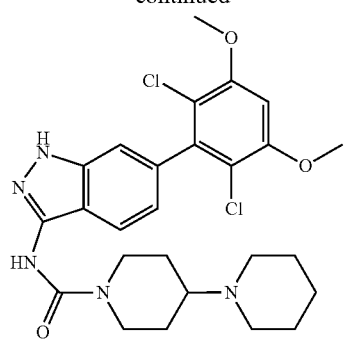
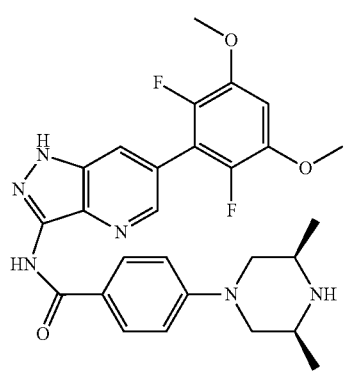
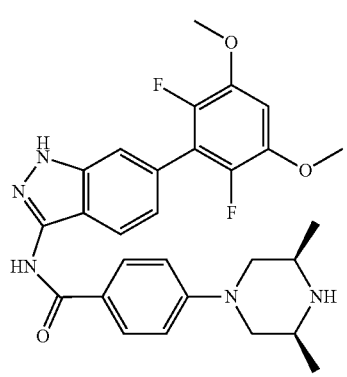
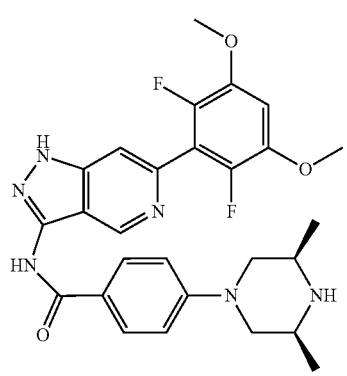
128
-continued
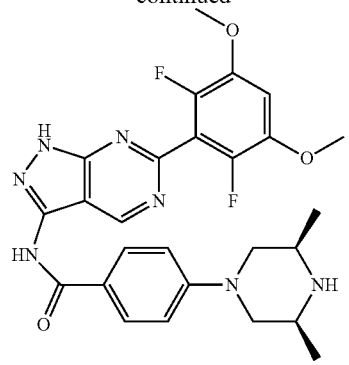
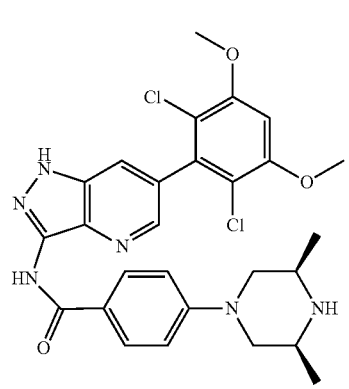
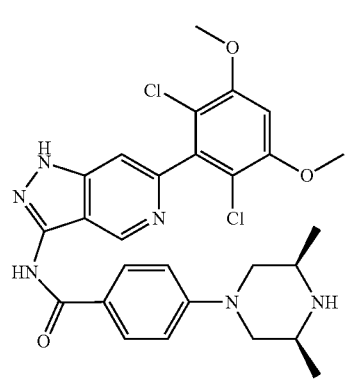
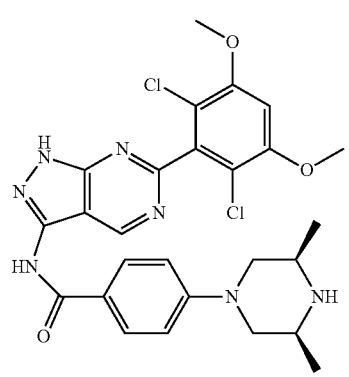

129
-continued
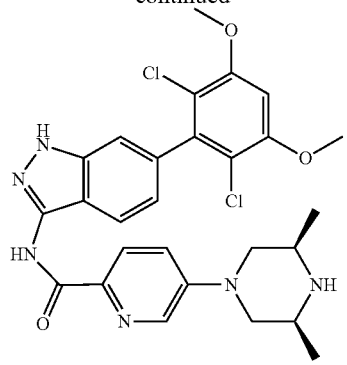
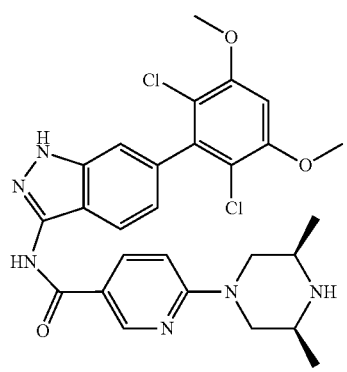
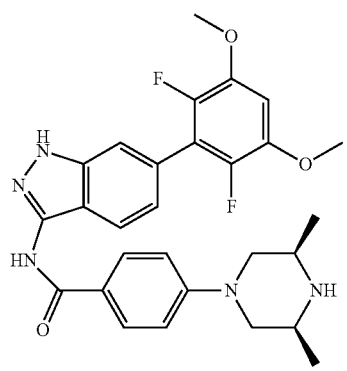
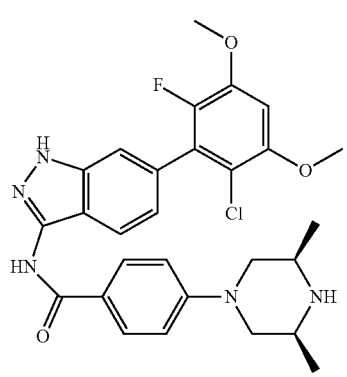
130
-continued
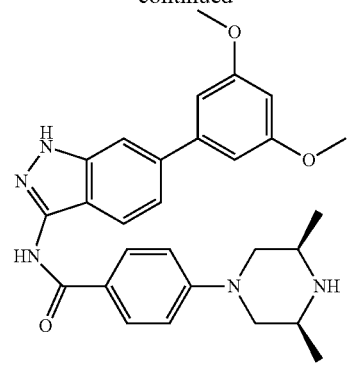
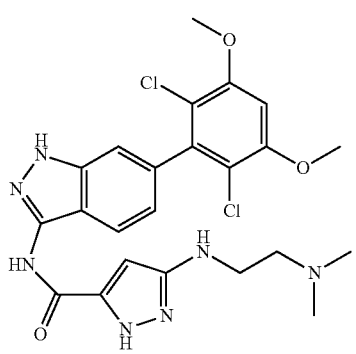
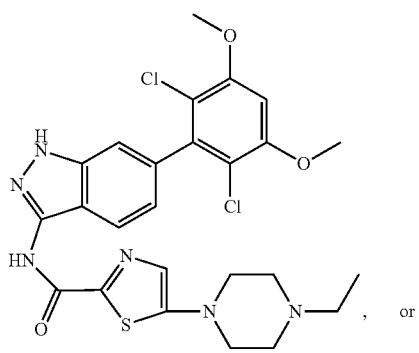, or
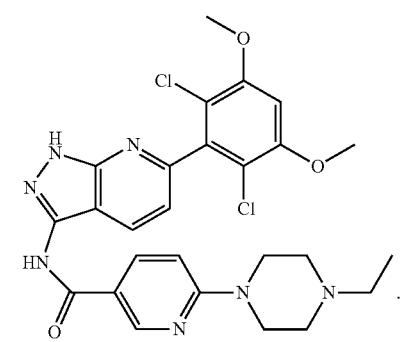.
5. A method for preparing the compound of formula (I) according to claim 1, wherein the method comprises the following step:

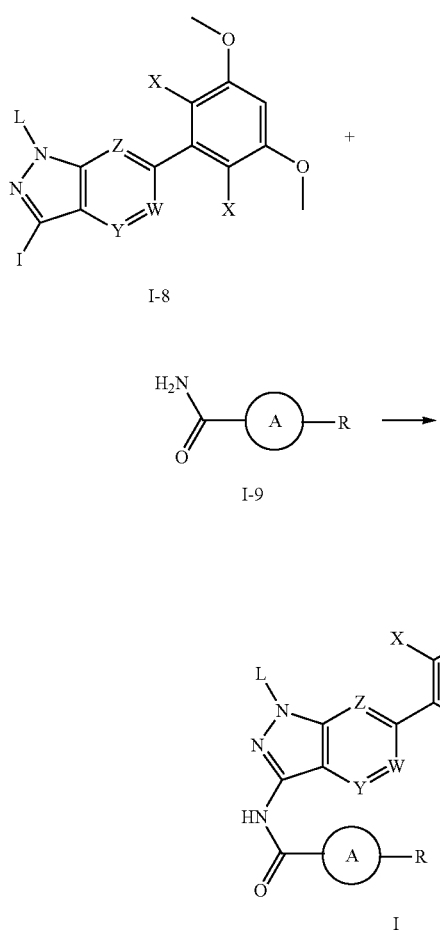

I-8

I-9

I in an inert solvent, reacting the compound of formula I-8 with the compound of formula I-9 to obtain the compound of formula (I);

wherein the groups are defined as in claim 1.

6. The method according to claim 5, wherein the method further comprises the following step:

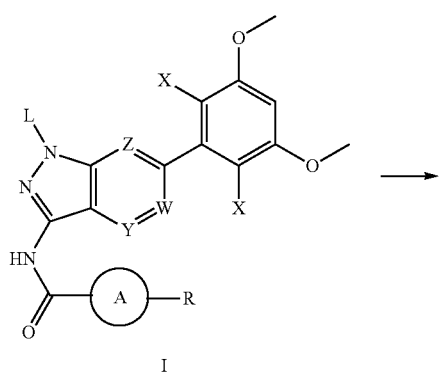

I

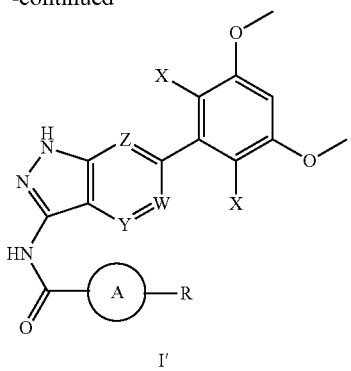

I' deprotecting the compound of formula I in an inert solvent to give the compound of formula I';
wherein L is tetrahydropyranyl (THP).

7. A pharmaceutical composition, wherein the pharmaceutical composition comprises: (i) an effective amount of the compound of formula (I), or a pharmaceutically acceptable salt thereof, and (ii) a pharmaceutically acceptable carrier.

8. A method for inhibiting FGFR kinase activity, wherein the method comprises the following step: administering an inhibitory effective amount of the compound of formula (I) or the pharmaceutically acceptable salt thereof according to claim 1 to a subject in need of inhibition.

9. The method according to claim 8, wherein the FGFR kinase is selected from the group consisting of FGFR1, FGFR2, and FGFR3, or a combination thereof.

10. A method for the treatment of disease associated with FGFR kinase activity or expression amount, wherein the method comprises the following step: administering an effective amount of a compound of claim 1 to a subject in need.

11. A method for the treatment of a cancer selected from the group consisting of endometrial cancer, breast cancer, stomach cancer, bladder cancer, myeloma, liver cancer, and leukemia, wherein the method comprises administering an effective amount of a compound of claim 1 to a subject in need.

12. A method for inhibiting FGFR kinase activity, wherein the method comprises administering an inhibitory effective amount of the pharmaceutical composition according to claim 7 to a subject in need thereof.

13. The method of claim 12, wherein the FGFR kinase is selected from the group consisting of FGFR1, FGFR2, and FGFR3, or a combination thereof.

14. A method for the treatment of disease associated with FGFR kinase activity or expression amount, wherein the method comprises administering an effective amount of the pharmaceutical composition according to claim 7 to a subject in need thereof.

15. A method for the treatment of a cancer selected from the group consisting of endometrial cancer, breast cancer, stomach cancer, bladder cancer, myeloma, liver cancer, and leukemia, wherein the method comprises administering an effective amount of the pharmaceutical composition according to claim 7 to a subject in need.

* * * * *

UNITED STATES PATENT AND TRADEMARK OFFICE
CERTIFICATE OF CORRECTION

PATENT NO. : 10,562,900 B2
APPLICATION NO. : 15/504854
DATED : February 18, 2020
INVENTOR(S) : Meiyu Geng et al.

Page 1 of 2

It is certified that error appears in the above-identified patent and that said Letters Patent is hereby corrected as shown below:

In the Claims

Claim 4, Column 115, Lines 27-40, the formula: 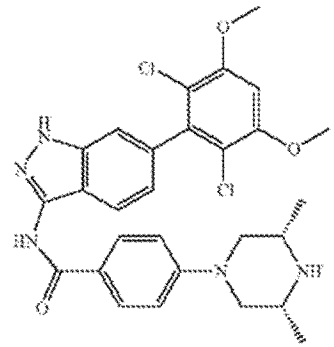

Should be replaced with the formula: 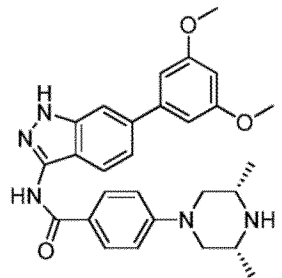

Claim 4, Column 122, Lines 1-15, the formula: 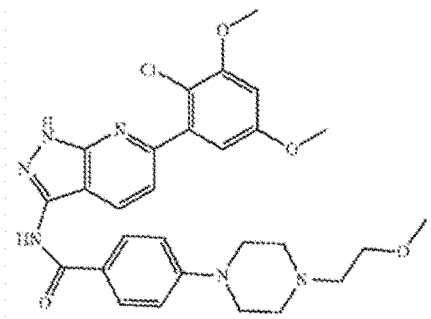

Signed and Sealed this
Thirty-first Day of May, 2022

Katherine Kelly Vidal
*Director of the United States Patent and Trademark Office*

CERTIFICATE OF CORRECTION (continued)
U.S. Pat. No. 10,562,900 B2

Should be replaced with the formula: 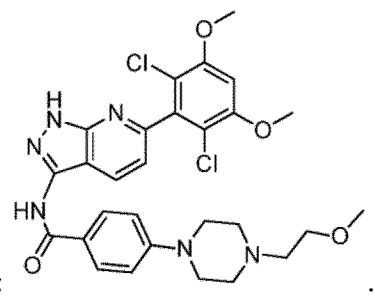 .

Claim 4, Column 127, Lines 35-50, the formula: 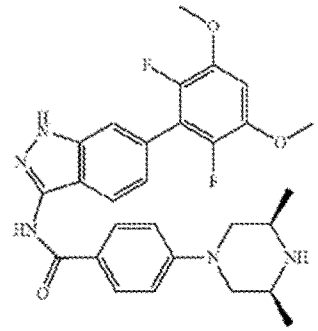

Should be replaced with the formula: 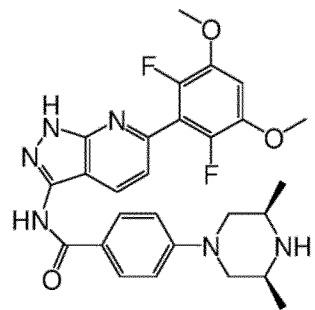 .